US009981048B2

(12) United States Patent
Fox et al.

(10) Patent No.: US 9,981,048 B2
(45) Date of Patent: May 29, 2018

(54) METHODS FOR THE TREATMENT AND PREVENTION OF LIVER DISEASE

(71) Applicant: University of Pittsburgh—of the Commonwealth System of Higher Education, Pittsburgh, PA (US)

(72) Inventors: Ira Jacob Fox, Pittsburgh, PA (US); Aaron W. Bell, West Mifflin, PA (US); Taichiro N. Nishikawa, Pittsburgh, PA (US); Alejandro Soto-Gutierrez, Pittsburgh, PA (US); Yoram Vodovotz, Sewickley, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 350 days.

(21) Appl. No.: 14/177,928

(22) Filed: Feb. 11, 2014

(65) Prior Publication Data

US 2014/0249209 A1 Sep. 4, 2014

Related U.S. Application Data

(60) Provisional application No. 61/763,744, filed on Feb. 12, 2013.

(51) Int. Cl.
| | |
|---|---|
| A61K 48/00 | (2006.01) |
| A61K 31/343 | (2006.01) |
| C07K 14/47 | (2006.01) |
| A61K 45/06 | (2006.01) |
| A61K 31/05 | (2006.01) |
| A61K 31/085 | (2006.01) |
| A61K 31/11 | (2006.01) |
| C12N 15/86 | (2006.01) |

(52) U.S. Cl.
CPC ............ *A61K 48/005* (2013.01); *A61K 31/05* (2013.01); *A61K 31/085* (2013.01); *A61K 31/11* (2013.01); *A61K 31/343* (2013.01); *A61K 45/06* (2013.01); *C07K 14/4702* (2013.01); *C12N 15/86* (2013.01); *C12N 2750/14141* (2013.01); *C12N 2750/14171* (2013.01)

(58) Field of Classification Search
CPC .. A61K 31/7088; A61K 35/407; C12N 5/067; C12N 2501/12
See application file for complete search history.

(56) References Cited

FOREIGN PATENT DOCUMENTS

WO WO 2006/008008 1/2006

OTHER PUBLICATIONS

Poynard et al. Impact of Pegylated Interferon Alfa-2b and Ribavirin on Liver Fibrosis in Patients With Chronic Hepatitis C. Gastroenterology, 2002, vol. 122, pp. 1303-1313.*
Song et al. Intrasplentic transplantation of syngenic hepatocytes modified by IFN- gamma gene ameliorates haptic fibrosis in rats. Transplant International, 2002, vol. 15, pp. 472-478.*
Nishikawa, 2015, JCI, 125:1533-1544.*
Kay, Nature Reviews Genetics, advance online publication, pp. 1-13, published online Apr. 6, 2011.*
Misra, JAPI, 61: 127-133, 2013.*
Villeneuve (2000, Hepatology, 31:207-210).*
Butterworth (2002, Metabolic Brain Disease, 17:221-227).*
Berasian, et al., "Expression of Wilms' tumor suppressor in the liver with cirrhosis" Relation to hepatocyte nuclear factor 4 and hepatocellular function, *Hepatology*, 38(1):148-157 (2003).
Berry, et al., "High-yield preparation of isolated rat liver parenchymal cells: a biochemical and fine structural study", *J. Cell Biol.*, 43(3):506-520 (1969).
Bolotin, et al., "Integrated approach for the identification of human hepatocyte nuclear factor 4α target genes using protein binding microarrays", *Hepatology*, 51(2):642-653 (2010).
Bures, et al., "Techniques and basic experiments for the study of brain and behavior", *Elsevier*, pp. 37-45 (1976).
Cawthon, "Telomere measurement by quantitative PCR", *Nucleic Acids Res.*, 30(10):e47 (2002).
Durrand, et al., "Assessment of the prognosis of cirrhosis: Child-Pugh versus MELD", *J. Heptatol.*, 42(Suppll):S 100-S 107 (2004).
Friedman, "Liver fibrosis—from bench to bedside", *J. Hepatol.*, 38(Suppl 1):S38-S53 (2003).
Gines, et al., "Management of Cirrhosis and Ascites", *The New England Journal of Medicine*, 350:1646-1654 (2004).
Gonzalez, "Regulation of hepatocyte nuclear factor 4α-mediated transcription", *Drug Metabolism Pharmacokinet*, 23(1):2-7 (2008).
Grimm, et al., "In vitro and in vivo gene therapy vector evolution via multispecies interbreeding and retargeting of adeno-associated viruses", *JVI*, 82(12):5887-5911 (2008).
Guevel, "Identification of small molecule regulators of the nuclear receptor HNF4α based on naphthofuran scaffolds", *Bioorganic & Medicinal Chemistry*, 17:7021-7030 (2009).
Hayhurst, et al., "Hepatocyte nuclear factor 4α (nuclear receptor 2A1) is essential for maintenance of hepatic gene expression and lipid homeostasis", *MCB*, 21(4):1393-1403 (2001).
Kobayashi, et al., "Hepatocyte transplantation in rats with decompensated cirrhosis", *Hepatology*, 31(4):851-857 (2000).
Kyrmizi, et al., "Plasticity and expanding complexity of the hepatic transcription factor network during liver development", *Genes & Development*, 20(16):2293-2305 (2006).
Limaye, et al., "Expression of specific hepatocyte and cholangiocyte transcription factors in human liver disease and embryonic development", *Lab. Invest.*, 88(8):865-872 (2008).
Liu, et al., "The microenvironment in hepatocyte regeneration and function in rats with advanced cirrhosis", *Hepatology*, 55:1529-1539 (2012).

(Continued)

*Primary Examiner* — Valarie E Bertoglio
(74) *Attorney, Agent, or Firm* — Baker Botts L.L.P.

(57) ABSTRACT

The presently disclosed invention is directed to the discovery that hepatocyte nuclear factor 4 alpha (HNF4α; also known as NR2A1), a transcription factor, reverses hepatocyte dysfunction in an animal model of cirrhosis, resulting in improvement in hepatic function, treatment of cirrhosis, and prolonged survival.

6 Claims, 17 Drawing Sheets

(56) References Cited

OTHER PUBLICATIONS

Locker, "Transcriptional Control of Hepatocyte Differentiation", *Molecular Pathology of Liver Diseases*, 5:193-211 (2011).
Lopez, et al., "Update on liver transplantation: Indications, organ allocation, and long-term care", *Mt. Sinai J. Med.*, 73(8):1056-1066 (2006).
Marrow, et al., "Direct lineage conversion of terminally differentiated hepatocytes to functional neurons", *Cell Stem Cell*, 9(4):374-382 (2011).
Martinez-Hernandez, et al., "The role of capillarization in hepatic failure: studies in carbon tetrachloride-induced cirrhosis", *Hepatology*, 14(5):864-874 (1991).
Matsushita, et al., "Adeno-associated virus vectors can be efficiently produced without helper virus", *Gene Ther.*, 5(7):938-945 (1998).
Michalopoulos, "Liver regeneration after partial hepatectomy: critical analysis of mechanistic dilemmas", *Am. J. Pathol.*, 176(1):2-13 (2010).
Nagata, et al., "Treatment of cirrhosis and liver failure in rats by hepatocyte xenotransplatation", *Gastroenterology*, 124(2):422-431 (2003).
Odom, et al., "Core transcriptional regulatory circuitry in human hepatocytes", *Molecular Systems Biology*, Article No. 2006.0017 (5 pages) (2006).
Parviz, et al., "Hepatocyte nuclear factor 4α controls the development of a hepatic epithelium and liver morphogenesis", *Nature Genetics*, 34(3):292-296 (2003).
Pessayre, et al., "Mechanism for reduced drug clearance in patients with cirrhosis", *Gastroenterology*, 74(3):566-571 (1978).
Schuppan, et al., "Liver Cirrhosis", *Lancet*, 371(9615):838-851 (2008).
Seglen, "Preparation of isolated rat liver cells", *Methods Cell Biol.*, 13:29-83 (1976).
Sladek, et al., "Hepatocyte Nuclear Factor 4α", *Book Chapter in Nuclear Receptor and Genetics Disease*, Academic Press, London, 2001.
Sladek, et al., "Liver-enriched transcription factor HNF-4 is a novel member of the steroid hormone receptor superfamily", *Genes & Development*, 4(12B):2353-2365 (1990).

Takahashi, et al., "Induction of pluripotent stem cells from adult human fibroblasts by defined factors", *Cell*, 131(5):861-872 (2007).
Vaubourdolle, et al., "Evidence of the intact hepatocyte theory in alcoholic cirrhosis", *Scand J. Gastroenterol.*, 24(4):467-474 (1989).
Yue, et al., "Hepatocyte nuclear factor 4α attenuates hepatic fibrosis in rats", *Gut.*, 59(2):236-246 (2010).
Nishikawa et al., "Rescue of hepatic function in rats with advanced cirrhosis and end-stage liver failure following delivery of HNF4a," AASLD Abstracts No. 1284, Hepatology, 56(4) Suppl.:800A-801A (Oct. 2012).
Takagi et al., "MicroRN As Regulate Human Hepatocyte Nuclear Factor 4α, Modulating the Expression of Metabolic Enzymes and Cell Cycle*," The Journal of Biological Chemistry, 285(7):4415-4422 (2010).
Wertheim, "Novel Technology for Liver Regeneration and Replacement," Liver Transplantation (S1): S41-S46 (2016).
Giannone et al., "Reversal of liver fibrosis by the antagonism of endocannabinoid CB1 receptor in a rat model of CC1(4)-induced advanced cirrhosis," Lab Invest 92:384-395 (2012).
Jiang et al., "Metallothionein Gene Therapy for Chemical-Induced Liver Fibrosis in Mice," Mol Ther. 10(6):1130-1139 (2004).
Lin et al., "Treatment of experimental hepatic fibrosis by combinational delivery of urokinase-type plasminogen activator and hepatocyte growth factor genes," Liver Int. 25:796-807 (2005).
Salgado et al., "Liver Cirrhosis is Reverted by Urokinase-Type Plasminogen Activator Gene Therapy," Mol Ther 2(6):545-551 (2000).
Sayyed et al., "Comparison of the therapeutic effectiveness of human CD34+ and rat bone marrow mesenchymal stem cells on improvement of experimental liver fibrosis in Wistar rats," Int J Physiol Pathophysiol Pharmacol 8(3):128-139 (2016).
Siller-Lopez et al., "Treatment with Human Metalloproteinase-8 Gene Delivery Ameliorates Experimental Rat Liver Cirrhosis," Gastroenterology 126:1122-1133 (2004).
Sobrevals et al., "Insulin-Like Growth Factor I (IGF-I) Expressed from an AAV1 Vector Leads to a Complete Reversion of Liver Cirrhosis in Rats," PLoS One 11(9):e0162955 (2016).
Xu et al., "Metallothionein Gene Transfection Reverses the Phenotype of Activated Human Hepatic Stellate Cells," J Pharmacol Exp Ther 346:48-53 (2013).

* cited by examiner

*p<0.05, **p<0.001, statistical analysis between isolated hepatocytes from decompensated cirrhotic w/o AAV and with AAV-HNF4a treatment

GI: 385298690 (SEQ ID NO: 1)

```
ggtttgaaag gaaggcagag agggcactgg gaggaggcag tgggagggcg gagggcgggg 61
gccttcgggg tgggcgccca gggtagggca ggtggccgcg gcgtggaggc agggagaatg 121
cgactctcca aaaccctcgt cgacatggac atggccgact acagtgctgc actggaccca 181
gcctacacca ccctggaatt tgagaatgtg caggtgttga cgatgggcaa tgacacgtcc 241
ccatcagaag gcaccaacct caacgcgccc aacagcctgg gtgtcagcgc cctgtgtgcc 301
atctgcgggg accgggccac gggcaaacac tacggtgcct cgagctgtga cggctgcaag 361
ggcttcttcc ggaggagcgt gcggaagaac cacatgtact cctgcagatt tagccggcag 421
tgcgtggtgg acaaagacaa gaggaaccag tgccgctact gcaggctcaa gaaatgcttc 481
cgggctggca tgaagaagga agccgtccag aatgagcggg accggatcag cactcgaagg 541
tcaagctatg aggacagcag cctgccctcc atcaatgcgc tcctgcaggc ggaggtcctg 601
tcccgacaga tcacctcccc cgtctccggg atcaacggcg acattcgggc gaagaagatt 661
gccagcatcg cagatgtgtg tgagtccatg aaggagcagc tgctggttct cgttgagtgg 721
gccaagtaca tcccagcttt ctgcgagctc ccctggacg accaggtggc cctgctcaga 781
gcccatgctg gcgagcacct gctgctcgga gccaccaaga gatccatggt gttcaaggac 841
gtgctgctcc taggcaatga ctacattgtc cctcggcact gccccggagct ggcggagatg 901
agccgggtgt ccatacgcat ccttgacgag ctggtgctgc ccttccagga gctgcagatc 961
gatgacaatg agtatgccta cctcaaagcc atcatcttct ttgacccaga tgccaagggg 1021
ctgagcgatc cagggaagat caagcggctg cgttcccagg tgcaggtgag cttggaggac 1081
tacatcaacg accgccagta tgactcgcgt ggccgctttg gagagctgct gctgctgctg 1141
cccaccttgc agagcatcac ctggcagatg atcgagcaga tccagttcat caagctcttc 1201
ggcatggcca agattgacaa cctgttgcag gagatgctgc tgggagggtc ccccagcgat 1261
gcaccccatg cccaccaccc cctgcaccct cacctgatgc aggaacatat gggaaccaac 1321
gtcatcgttg ccaacacaat gcccactcac ctcagcaacg gacagatgtc caccccctgag 1381
accccacagc cctcaccgcc aggtggctca gggtctgagc cctataagct cctgccggga 1441
gccgtcgcca caatcgtcaa gcccctctct gccatccccc agccgaccat caccaagcag 1501
gaagttatct agcaagccgc tggggcttgg gggctccact ggctcccccc agcccctaa 1561
gagagcacct ggtgatcacg tggtcacggc aaaggaagac gtgatgccag gaccagtccc 1621
agagcaggaa tgggaaggat gaagggcccg agaacatggc ctaagggcca catcccactg 1681
ccacccttga cgccctgctc tggataacaa gactttgact tggggagacc tctactgcct 1741
tggacaactt ttctcatgtt gaagccactg ccttcacctt caccttcatc catgtccaac 1801
ccccgacttc atcccaaagg acagccgcct ggagatgact tgaggcctta cttaaaccca 1861
gctcccttct tccctagcct ggtgcttctc ctctcctagc ccctgtcatg gtgtccagac 1921
agagccctgt gaggctgggt ccaattgtgg cacttgggc accttgctcc tcttctgct 1981
gctgccccca cctctgctgc ctccctctgc tgtcaccttg ctcagccatc ccgtcttctc 2041
caacaccacc tctccagagg ccaaggaggc cttggaaacg attcccccag tcattctggg 2101
aacatgttgt aagcactgac tgggaccagg caccaggcag ggtctagaag gctgtggtga 2161
gggaagacgc ctttctcctc caacccaacc tcatcctcct tcttcaggga cttgggtggg 2221
tacttgggtg aggatccctg aaggccttca acccgagaaa acaaacccag gttggcgact 2281
gcaacaggaa cttggagtgg agaggaaaag catcagaaag aggcagacca tccaccaggc 2341
ctttgagaaa gggtagaatt ctggctggta gagcaggtga gatgggacat tccaaagaac 2401
agcctgagcc aaggcctagt ggtagtaaga atctagcaag aattgaggaa gaatggtgtg 2461
ggagagggat gatgaagaga gagagggcct gctggagagc atagggtctg gaacaccagg 2521
ctgaggtcct gatcagcttc aaggagtatg cagggagctg ggcttccaga aaatgaacac 2581
agcagttctg cagaggacgg gaggctggaa gctgggaggt caggtggggt ggatgatata 2641
```

FIG. 7A1

```
atgcgggtga gagtaatgag gcttggggct ggagaggaca agatgggtaa acccctcacat 2701
cagagtgaca tccaggagga ataagctccc agggcctgtc tcaagctctt ccttactccc 2761
aggcactgtc ttaaggcatc tgacatgcat catctcattt aatcctccct tcctccctat 2821
taacctagag attgtttttg ttttttattc tcctcctccc tccccgccct cacccgcccc 2881
actccctcct aacctagaga ttgttacaga agctgaaatt gcgttctaag aggtgaagtg 2941
attttttttc tgaaactcac acaactagga agtggctgag tcaggacttg aacccaggtc 3001
tccctggatc agaacaggag ctcttaacta cagtggctga atagcttctc caaaggctcc 3061
ctgtgttctc accgtgatca agttgagggg cttccggctc ccttctacag cctcagaaac 3121
cagactcgtt cttctgggaa ccctgcccac tccaggacc aagattggcc tgaggctgca 3181
ctaaaattca cttagggtcg agcatcctgt ttgctgataa atattaagga gaattcatga 3241
ctcttgacag ctttctctc ttcactcccc aagtcaaggg gagggtggc agggtctgt 3301
ttcctggaag tcaggctcat ctggcctgtt ggcatggggg tgggacagtg tgcacagtgt 3361
ggggcaggg gagggctaag caggcctggg tttgagggct gctccggaga ccgtcactcc 3421
aggtgcattc tggaagcatt agaccccagg atggagcgac cagcatgtca tccatgtgga 3481
atcttggtgg ctttgaggac attctggaaa atgccactga ccagtgtgaa caaagggat 3541
gtgttatggg gctggaggtg tgattaggta ggagggaaac tgttggaccg actcctgccc 3601
cctgctcaac actgaccct ctgagtggtt ggaggcagtg ccccagtgcc cagaaatccc 3661
accattagtg attgtttttt atgagaaaga ggcgtggaga agtattgggg caatgtgtca 3721
gggaggaatc accacatccc tacggcagtc ccagccaagc ccccaatccc agcggagact 3781
gtgccctgct cagagctccc aagccttccc ccaccacctc actcaagtgc ccctgaaatc 3841
cctgccagac ggctcagcct ggtctgcggt aaggcaggga ggctggaacc atttctgggc 3901
attgtggtca ttcccactgt gttcctccac ctcctcctc cagcgttgct cagacctctg 3961
tcttgggaga aaggttgaga taagaatgtc ccatggagtg ccgtgggcaa cagtggccct 4021
tcatgggaac aatctgttgg agcaggggt cagttctctg ctgggaatct accccttct 4081
ggaggagaaa cccattccac cttaataact ttattgtaat gtgagaaaca caaacaaag 4141
tttactttttt tgactctaag ctgacatgat attagaaaat ctctcgctct ctttttttt 4201
tttttttttt ttttggcta cttgagttgt ggtcctaaaa cataaaatct gatggacaaa 4261
cagagggttg ctgggggggac aagcgtgggc acaatttccc caccaagaca ccctgatctt 4321
caggcgggtc tcaggagctt ctaaaaatcc gcatggctct cctgagagtg gacagaggag 4381
aggagagggt cagaaatgaa cgctcttcta ttttcttgtca ttaccaagcc aattactttt 4441
gccaaatttt tctgtgatct gccctgatta agatgaattg tgaaatttac atcaagcaat 4501
tatcaaagcg ggctgggtcc catcagaacg acccacatct ttctgtgggt gtgaatgtca 4561
ttaggtcttg cgctgacccc tgagccccca tcactgccgc ctgatgggc aaagaaacaa 4621
aaaacattc ttactcttct gtgttttaac aaaagtttat aaaacaaaat aaatggcgca 4681
tatgttttct aaaaaaaaaa aaaaaaa
```

GI: 385298689 (SEQ ID NO: 2)

```
ggtttgaaag gaaggcagag agggcactgg gaggaggcag tggagggcg gagggcgggg 61
gccttcgggg tgggcgccca gggtagggca ggtggccgcg gcgtggaggc agggagaatg 121
cgactctcca aaaccctcgt cgacatggac atggccgact acagtgctgc actggaccca 181
gcctacacca ccctggaatt tgagaatgtg caggtgttga cgatgggcaa tgacacgtcc 241
ccatcagaag gcaccaacct caacgcgccc aacagcctgg gtgtcagcgc cctgtgtgcc 301
atctgcgggg accgggccac gggcaaacac tacggtgcct cgagctgtga cggctgcaag 361
ggcttcttcc ggaggagcgt gcggaagaac cacatgtact cctgcagatt tagccggcag 421
tgcgtggtgg acaaagacaa gaggaaccag tgccgctact gcaggctcaa gaaatgcttc 481
```

FIG. 7A2

```
cgggctggca tgaagaagga agccgtccag aatgagcggg accggatcag cactcgaagg 541
tcaagctatg aggacagcag cctgccctcc atcaatgcgc tcctgcaggc ggaggtcctg 601
tcccgacaga tcacctcccc cgtctccggg atcaacggcg acattcgggc gaagaagatt 661
gccagcatcg cagatgtgtg tgagtccatg aaggagcagc tgctggttct cgttgagtgg 721
gccaagtaca tcccagcttt ctgcgagctc cccctggacg accaggtggc cctgctcaga 781
gcccatgctg gcgagcacct gctgctcgga gccaccaaga gatccatggt gttcaaggac 841
gtgctgctcc taggcaatga ctacattgtc cctcggcact gcccggagct ggcggagatg 901
agccgggtgt ccatacgcat ccttgacgag ctggtgctgc ccttccagga gctgcagatc 961
gatgacaatg agtatgccta cctcaaagcc atcatcttct ttgacccaga tgccaagggg 1021
ctgagcgatc cagggaagat caagcggctg cgttcccagg tgcaggtgag cttggaggac 1081
tacatcaacg accgccagta tgactcgcgt ggccgctttg gagagctgct gctgctgctg 1141
cccaccttgc agagcatcac ctggcagatg atcgagcaga tccagttcat caagctcttc 1201
ggcatggcca agattgacaa cctgttgcag gagatgctgc tgggagggtc ccccagcgat 1261
gcaccccatg cccaccaccc cctgcaccct cacctgatgc aggaacatat gggaaccaac 1321
gtcatcgttg ccaacacaat gcccactcac ctcagcaacg gacagatgtg tgagtggccc 1381
cgacccaggg gacaggcagc caccccctgag accccacagc cctcaccgcc aggtggctca 1441
gggtctgagc cctataagct cctgccggga gccgtcgcca caatcgtcaa gcccctctct 1501
gccatccccc agccgaccat caccaagcag gaagttatct agcaagccgc tggggcttgg 1561
gggctccact ggctcccccc agcccctaa gagagcacct ggtgatcacg tggtcacggc 1621
aaaggaagac gtgatgccag gaccagtccc agagcaggaa tgggaaggat gaagggcccg 1681
agaacatggc ctaagggcca catcccactg ccaccccttga cgccctgctc tggataacaa 1741
gactttgact tggggagacc tctactgcct tggacaactt ttctcatgtt gaagccactg 1801
ccttcacctt caccttcatc catgtccaac ccccgacttc atcccaaagg acagccgcct 1861
ggagatgact tgaggcctta cttaaaccca gctcccttct tccctagcct ggtgcttctc 1921
ctctcctagc ccctgtcatg gtgtccagac agagccctgt gaggctgggt ccaattgtgg 1981
cacttggggc accttgctcc tccttctgct gctgccccca cctctgctgc ctccctctgc 2041
tgtcaccttg ctcagccatc ccgtcttctc caacaccacc tctccagagg ccaaggaggc 2101
cttggaaacg attcccccag tcattctggg aacatgttgt aagcactgac tgggaccagg 2161
caccaggcag ggtctagaag gctgtggtga gggaagacgc ctttctcctc caacccaacc 2221
tcatcctcct tcttcaggga cttgggtggg tacttgggtg aggatccctg aaggccttca 2281
acccgagaaa acaaacccag gttggcgact gcaacaggaa cttggagtgg agaggaaaag 2341
catcagaaag aggcagacca tccaccaggc ctttgagaaa gggtagaatt ctggctggta 2401
gagcaggtga gatgggacat tccaaagaac agcctgagcc aaggcctagt ggtagtaaga 2461
atctagcaag aattgaggaa gaatggtgtg ggagagggat gatgaagaga gagagggcct 2521
gctggagagc atagggtctg gaacaccagg ctgaggtcct gatcagcttc aaggagtatg 2581
cagggagctg ggcttccaga aaatgaacac agcagttctg cagaggacgg gaggctggaa 2641
gctgggaggt caggtggggt ggatgatata atgcgggtga gagtaatgag gcttggggct 2701
ggagaggaca agatgggtaa accctcacat cagagtgaca tccaggagga ataagctccc 2761
agggcctgtc tcaagctctt ccttactccc aggcactgtc ttaaggcatc tgacatgcat 2821
catctcattt aatcctccct tcctccctat taacctagag attgttttg tttttattc 2881
tcctcctccc tccccgccct cacccgcccc actccctcct aacctagaga ttgttacaga 2941
agctgaaatt gcgttctaag aggtgaagtg attttttttc tgaaactcac acaactagga 3001
agtggctgag tcaggacttg aacccaggtc tccctggatc agaacaggag ctcttaacta 3061
cagtggctga atagcttctc caaaggctcc ctgtgttctc accgtgatca agttgagggg 3121
```

FIG. 7A3 cttccggctc ccttctacag cctcagaaac cagactcgtt cttctgggaa ccctgcccac 3181
tcccaggacc aagattggcc tgaggctgca ctaaaattca cttagggtcg agcatcctgt 3241
ttgctgataa atattaagga gaattcatga ctcttgacag cttttctctc ttcactcccc 3301
aagtcaaggg gaggggtggc aggggtctgt ttcctggaag tcaggctcat ctggcctgtt 3361
ggcatggggg tgggacagtg tgcacagtgt gggggcaggg gagggctaag caggcctggg 3421
tttgagggct gctccggaga ccgtcactcc aggtgcattc tggaagcatt agaccccagg 3481
atggagcgac cagcatgtca tccatgtgga atcttggtgg ctttgaggac attctggaaa 3541
atgccactga ccagtgtgaa caaaagggat gtgttatggg gctggaggtg tgattaggta 3601
ggagggaaac tgttggaccg actcctgccc cctgctcaac actgacccct ctgagtggtt 3661
ggaggcagtg ccccagtgcc cagaaatccc accattagtg attgtttttt atgagaaaga 3721
ggcgtggaga agtattgggg caatgtgtca ggggaggaatc cccacatccc tacggcagtc 3781
ccagccaagc ccccaatccc agcggagact gtgccctgct cagagctccc aagccttccc 3841
ccaccacctc actcaagtgc ccctgaaatc cctgccagac ggctcagcct ggtctgcggt 3901
aaggcaggga ggctggaacc atttctgggc attgtggtca tcccactgt gttcctccac 3961
ctcctccctc cagcgttgct cagacctctg tcttgggaga aaggttgaga taagaatgtc 4021
ccatggagtg ccgtgggcaa cagtggccct tcatgggaac aatctgttgg agcagggggt 4081
cagttctctg ctgggaatct accccttct ggaggagaaa cccattccac cttaataact 4141
ttattgtaat gtgagaaaca caaaacaaag tttacttttt tgactctaag ctgacatgat 4201
attagaaaat ctctcgctct cttttttttt tttttttttt ttttggcta cttgagttgt 4261
ggtcctaaaa cataaaatct gatggacaaa cagagggttg ctgggggac aagcgtgggc 4321
acaatttccc caccaagaca ccctgatctt caggcgggtc tcaggagctt ctaaaaatcc 4381
gcatggctct cctgagagtg gacagaggag aggagagggt cagaaatgaa cgctcttcta 4441
tttcttgtca ttaccaagcc aattactttt gccaaatttt tctgtgatct gccctgatta 4501
agatgaattg tgaaatttac atcaagcaat tatcaaagcg ggctgggtcc catcagaacg 4561
acccacatct ttctgtgggt gtgaatgtca ttaggtcttg cgctgacccc tgagccccca 4621
tcactgccgc ctgatggggc aaagaaacaa aaacatttc ttactcttct gtgttttaac 4681
aaaagtttat aaaacaaaat aaatggcgca tatgtttct aaaaaaaaaa aaaaaaa

GI: 385298691 (SEQ ID NO: 3)

ggtttgaaag gaaggcagag agggcactgg gaggaggcag tgggagggcg gagggcgggg 61
gccttcgggg tgggcgccca gggtagggca ggtggccgcg gcgtggaggc agggagaatg 121
cgactctcca aaaccctcgt cgacatggac atggccgact acagtgctgc actggaccca 181
gcctacacca ccctggaatt tgagaatgtg caggtgttga cgatgggcaa tgacacgtcc 241
ccatcagaag gcaccaacct caacgcgccc aacagcctgg gtgtcagcgc cctgtgtgcc 301
atctgcgggg accgggccac gggcaaacac tacggtgcct cgagctgtga cggctgcaag 361
ggcttcttcc ggaggagcgt gcggaagaac cacatgtact cctgcagatt tagccggcag 421
tgcgtggtgg acaaagacaa gaggaaccag tgccgctact gcaggctcaa gaaatgcttc 481
cgggctggca tgaagaagga agccgtccag aatgagcggg accggatcag cactcgaagg 541
tcaagctatg aggacagcag cctgccctcc atcaatgcgc tcctgcaggc ggaggtcctg 601
tcccgacaga tcacctcccc cgtctccggg atcaacggcg acattcgggc gaagaagatt 661
gccagcatcg cagatgtgtg tgagtccatg aaggagcagc tgctggttct cgttgagtgg 721
gccaagtaca tcccagcttt ctgcgagctc ccctggacg accaggtggc cctgctcaga 781
gcccatgctg gcgagcacct gctgctcgga gccaccaaga gatccatggt gttcaaggac 841
gtgctgctcc taggcaatga ctacattgtc cctcggcact gcccggagct ggcgggagatg 901
agccgggtgt ccatacgcat ccttgacgag ctggtgctgc ccttccagga gctgcagatc 961

```
gatgacaatg agtatgccta cctcaaagcc atcatcttct ttgacccaga tgccaagggg 1021
ctgagcgatc cagggaagat caagcggctg cgttcccagg tgcaggtgag cttggaggac 1081
tacatcaacg accgccagta tgactcgcgt ggccgctttg gagagctgct gctgctgctg 1141
cccaccttgc agagcatcac ctggcagatg atcgagcaga tccagttcat caagctcttc 1201
ggcatggcca agattgacaa cctgttgcag gagatgctgc tgggaggtcc gtgccaagcc 1261
caggaggggc ggggttggag tggggactcc ccaggagaca ggcctcacac agtgagctca 1321
ccctcagct ccttggcttc cccactgtgc cgctttgggc aagttgctta acctgtctgt 1381
gcctcagttt cctcaccaga aaaatgggaa caaggcaatg gtctatttgt tcaggcaccg 1441
agaacctagc acgtgccagt cactgttcta agtgctggca attcagcaaa gaacaagatc 1501
tttgccctcg gggaggctgt gtgtgtgtga gtatgtatgg atgcgtggat atctgtgtat 1561
atgcccgtat gtgcgtgcat gtgtatataa agcctcacat tttatgattt tgaaataaac 1621
aggtaata
```

GI: 385298688 (SEQ ID NO: 4)

```
ggccatggtc agcgtgaacg cgcccctcgg ggctccagtg gagagttctt acgacacgtc 61
cccatcagaa ggcaccaacc tcaacgcgcc caacagcctg ggtgtcagcg ccctgtgtgc 121
catctgcggg gaccgggcca cgggcaaaca ctacggtgcc tcgagctgtg acggctgcaa 181
gggcttcttc cggaggagcg tgcggaagaa ccacatgtac tcctgcagat ttagccggca 241
gtgcgtggtg gacaaagaca gaggaaccag tgccgctac tgcaggctca agaaatgctt 301
ccgggctggc atgaagaagg aagccgtcca gaatgagcgg gaccggatca gcactcgaag 361
gtcaagctat gaggacagca gcctgccctc catcaatgcg ctcctgcagg cggaggtcct 421
gtcccgacag atcacctccc ccgtctccgg gatcaacggc gacattcggg cgaagaagat 481
tgccagcatc gcagatgtgt gtgagtccat gaaggagcag ctgctggttc tcgttgagtg 541
ggccaagtac atccagcttt ctgcgagct ccccctggac gaccaggtgg ccctgctcag 601
agcccatgct ggcgagcacc tgctgctcgg agccaccaag agatccatgg tgttcaagga 661
cgtgctgctc ctaggcaatg actacattgt ccctcggcac tgcccggagc tggcggagat 721
gagccgggtg tccatacgca tccttgacga gctggtgctg cccttccagg agctgcagat 781
cgatgacaat gagtatgcct acctcaaagc catcatcttc tttgacccag atgccaaggg 841
gctgagcgat ccagggaaga tcaagcggct gcgttcccag gtgcaggtga gcttggagga 901
ctacatcaac gaccgccagt atgactcgcg tggccgcttt ggagagctgc tgctgctgct 961
gcccaccttg cagagcatca cctggcagat gatcgagcag atccagttca tcaagctctt 1021
cggcatggcc aagattgaca acctgttgca ggagatgctg ctgggagggt ccccagcga 1081
tgcaccccat gcccaccacc ccctgcaccc tcacctgatg caggaacata tgggaaccaa 1141
cgtcatcgtt gccaacacaa tgcccactca cctcagcaac ggacagatgt gtgagtggcc 1201
ccgacccagg ggacaggcag ccaccccctga acccccacag ccctcaccgc caggtggctc 1261
agggtctgag ccctataagc tcctgccggg agccgtcgcc acaatcgtca gcccctctc 1321
tgccatcccc cagccgacca tcaccaagca ggaagttatc tagcaagccg ctggggcttg 1381
ggggctccac tggctccccc cagcccccta agagagcacc tggtgatcac gtggtcacgg 1441
caaaggaaga cgtgatgcca ggaccagtcc cagagcagga atgggaagga tgaagggccc 1501
gagaacatgg cctaagggcc acatccact gccacccttg acgccctgct ctggataaca 1561
agactttgac ttggggagac ctctactgcc ttgacaact tttctcatgt tgaagccact 1621
gccttcacct tcaccttcat ccatgtccaa ccccgactt catcccaaag gacagccgcc 1681
tggagatgac ttgaggcctt acttaaaccc agctccctc ttccctagcc tggtgcttct 1741
cctctcctag cccctgtcat ggtgtccaga cagagccctg tgaggctggg tccaattgtg 1801
gcacttgggg caccttgctc ctccttctgc tgctgccccc acctctgctg cctccctctg 1861
```

FIG. 7A5

```
ctgtcacctt gctcagccat cccgtcttct ccaacaccac ctctccagag gccaaggagg 1921
ccttggaaac gattcccccca gtcattctgg gaacatgttg taagcactga ctgggaccag 1981
gcaccaggca gggtctagaa ggctgtggtg agggaagacg cctttctcct ccaacccaac 2041
ctcatcctcc ttcttcaggg acttgggtgg gtacttgggt gaggatccct gaaggccttc 2101
aacccgagaa aacaaaccca ggttggcgac tgcaacagga acttggagtg gagaggaaaa 2161
gcatcagaaa gaggcagacc atccaccagg cctttgagaa agggtagaat tctggctggt 2221
agagcaggtg agatgggaca ttccaaagaa cagcctgagc caaggcctag tggtagtaag 2281
aatctagcaa gaattgagga agaatggtgt gggagaggga tgatgaagag agagagggcc 2341
tgctggagag catagggtct ggaacaccag gctgaggtcc tgatcagctt caaggagtat 2401
gcagggagct gggcttccag aaaatgaaca cagcagttct gcagaggacg ggaggctgga 2461
agctgggagg tcaggtgggg tggatgatat aatgcgggtg agagtaatga ggcttggggc 2521
tggagaggac aagatgggta aaccctcaca tcagagtgac atccaggagg aataagctcc 2581
cagggcctgt ctcaagctct tccttactcc caggcactgt cttaaggcat ctgacatgca 2641
tcatctcatt taatcctccc ttcctcccta ttaacctaga gattgttttt gttttttatt 2701
ctcctcctcc ctccccgccc tcacccgccc cactccctcc taacctagag attgttacag 2761
aagctgaaat tgcgttctaa gaggtgaagt gattttttttt ctgaaactca cacaactagg 2821
aagtggctga gtcaggactt gaacccaggt ctccctggat cagaacagga gctcttaact 2881
acagtggctg aatagcttct ccaaaggctc cctgtgttct caccgtgatc aagttgaggg 2941
gcttccggct cccttctaca gcctcagaaa ccagactcgt tcttctggga accctgccca 3001
ctcccaggac caagattggc ctgaggctgc actaaaattc acttagggtc gagcatcctg 3061
tttgctgata aatattaagg agaattcatg actcttgaca gcttttctct cttcactccc 3121
caagtcaagg ggaggggtgg caggggtctg tttcctggaa gtcaggctca tctggcctgt 3181
tggcatgggg gtgggacagt gtgcacagtg tgggggcagg ggagggctaa gcaggcctgg 3241
gtttgagggc tgctccggag accgtcactc caggtgcatt ctggaagcat tagaccccag 3301
gatggagcga ccagcatgtc atccatgtgg aatcttggtg gctttgagga cattctggaa 3361
aatgccactg accagtgtga acaaaaggga tgtgttatgg ggctggaggt gtgattaggt 3421
aggagggaaa ctgttggacc gactcctgcc ccctgctcaa cactgacccc tctgagtggt 3481
tggaggcagt gccccagtgc ccagaaatcc caccattagt gattgttttt tatgagaaag 3541
aggcgtggag aagtattggg gcaatgtgtc agggaggaat caccacatcc ctacggcagt 3601
cccagccaag cccccaatcc cagcggagac tgtgccctgc tcagagctcc caagccttcc 3661
cccaccacct cactcaagtg cccctgaaat ccctgccaga cggctcagcc tggtctgcgg 3721
taaggcaggg aggctggaac catttctggg cattgtggtc attcccactg tgttcctcca 3781
cctcctccct ccagcgttgc tcagacctct gtcttgggag aaaggttgag ataagaatgt 3841
cccatggagt gccgtgggca acagtggccc ttcatgggaa caatctgttg gagcagggg 3901
tcagttctct gctgggaatc taccccttc tggaggagaa acccattcca ccttaataac 3961
tttattgtaa tgtgagaaac acaaaacaaa gtttactttt ttgactctaa gctgacatga 4021
tattagaaaa tctctcgctc ttttttttttt ttttttttt ttttttggct acttgagttg 4081
tggtcctaaa acataaaatc tgatggacaa acagagggtt gctgggggga caagcgtggg 4141
cacaatttcc ccaccaagac accctgatct tcaggcgggt ctcaggagct tctaaaaatc 4201
cgcatggctc tcctgagagt ggacagagga gaggagaggg tcagaaatga acgctcttct 4261
atttcttgtc attaccaagc caattacttt tgccaaattt ttctgtgatc tgccctgatt 4321
aagatgaatt gtgaaattta catcaagcaa ttatcaaagc gggctgggtc ccatcagaac 4381
gacccacatc tttctgtggg tgtgaatgtc attaggtctt gcgctgaccc ctgagccccc 4441
atcactgccg cctgatgggg caaagaaaca aaaacatttt cttactcttc tgtgttttaa 4501
caaaagttta taaaacaaaa taaatggcgc atatgttttc taaaaaaaaa aaaaaaa
```

FIG. 7A6

GI: 385298686 (SEQ ID NO: 5)

```
ggccatggtc agcgtgaacg cgcccctcgg ggctccagtg gagagttctt acgacacgtc 61
cccatcagaa ggcaccaacc tcaacgcgcc caacagcctg ggtgtcagcg ccctgtgtgc 121
catctgcggg gaccgggcca cgggcaaaca ctacggtgcc tcgagctgtg acggctgcaa 181
gggcttcttc cggaggagcg tgcggaagaa ccacatgtac tcctgcagat ttagccggca 241
gtgcgtggtg gacaaagaca agaggaacca gtgccgctac tgcaggctca agaaatgctt 301
ccgggctggc atgaagaagg aagccgtcca gaatgagcgg gaccggatca gcactcgaag 361
gtcaagctat gaggacagca gcctgccctc catcaatgcg ctcctgcagg cggaggtcct 421
gtcccgacag atcacctccc ccgtctccgg gatcaacggc gacattcggg cgaagaagat 481
tgccagcatc gcagatgtgt gtgagtccat gaaggagcag ctgctggttc tcgttgagtg 541
ggccaagtac atcccagctt tctgcgagct ccccctggac gaccaggtgg ccctgctcag 601
agcccatgct ggcgagcacc tgctgctcgg agccaccaag agatccatgg tgttcaagga 661
cgtgctgctc ctaggcaatg actacattgt ccctcggcac tgcccggagc tggcggagat 721
gagccgggtg tccatacgca tccttgacga gctggtgctg cccttccagg agctgcagat 781
cgatgacaat gagtatgcct acctcaaagc catcatcttc tttgacccag atgccaaggg 841
gctgagcgat ccaggaaga tcaagcggct gcgttcccag gtgcaggtga gcttggagga 901
ctacatcaac gaccgccagt atgactcgcg tggccgcttt ggagagctgc tgctgctgct 961
gccaccttg cagagcatca cctggcagat gatcgagcag atccagttca tcaagctctt 1021
cggcatggcc aagattgaca acctgttgca ggagatgctg ctgggagggt cccccagcga 1081
tgcaccccat gcccaccacc ccctgcaccc tcacctgatg caggaacata tgggaaccaa 1141
cgtcatcgtt gccaacacaa tgcccactca cctcagcaac ggacagatgt ccaccccctga 1201
gaccccacag ccctcaccgc caggtggctc agggtctgag ccctataagc tcctgccggg 1261
agccgtcgcc acaatcgtca agccctctc tgccatcccc cagccgacca tcaccaagca 1321
ggaagttatc tagcaagccg ctggggcttg ggggctccac tggctccccc cagcccccta 1381
agagagcacc tggtgatcac gtggtcacgg caaaggaaga cgtgatgcca ggaccagtcc 1441
cagagcagga atgggaagga tgaagggccc gagaacatgg cctaagggcc acatcccact 1501
gccacccttg acgccctgct ctggataaca agactttgac ttggggagac ctctactgcc 1561
ttggacaact tttctcatgt tgaagccact gccttcacct tcaccttcat ccatgtccaa 1621
cccccgactt catcccaaag gacagccgcc tggagatgac ttgaggcctt acttaaaccc 1681
agctcccttc ttccctagcc tggtgcttct cctctcctag cccctgtcat ggtgtccaga 1741
cagagccctg tgaggctggg tccaattgtg gcacttgggg cacctgctc ctccttctgc 1801
tgctgccccc acctctgctg cctccctctg ctgtcacctt gctcagccat cccgtcttct 1861
ccaacaccac ctctccagag gccaaggagg ccttggaaac gattcccca gtcattctgg 1921
gaacatgttg taagcactga ctgggaccag gcaccaggca gggtctagaa ggctgtggtg 1981
agggaagacg cctttctcct ccaacccaac ctcatcctcc ttcttcaggg acttgggtgg 2041
gtacttgggt gaggatccct gaaggccttc aacccgagaa aacaaaccca ggttggcgac 2101
tgcaacagga acttggagtg gagaggaaaa gcatcagaaa gaggcagacc atccaccagg 2161
cctttgagaa agggtagaat tctggctggt agagcaggtg agatgggaca ttccaaagaa 2221
cagcctgagc caaggcctag tggtagtaag aatctagcaa gaattgagga agaatggtgt 2281
gggagaggga tgatgaagag agagagggcc tgctggagag cataggtct ggaacaccag 2341
gctgaggtcc tgatcagctt caaggagtat gcagggagct gggcttccag aaaatgaaca 2401
cagcagttct gcagaggacg ggaggctgga agctgggagg tcaggtgggg tggatgatat 2461
aatgcgggtg agagtaatga ggcttgggc tggagaggac aagatgggta aaccctcaca 2521
tcagagtgac atccaggagg aataagctcc cagggcctgt ctcaagctct tccttactcc 2581
caggcactgt cttaaggcat ctgacatgca tcatctcatt taatcctccc ttcctcccta 2641
```

FIG. 7A7

```
ttaacctaga gattgttttt gtttttatt ctcctcctcc ctccccgccc tcacccgccc 2701
cactccctcc taacctagag attgttacag aagctgaaat tgcgttctaa gaggtgaagt 2761
gatttttttt ctgaaactca cacaactagg aagtggctga gtcaggactt gaacccaggt 2821
ctccctggat cagaacagga gctcttaact acagtggctg aatagcttct ccaaaggctc 2881
cctgtgttct caccgtgatc aagttgaggg gcttccggct cccttctaca gcctcagaaa 2941
ccagactcgt tcttctggga accctgccca ctccaggac caagattggc ctgaggctgc 3001
actaaaattc acttagggtc gagcatcctg tttgctgata aatattaagg agaattcatg 3061
actcttgaca gcttttctct cttcactccc caagtcaagg ggaggggtgg caggggtctg 3121
tttcctggaa gtcaggctca tctggcctgt tggcatgggg gtgggacagt gtgcacagtg 3181
tgggggcagg ggagggctaa gcaggcctgg gtttgagggc tgctccggag accgtcactc 3241
caggtgcatt ctggaagcat tagaccccag gatggagcga ccagcatgtc atccatgtgg 3301
aatcttggtg gctttgagga cattctggaa aatgccactg accagtgtga acaaaaggga 3361
tgtgttatgg ggctggaggt gtgattaggt aggagggaaa ctgttggacc gactcctgcc 3421
ccctgctcaa cactgacccc tctgagtggt tggaggcagt gccccagtgc ccagaaatcc 3481
caccattagt gattgttttt tatgagaaag aggcgtggag aagtattggg gcaatgtgtc 3541
agggaggaat caccacatcc ctacggcagt cccagccaag cccccaatcc cagcggagac 3601
tgtgccctgc tcagagctcc caagccttcc cccaccacct cactcaagtg cccctgaaat 3661
ccctgccaga cggctcagcc tggtctgcgg taaggcaggg aggctggaac catttctggg 3721
cattgtggtc attcccactg tgttcctcca cctcctccct ccagcgttgc tcagacctct 3781
gtcttgggag aaaggttgag ataagaatgt cccatggagt gccgtgggca acagtggccc 3841
ttcatgggaa caatctgttg gagcagggg tcagttctct gctgggaatc taccccttc 3901
tggaggagaa acccattcca ccttaataac tttattgtaa tgtgagaaac acaaacaaa 3961
gtttactttt ttgactctaa gctgacatga tattagaaaa tctctcgctc tctttttttt 4021
tttttttttt tttttggct acttgagttg tggtcctaaa acataaaatc tgatggacaa 4081
acagagggtt gctgggggga caagcgtggg cacaatttcc ccaccaagac accctgatct 4141
tcaggcgggt ctcaggagct tctaaaaatc cgcatggctc tcctgagagt ggacagagga 4201
gaggagaggg tcagaaatga acgctcttct atttcttgtc attaccaagc caattacttt 4261
tgccaaattt ttctgtgatc tgccctgatt aagatgaatt gtgaaattta catcaagcaa 4321
ttatcaaagc gggctgggtc ccatcagaac gacccacatc tttctgtggg tgtgaatgtc 4381
attaggtctt gcgctgaccc ctgagccccc atcactgccg cctgatgggg caaagaaaca 4441
aaaaacattt cttactcttc tgtgttttaa caaaagttta taaacaaaa taaatggcgc 4501
atatgttttc taaaaaaaaa aaaaaaa

GI: 385298687 (SEQ ID NO: 6)

ggccatggtc agcgtgaacg cgcccctcgg ggctccagtg gagagttctt acgacacgtc 61
cccatcagaa ggcaccaacc tcaacgcgcc caacagcctg ggtgtcagcg ccctgtgtgc 121
catctgcggg gaccgggcca cgggcaaaca ctacggtgcc tcgagctgtg acggctgcaa 181
gggcttcttc cggaggagcg tgcggaagaa ccacatgtac tcctgcagat ttagccggca 241
gtgcgtggtg gacaaagaca agaggaacca gtgccgctac tgcaggctca gaaatgctt 301
ccgggctggc atgaagaagg aagccgtcca gaatgagcgg gaccggatca gcactcgaag 361
gtcaagctat gaggacagca gcctgccctc catcaatgcg ctcctgcagg cggaggtcct 421
gtcccgacag atcacctccc ccgtctccgg gatcaacggc gacattcggg cgaagaagat 481
tgccagcatc gcagatgtgt gtgagtccat gaaggagcag ctgctggttc tcgttgagtg 541
ggccaagtac atccagcttt tctgcgagct ccccctggac gaccaggtgg ccctgctcag 601
agcccatgct ggcgagcacc tgctgctcgg agccaccaag agatccatgg tgttcaagga 661
```

FIG. 7A8

```
cgtgctgctc ctaggcaatg actacattgt ccctcggcac tgcccggagc tggcggagat 721
gagccgggtg tccatacgca tccttgacga gctggtgctg cccttccagg agctgcagat 781
cgatgacaat gagtatgcct acctcaaagc catcatcttc tttgacccag atgccaaggg 841
gctgagcgat ccagggaaga tcaagcggct gcgttcccag gtgcaggtga gcttggagga 901
ctacatcaac gaccgccagt atgactcgcg tggccgcttt ggagagctgc tgctgctgct 961
gcccaccttg cagagcatca cctggcagat gatcgagcag atccagttca tcaagctctt 1021
cggcatggcc aagattgaca acctgttgca ggagatgctg ctgggaggtc cgtgccaagc 1081
ccaggagggg cggggttgga gtggggactc cccaggagac aggcctcaca cagtgagctc 1141
accccctcagc tccttggctt ccccactgtg ccgctttggg caagttgctt aacctgtctg 1201
tgcctcagtt tcctcaccag aaaaatggga acaaggcaat ggtctatttg ttcaggcacc 1261
gagaacctag cacgtgccag tcactgttct aagtgctggc aattcagcaa agaacaagat 1321
ctttgccctc ggggaggctg tgtgtgtgtg agtatgtatg gatgcgtgga tatctgtgta 1381
tatgcccgta tgtgcgtgca tgtgtatata aagcctcaca ttttatgatt ttgaaataaa 1441
caggtaata
```

FIG. 7A9

GI: 31077207 (SEQ ID NO: 7)

```
mrlsktlvdm  dmadysaald  payttlefen  vqvltmgndt  spsegtnlna  pnslgvsalc  61
aicgdratgk  hygasscdgc  kgffrrsvrk  nhmyscrfsr  qcvvdkdkrn  qcrycrlkkc  121
fragmkkeav  qnerdristr  rssyedsslp  sinallqaev  lsrqitspvs  gingdirakk  181
iasiadvces  mkeqllvlve  wakyipafce  lplddqvall  rahagehlll  gatkrsmvfk  241
dvlllgndyi  vprhcpelae  msrvsirild  elvlpfqelq  iddneyaylk  aiiffdpdak  301
glsdpgkikr  lrsqvqvsle  dyindrqyds  rgrfgelll   lptlqsitwq  mieqiqfikl  361
fgmakidnll  qemllggsps  daphahhplh  phlmqehmgt  nvivantmpt  hlsngqmstp  421
etpqpsppgg  sgsepykllp  gavativkpl  saipqptitk  qevi
```

GI: 31077205 (SEQ ID NO: 8)

```
mrlsktlvdm  dmadysaald  payttlefen  vqvltmgndt  spsegtnlna  pnslgvsalc  61
aicgdratgk  hygasscdgc  kgffrrsvrk  nhmyscrfsr  qcvvdkdkrn  qcrycrlkkc  121
fragmkkeav  qnerdristr  rssyedsslp  sinallqaev  lsrqitspvs  gingdirakk  181
iasiadvces  mkeqllvlve  wakyipafce  lplddqvall  rahagehlll  gatkrsmvfk  241
dvlllgndyi  vprhcpelae  msrvsirild  elvlpfqelq  iddneyaylk  aiiffdpdak  301
glsdpgkikr  lrsqvqvsle  dyindrqyds  rgrfgelll   lptlqsitwq  mieqiqfikl  361
fgmakidnll  qemllggsps  daphahhplh  phlmqehmgt  nvivantmpt  hlsngqmcew  421
prprgqaatp  etpqpsppgg  sgsepykllp  gavativkpl  saipqptitk  qevi
```

GI: 31077209 (SEQ ID NO: 9)

```
mrlsktlvdm  dmadysaald  payttlefen  vqvltmgndt  spsegtnlna  pnslgvsalc  61
aicgdratgk  hygasscdgc  kgffrrsvrk  nhmyscrfsr  qcvvdkdkrn  qcrycrlkkc  121
fragmkkeav  qnerdristr  rssyedsslp  sinallqaev  lsrqitspvs  gingdirakk  181
iasiadvces  mkeqllvlve  wakyipafce  lplddqvall  rahagehlll  gatkrsmvfk  241
dvlllgndyi  vprhcpelae  msrvsirild  elvlpfqelq  iddneyaylk  aiiffdpdak  301
glsdpgkikr  lrsqvqvsle  dyindrqyds  rgrfgelll   lptlqsitwq  mieqiqfikl  361
fgmakidnll  qemllggpcq  aqegrgwsgd  spgdrphtvs  splsslaspl  crfgqva
```

GI: 71725339 (SEQ ID NO: 10)

```
mvsvnaplga  pvessydtsp  segtnlnapn  slgvsalcai  cgdratgkhy  gasscdgckg  61
ffrrsvrknh  myscrfsrqc  vvdkdkrnqc  ryclkkcfr   agmkkeavqn  erdristrrs  121
syedsslpsi  nallqaevls  rqitspvsgi  ngdirakkia  siadvcesmk  eqllvlvewa  181
kyipafcelp  lddqvallra  hagehlllga  tkrsmvfkdv  lllgndyivp  rhcpelaems  241
rvsirildel  vlpfqelqid  dneyaylkai  iffdpdakgl  sdpgkikrlr  sqvqvsledy  301
indrqydsrg  rfgellllp   tlqsitwqmi  eqiqfiklfg  makidnllqe  mllggspsda  361
phahhplhph  lmqehmgtnv  ivantmpthl  sngqmcewpr  prgqaatpet  pqpsppggsg  421
sepykllpga  vativkplsa  ipqptitkqe  vi
```

FIG. 7B1

GI: 71725341 (SEQ ID NO: 11)

```
mvsvnaplga pvessydtsp segtnlnapn slgvsalcai cgdratgkhy gasscdgckg 61
ffrrsvrknh myscrfsrqc vvdkdkrnqc rycrlkkcfr agmkkeavqn erdristrrs 121
syedsslpsi nallqaevls rqitspvsgi ngdirakkia siadvcesmk eqllvlvewa 181
kyipafcelp lddqvallra hagehlllga tkrsmvfkdv lllgndyivp rhcpelaems 241
rvsirildel vlpfqelqid dneyaylkai iffdpdakgl sdpgkikrlr sqvqvsledy 301
indrqydsrg rfgelllllp tlqsitwqmi eqiqfiklfg makidnllqe mllggspsda 361
phahhplhph lmqehmgtnv ivantmpthl sngqmstpet pqpsppggsg sepykllpga 421
vativkplsa ipqptitkqe vi
```

GI: 71725336 (SEQ ID NO: 12)

```
mvsvnaplga pvessydtsp segtnlnapn slgvsalcai cgdratgkhy gasscdgckg 61
ffrrsvrknh myscrfsrqc vvdkdkrnqc rycrlkkcfr agmkkeavqn erdristrrs 121
syedsslpsi nallqaevls rqitspvsgi ngdirakkia siadvcesmk eqllvlvewa 181
kyipafcelp lddqvallra hagehlllga tkrsmvfkdv lllgndyivp rhcpelaems 241
rvsirildel vlpfqelqid dneyaylkai iffdpdakgl sdpgkikrlr sqvqvsledy 301
indrqydsrg rfgelllllp tlqsitwqmi eqiqfiklfg makidnllqe mllggpcqaq 361
egrgwsgdsp gdrphtvssp lsslasplcr fgqva
```

FIG. 7B2

```
SEQUENCE LISTING

<160> NUMBER OF SEQ ID NOS: 80

<210> SEQ ID NO 1
<211> LENGTH: 4707
<212> TYPE: DNA
<213> ORGANISM: Homo sapiens

<400> SEQUENCE: 1
ggtttgaaag gaaggcagag agggcactgg gaggaggcag tgggagggcg gagggcgggg      60
gccttcgggg tgggcgccca gggtagggca ggtggccgcg gcgtggaggc agggagaatg     120
cgactctcca aaaccctcgt cgacatggac atggccgact acagtgctgc actggaccca     180
gcctacacca ccctggaatt tgagaatgtg caggtgttga cgatgggcaa tgacacgtcc     240
ccatcagaag gcaccaacct caacgcgccc aacagcctgg gtgtcagcgc cctgtgtgcc     300
atctgcgggg accgggccac gggcaaacac tacggtgcct cgagctgtga cggctgcaag     360
ggcttcttcc ggaggagcgt gcggaagaac cacatgtact cctgcagatt tagccggcag     420
tgcgtggtgg acaaagacaa gaggaaccag tgccgctact gcaggctcaa gaaatgcttc     480
cgggctggca tgaagaagga agccgtccag aatgagcggg accggatcag cactcgaagg     540
tcaagctatg aggacagcag cctgccctcc atcaatgcgc tcctgcaggc ggaggtcctg     600
tcccgacaga tcacctcccc cgtctccggg atcaacggcg acattcgggc gaagaagatt     660
gccagcatcg cagatgtgtg tgagtccatg aaggagcagc tgctggttct cgttgagtgg     720
gccaagtaca tcccagcttt ctgcgagctc ccctggacg accaggtggc cctgctcaga     780
gcccatgctg gcgagcacct gctgctcgga gccaccaaga gatccatggt gttcaaggac     840
gtgctgctcc taggcaatga ctacattgtc cctcggcact gcccggagct ggcggagatg     900
agccgggtgt ccatacgcat ccttgacgag ctggtgctgc ccttccagga gctgcagatc     960
gatgacaatg agtatgccta cctcaaagcc atcatcttct ttgacccaga tgccaagggg    1020
ctgagcgatc cagggaagat caagcggctg cgttcccagg tgcaggtgag cttggaggac    1080
tacatcaacg accgccagta tgactcgcgt ggccgctttg gagagctgct gctgctgctg    1140
cccaccttgc agagcatcac ctggcagatg atcgagcaga tccagttcat caagctcttc    1200
```

```
ggcatggcca agattgacaa cctgttgcag gagatgctgc tgggagggtc ccccagcgat   1260
gcaccccatg cccaccaccc cctgcaccct cacctgatgc aggaacatat gggaaccaac   1320
gtcatcgttg ccaacacaat gcccactcac ctcagcaacg acagatgtc caccctgag    1380 accccacagc cctcaccgcc aggtggctca gggtctgagc cctataagct cctgccggga   1440
gccgtcgcca caatcgtcaa gcccctctct gccatccccc agccgaccat caccaagcag   1500
gaagttatct agcaagccgc tggggcttgg gggctccact ggctccccccc agcccctaa   1560 gagagcacct ggtgatcacg tggtcacggc aaaggaagac gtgatgccag gaccagtccc   1620
agagcaggaa tggaaggat gaagggcccg agaacatggc ctaagggcca catcccactg    1680
ccacccttga cgccctgctc tggataacaa gactttgact tggggagacc tctactgcct   1740
tggacaactt ttctcatgtt gaagccactg ccttcacctt caccttcatc catgtccaac   1800
ccccgacttc atcccaaagg acagccgcct ggagatgact tgaggcctta cttaaaccca   1860
gctcccttct tccctagcct ggtgcttctc ctctcctagc ccctgtcatg gtgtccagac   1920
agagccctgt gaggctgggt ccaattgtgg cacttgggc accttgctcc tccttctgct    1980
gctgccccca cctctgctgc ctccctctgc tgtcaccttg ctcagccatc ccgtcttctc   2040
caacaccacc tctccagagg ccaaggaggc cttggaaacg attcccccag tcattctggg   2100
aacatgttgt aagcactgac tgggaccagg caccaggcag ggtctagaag ctgtggtga    2160 gggaagacgc ctttctcctc caacccaacc tcatcctcct tcttcaggga cttgggtggg   2220
tacttgggtg aggatccctg aaggccttca acccgagaaa acaaacccag gttggcgact   2280
gcaacaggaa cttggagtgg agaggaaaag catcagaaag aggcagacca tccaccaggc   2340
ctttgagaaa gggtagaatt ctggctggta gagcaggtga gatgggacat tccaaagaac   2400
agcctgagcc aaggcctagt ggtagtaaga atctagcaag aattgaggaa gaatggtgtg   2460
ggagagggat gatgaagaga gagagggcct gctggagagc atagggtctg gaacaccagg   2520
ctgaggtcct gatcagcttc aaggagtatg cagggagctg ggcttccaga aaatgaacac   2580
agcagttctg cagaggacgg gaggctggaa gctgggaggt caggtggggt ggatgatata   2640
atgcgggtga gagtaatgag gcttggggct ggagaggaca agatgggtaa accctcacat   2700
cagagtgaca tccaggagga ataagctccc agggcctgtc tcaagctctt ccttactccc   2760
aggcactgtc ttaaggcatc tgacatgcat catctcattt aatcctccct tcctccctat   2820
taacctagag attgttttg tttttttattc tcctcctccc tccccgccct cacccgcccc    2880
actccctcct aacctagaga ttgttacaga agctgaaatt gcgttctaag aggtgaagtg   2940
attttttttc tgaaactcac acaactagga agtggctgag tcaggacttg aacccaggtc   3000
tccctggatc agaacaggag ctcttaacta cagtggctga atagcttctc caaaggctcc   3060
ctgtgttctc accgtgatca agttgagggg cttccggctc ccttctacag cctcagaaac   3120
cagactcgtt cttctgggaa ccctgcccac tccaggacc aagattggcc tgaggctgca    3180
ctaaaattca cttagggtcg agcatcctgt ttgctgataa atattaagga gaattcatga   3240
ctcttgacag ctttttctctc ttcactcccc aagtcaaggg gaggggtggc aggggtctgt   3300
ttcctggaag tcaggctcat ctggcctgtt ggcatggggg tgggacagtg tgcacagtgt   3360
gggggcaggg gagggctaag caggcctggg tttgagggct gctccggaga ccgtcactcc   3420
aggtgcattc tggaagcatt agaccccagg atggagcgac cagcatgtca tccatgtgga   3480
atcttggtgg ctttgaggac attctggaaa atgccactga ccagtgtgaa caaaagggat   3540
```

-continued

| | |
|---|---|
| gtgttatggg gctggaggtg tgattaggta ggagggaaac tgttggaccg actcctgccc | 3600 |
| cctgctcaac actgacccct ctgagtggtt ggaggcagtg ccccagtgcc cagaaatccc | 3660 |
| accattagtg attgtttttt atgagaaaga ggcgtggaga agtattgggg caatgtgtca | 3720 |
| gggaggaatc accacatccc tacggcagtc ccagccaagc ccccaatccc agcggagact | 3780 |
| gtgccctgct cagagctccc aagccttccc ccaccacctc actcaagtgc ccctgaaatc | 3840 |
| cctgccagac ggctcagcct ggtctgcggt aaggcaggga ggctggaacc atttctgggc | 3900 |
| attgtggtca ttcccactgt gttcctccac ctcctccctc cagcgttgct cagacctctg | 3960 |
| tcttgggaga aaggttgaga taagaatgtc ccatggagtg ccgtgggcaa cagtggccct | 4020 |
| tcatgggaac aatctgttgg agcagggggt cagttctctg ctgggaatct accccttttct | 4080 |
| ggaggagaaa cccattccac cttaataact ttattgtaat gtgagaaaca caaaacaaag | 4140 |
| tttactttt tgactctaag ctgacatgat attagaaaat ctctcgctct cttttttttt | 4200 |
| tttttttttt tttttggcta cttgagttgt ggtcctaaaa cataaaatct gatggacaaa | 4260 |
| cagagggttg ctggggggac aagcgtgggc acaatttccc caccaagaca ccctgatctt | 4320 |
| caggcgggtc tcaggagctt ctaaaaatcc gcatggctct cctgagagtg gacagaggag | 4380 |
| aggagagggt cagaaatgaa cgctcttcta tttcttgtca ttaccaagcc aattactttt | 4440 |
| gccaaatttt tctgtgatct gccctgatta agatgaattg tgaaatttac atcaagcaat | 4500 |
| tatcaaagcg ggctgggtcc catcagaacg acccacatct ttctgtgggt gtgaatgtca | 4560 |
| ttaggtcttg cgctgacccc tgagccccca tcactgccgc ctgatggggc aaagaaacaa | 4620 |
| aaaacatttc ttactcttct gtgttttaac aaaagtttat aaaacaaaat aaatggcgca | 4680 |
| tatgttttct aaaaaaaaaa aaaaaaa | 4707 |

<210> SEQ ID NO 2
<211> LENGTH: 4737
<212> TYPE: DNA
<213> ORGANISM: Homo sapiens

<400> SEQUENCE: 2

| | |
|---|---|
| ggtttgaaag gaaggcagag agggcactgg gaggaggcag tgggagggcg gagggcgggg | 60 |
| gccttcgggg tgggcgccca gggtagggca ggtggccgcg gcgtggaggc agggagaatg | 120 |
| cgactctcca aaaccctcgt cgacatggac atggccgact acagtgctgc actggaccca | 180 |
| gcctacacca ccctggaatt tgagaatgtg caggtgttga cgatgggcaa tgacacgtcc | 240 |
| ccatcagaag gcaccaacct caacgcgccc aacagcctgg tgtcagcgc cctgtgtgcc | 300 |
| atctgcgggg accgggccac gggcaaacac tacggtgcct cgagctgtga cggctgcaag | 360 |
| ggcttcttcc ggaggagcgt gcggaagaac cacatgtact cctgcagatt tagccggcag | 420 |
| tgcgtggtgg acaaagacaa gaggaaccag tgccgctact gcaggctcaa gaaatgcttc | 480 |
| cgggctggca tgaagaagga agccgtccag aatgagcggg accggatcag cactcgaagg | 540 |
| tcaagctatg aggacagcag cctgcccctc atcaatgcgc tcctgcaggc ggaggtcctg | 600 |
| tcccgacaga tcacctcccc cgtctccggg atcaacggcg acattcgggc gaagaagatt | 660 |
| gccagcatcg cagatgtgtg tgagtccatg aaggagcagc tgctggttct cgttgagtgg | 720 |
| gccaagtaca tcccagcttt ctgcgagctc ccctggacg accaggtggc cctgctcaga | 780 |
| gcccatgctg gcgagcacct gctgctcgga gccaccaaga gatccatggt gttcaaggac | 840 |
| gtgctgctcc taggcaatga ctacattgtc cctcggcact gcccggagct ggcggagatg | 900 |
| agccgggtgt ccatacgcat ccttgacgag ctggtgctgc ccttccagga gctgcagatc | 960 |

```
gatgacaatg agtatgccta cctcaaagcc atcatcttct ttgacccaga tgccaagggg      1020
ctgagcgatc cagggaagat caagcggctg cgttcccagg tgcaggtgag cttggaggac      1080
tacatcaacg accgccagta tgactcgcgt ggccgctttg agagctgct gctgctgctg       1140 cccaccttgc agagcatcac ctggcagatg atcgagcaga tccagttcat caagctcttc      1200
ggcatggcca agattgacaa cctgttgcag agatgctgc tgggagggtc ccccagcgat       1260
gcaccccatg cccaccaccc cctgcaccct cacctgatgc aggaacatat gggaaccaac      1320
gtcatcgttg ccaacacaat gcccactcac ctcagcaacg acagatgtg tgagtggccc       1380 cgacccaggg gacaggcagc caccctgag accccacagc cctcaccgcc aggtggctca       1440
gggtctgagc cctataagct cctgccggga ccgtcgcca caatcgtcaa gccctctct        1500 gccatccccc agccgaccat caccaagcag gaagttatct agcaagccgc tggggcttgg      1560
gggctccact ggctcccccc agcccctaa gagagcacct ggtgatcacg tggtcacggc       1620
aaaggaagac gtgatgccag gaccagtccc agagcaggaa tgggaaggat gaagggcccg     1680
agaacatggc ctaagggcca catcccactg ccacccttga cgccctgctc tggataacaa      1740
gactttgact tggggagacc tctactgcct tggacaactt ttctcatgtt gaagccactg      1800
ccttcacctt caccttcatc catgtccaac ccccgacttc atcccaaagg acagccgcct      1860
ggagatgact tgaggcctta cttaaaccca gctcccttct tccctagcct ggtgcttctc      1920
ctctcctagc ccctgtcatg gtgtccagac agagccctgt gaggctgggt ccaattgtgg      1980
cacttggggc accttgctcc tccttctgct gctgcccca cctctgctgc ctccctctgc       2040
tgtcaccttg ctcagccatc ccgtcttctc caacaccacc tctccagagg ccaaggaggc      2100 cttgaaacg attcccccag tcattctggg aacatgttgt aagcactgac tgggaccagg      2160
caccaggcag ggtctagaag gctgtggtga gggaagacgc ctttctcctc caacccaacc      2220
tcatcctcct tcttcaggga cttgggtggg tacttgggtg aggatccctg aaggccttca     2280
acccgagaaa acaaacccag gttggcgact gcaacaggaa cttggagtgg agaggaaaag     2340
catcagaaag aggcagacca tccaccaggc ctttgagaaa gggtagaatt ctggctggta     2400
gagcaggtga gatgggacat tccaaagaac agcctgagcc aaggcctagt ggtagtaaga     2460
atctagcaag aattgaggaa gaatggtgtg ggagagggat gatgaagaga gagagggcct    2520
gctggagagc atagggtctg gaacaccagg ctgaggtcct gatcagcttc aaggagtatg     2580
cagggagctg ggcttccaga aaatgaacac agcagttctg cagaggacgg gaggctggaa     2640
gctgggaggt caggtggggt ggatgatata atgcgggtga gagtaatgag gcttggggct     2700
ggagaggaca agatgggtaa accctcacat cagagtgaca tccaggagga ataagctccc     2760
agggcctgtc tcaagctctt ccttactccc aggcactgtc ttaaggcatc tgacatgcat     2820
catctcattt aatcctccct tcctcccta taacctagag attgtttttg ttttttattc      2880
tcctcctccc tccccgccct caccgcccc actccctcct aacctagaga ttgttacaga      2940
agctgaaatt gcgttctaag aggtgaagtg attttttttc tgaaactcac acaactagga     3000
agtggctgag tcaggacttg aacccaggtc tccctggatc agaacaggag ctcttaacta     3060
cagtggctga atagcttctc caaaggctcc ctgtgttctc accgtgatca agttgagggg     3120
cttccggctc ccttctacag cctcagaaac cagactcgtt cttctgggaa ccctgcccac     3180
tcccaggacc aagattggcc tgaggctgca ctaaaattca cttagggtcg agcatcctgt     3240
ttgctgataa atattaagga gaattcatga ctcttgacag cttttctctc ttcactcccc     3300
```

```
aagtcaaggg gaggggtggc aggggtctgt ttcctggaag tcaggctcat ctggcctgtt    3360
ggcatggggg tgggacagtg tgcacagtgt gggggcaggg gagggctaag caggcctggg    3420
tttgagggct gctccggaga ccgtcactcc aggtgcattc tggaagcatt agaccccagg    3480
atggagcgac cagcatgtca tccatgtgga atcttggtgg cttttgaggac attctggaaa   3540
atgccactga ccagtgtgaa caaaagggat gtgttatggg gctggaggtg tgattaggta    3600
ggagggaaac tgttggaccg actcctgccc cctgctcaac actgacccct ctgagtggtt    3660
ggaggcagtg ccccagtgcc cagaaatccc accattagtg attgtttttt atgagaaaga    3720
ggcgtggaga agtattgggg caatgtgtca gggaggaatc accacatccc tacggcagtc    3780
ccagccaagc ccccaatccc agcggagact gtgccctgct cagagctccc aagccttccc    3840
ccaccacctc actcaagtgc ccctgaaatc cctgccagac ggctcagcct ggtctgcggt    3900
aaggcaggga ggctggaacc atttctgggc attgtggtca ttcccactgt gttcctccac    3960
ctcctccctc cagcgttgct cagacctctg tcttgggaga aggttgaga taagaatgtc     4020
ccatggagtg ccgtgggcaa cagtggccct tcatgggaac aatctgttgg agcagggggt    4080
cagttctctg ctgggaatct accccttct ggaggagaaa cccattccac cttaataact     4140
ttattgtaat gtgagaaaca caaaacaaag tttactttt tgactctaag ctgacatgat     4200
attagaaaat ctctcgctct cttttttttt tttttttttt ttttggcta cttgagttgt     4260
ggtcctaaaa cataaaatct gatggacaaa cagagggttg ctgggggggac aagcgtgggc   4320
acaatttccc caccaagaca ccctgatctt caggcgggtc tcaggagctt ctaaaaatcc    4380
gcatggctct cctgagagtg gacagaggag aggagagggt cagaaatgaa cgctcttcta    4440
tttcttgtca ttaccaagcc aattactttt gccaattttt tctgtgatct gccctgatta    4500
agatgaattg tgaaatttac atcaagcaat tatcaaagcg ggctgggtcc catcagaacg    4560
acccacatct ttctgtgggt gtgaatgtca ttaggtcttg cgctgacccc tgagccccca    4620
tcactgccgc ctgatggggc aaagaaacaa aaaacatttc ttactcttct gtgttttaac    4680
aaaagtttat aaaacaaaat aaatggcgca tatgtttct aaaaaaaaaa aaaaaaa       4737
```

<210> SEQ ID NO 3
<211> LENGTH: 1628
<212> TYPE: DNA
<213> ORGANISM: Homo sapiens

<400> SEQUENCE: 3

```
ggtttgaaag gaaggcagag agggcactgg gaggaggcag tgggagggcg gagggcgggg     60
gccttcgggg tgggcgccca gggtagggca ggtggccgcg gcgtggaggc agggagaatg    120
cgactctcca aaaccctcgt cgacatggac atggccgact acagtgctgc actggaccca    180
gcctacacca ccctggaatt tgagaatgtg caggtgttga cgatgggcaa tgacacgtcc    240
ccatcagaag gcaccaacct caacgcgccc aacagcctgg tgtcagcgc cctgtgtgcc    300
atctgcgggg accgggccac gggcaaacac tacggtgcct cgagctgtga cggctgcaag    360
ggcttcttcc ggaggagcgt gcggaagaac cacatgtact cctgcagatt tagccggcag    420
tgcgtggtgg acaaagacaa gaggaaccag tgccgctact gcaggctcaa gaaatgcttc    480
cgggctggca tgaagaagga agccgtccag aatgagcggg accggatcag cactcgaagg    540
tcaagctatg aggacagcag cctgccctcc atcaatgcgc cctgcaggc ggaggtcctg     600
tcccgacaga tcacctcccc cgtctcgggg atcaacggcg acattcgggc gaagaagatt    660
gccagcatcg cagatgtgtg tgagtccatg aaggagcagc tgctggttct cgttgagtgg    720
```

-continued

| | |
|---|---|
| gccaagtaca tcccagcttt ctgcgagctc cccctggacg accaggtggc cctgctcaga | 780 |
| gcccatgctg gcgagcacct gctgctcgga gccaccaaga gatccatggt gttcaaggac | 840 |
| gtgctgctcc taggcaatga ctacattgtc cctcggcact gcccggagct ggcggagatg | 900 |
| agccgggtgt ccatacgcat ccttgacgag ctggtgctgc ccttccagga gctgcagatc | 960 |
| gatgacaatg agtatgccta cctcaaagcc atcatcttct ttgacccaga tgccaagggg | 1020 |
| ctgagcgatc cagggaagat caagcggctg cgttcccagg tgcaggtgag cttggaggac | 1080 |
| tacatcaacg accgccagta tgactcgcgt ggccgctttg agagctgct gctgctgctg | 1140 |
| cccaccttgc agagcatcac ctggcagatg atcgagcaga tccagttcat caagctcttc | 1200 |
| ggcatggcca agattgacaa cctgttgcag gagatgctgc tgggaggtcc gtgccaagcc | 1260 |
| caggaggggc ggggttggag tggggactcc ccaggagaca ggcctcacac agtgagctca | 1320 |
| cccctcagct ccttggcttc ccactgtgc cgctttgggc aagttgctta acctgtctgt | 1380 |
| gcctcagttt cctcaccaga aaatgggaa caaggcaatg gtctatttgt tcaggcaccg | 1440 |
| agaacctagc acgtgccagt cactgttcta agtgctggca attcagcaaa gaacaagatc | 1500 |
| tttgccctcg gggaggctgt gtgtgtgtga gtatgtatgg atgcgtggat atctgtgtat | 1560 |
| atgcccgtat gtgcgtgcat gtgtatataa agcctcacat tttatgattt tgaaataaac | 1620 |
| aggtaata | 1628 |

<210> SEQ ID NO 4
<211> LENGTH: 4558
<212> TYPE: DNA
<213> ORGANISM: Homo sapiens

<400> SEQUENCE: 4

| | |
|---|---|
| ggccatggtc agcgtgaacg cgcccctcgg ggctccagtg gagagttctt acgacacgtc | 60 |
| cccatcagaa ggcaccaacc tcaacgcgcc caacagcctg ggtgtcagcg ccctgtgtgc | 120 |
| catctgcggg gaccgggcca cgggcaaaca ctacggtgcc tcgagctgtg acggctgcaa | 180 |
| gggcttcttc cggaggagcg tgcggaagaa ccacatgtac tcctgcagat ttagccggca | 240 |
| gtgcgtggtg gacaaagaca agaggaacca gtgccgctac tgcaggctca gaaatgctt | 300 |
| ccgggctggc atgaagaagg aagccgtcca gaatgagcgg gaccggatca gcactcgaag | 360 |
| gtcaagctat gaggacagca gcctgccctc catcaatgcg ctcctgcagg cggaggtcct | 420 |
| gtcccgacag atcacctccc ccgtctccgg gatcaacggc gacattcggg cgaagaagat | 480 |
| tgccagcatc gcagatgtgt gtgagtccat gaaggagcag ctgctggttc tcgttgagtg | 540 |
| ggccaagtac atcccagctt ctgcgagctc ccccctggac gaccaggtgg ccctgctcag | 600 |
| agcccatgct ggcgagcacc tgctgctcgg agccaccaag agatccatgg tgttcaagga | 660 |
| cgtgctgctc ctaggcaatg actacattgt ccctcggcac tgcccggagc tggcggagat | 720 |
| gagccgggtg tccatacgca tccttgacga gctggtgctg ccttccagg agctgcagat | 780 |
| cgatgacaat gagtatgcct acctcaaagc catcatcttc tttgacccag atgccaaggg | 840 |
| gctgagcgat ccagggaaga tcaagcggct gcgttcccag gtgcaggtga gcttggagga | 900 |
| ctacatcaac gaccgccagt atgactcgcg tggccgcttt ggagagctgc tgctgctgct | 960 |
| gcccaccttg cagagcatca cctggcagat gatcgagcag atccagttca tcaagctctt | 1020 |
| cggcatggcc aagattgaca acctgttgca ggagatgctg ctgggagggt ccccagcga | 1080 |
| tgcaccccat gcccaccacc ccctgcaccc tcacctgatg caggaacata tgggaaccaa | 1140 |

```
cgtcatcgtt gccaacacaa tgcccactca cctcagcaac ggacagatgt gtgagtggcc      1200
ccgacccagg ggacaggcag ccaccgctga gaccccacag ccctcaccgc caggtggctc      1260
agggtctgag ccctataagc tcctgccggg agccgtcgcc acaatcgtca agcccctctc      1320
tgccatcccc cagccgacca tcaccaagca ggaagttatc tagcaagccg ctggggcttg      1380
ggggctccac tggctccccc cagcccccta agagagcacc tggtgatcac gtggtcacgg      1440
caaaggaaga cgtgatgcca ggaccagtcc cagagcagga atgggaagga tgaagggccc      1500
gagaacatgg cctaagggcc acatcccact gccacccttg acgccctgct ctggataaca      1560
agactttgac ttggggagac ctctactgcc ttggacaact tttctcatgt tgaagccact      1620
gccttcacct tcaccttcat ccatgtccaa cccccgactt catcccaaag gacagccgcc      1680
tggagatgac ttgaggcctt acttaaaccc agctcccttc ttccctagcc tggtgcttct      1740
cctctcctag cccctgtcat ggtgtccaga cagagccctg tgaggctggg tccaattgtg      1800
gcacttgggg caccttgctc ctccttctgc tgctgccccc acctctgctg cctccctctg      1860
ctgtcacctt gctcagccat cccgtcttct ccaacaccac ctctccagag gccaaggagg      1920
ccttggaaac gattccccca gtcattctgg gaacatgttg taagcactga ctgggaccag      1980
gcaccaggca gggtctagaa ggctgtggtg agggaagacg cctttctcct ccaacccaac      2040
ctcatcctcc ttcttcaggg acttgggtgg gtacttgggt gaggatccct gaaggccttc      2100
aacccgagaa aacaaaccca ggttggcgac tgcaacagga acttggagtg agaggaaaa      2160 gcatcagaaa gaggcagacc atccaccagg cctttgagaa agggtagaat tctggctggt      2220
agagcaggtg agatgggaca ttccaaagaa cagcctgagc caaggcctag tggtagtaag      2280
aatctagcaa gaattgagga agaatggtgt gggagaggga tgatgaagag agagagggcc      2340
tgctggagag catagggtct ggaacaccag gctgaggtcc tgatcagctt caaggagtat      2400
gcagggagct gggcttccag aaaatgaaca cagcagttct gcagaggacg ggaggctgga      2460
agctgggagg tcaggtgggg tggatgatat aatgcgggtg agagtaatga gcttggggc       2520 tggagaggac aagatgggta aaccctcaca tcagagtgac atccaggagg aataagctcc      2580
cagggcctgt ctcaagctct tccttactcc caggcactgt cttaaggcat ctgacatgca      2640
tcatctcatt taatcctccc ttcctcccta ttaacctaga gattgttttt gttttttatt      2700
ctcctcctcc ctccccgccc tcacccgccc cactccctcc taacctagag attgttacag      2760
aagctgaaat tgcgttctaa gaggtgaagt gatttttttt ctgaaactca cacaactagg      2820
aagtggctga gtcaggactt gaacccaggt ctccctggat cagaacagga gctcttaact      2880
acagtggctg aatagcttct ccaaaggctc cctgtgttct caccgtgatc aagttgaggg      2940
gcttccggct cccttctaca gcctcagaaa ccagactcgt tcttctggga accctgccca      3000
ctcccaggac caagattggc ctgaggctgc actaaaattc acttagggtc gagcatcctg      3060
tttgctgata aatattaagg agaattcatg actcttgaca gcttttctct cttcactccc      3120
caagtcaagg ggaggggtgg cagggtctgt tttcctggaa gtcaggctca tctggcctgt      3180
tggcatgggg gtgggacagt gtgcacagtg tgggggcagg ggagggctaa gcaggcctgg      3240
gtttgagggc tgctccggag accgtcactc caggtgcatt ctggaagcat tagacccag       3300 gatggagcga ccagcatgtc atccatgtgg aatcttggtg gctttgagga cattctggaa      3360
aatgccactg accagtgtga acaaagggga tgtgttatgg ggctggaggt gtgattaggt      3420
aggagggaaa ctgttggacc gactcctgcc ccctgctcaa cactgacccc tctgagtggt      3480
tggaggcagt gccccagtgc ccagaaatcc caccattagt gattgttttt tatgagaaag      3540
```

-continued

```
aggcgtggag aagtattggg gcaatgtgtc agggaggaat caccacatcc ctacggcagt    3600
cccagccaag cccccaatcc cagcggagac tgtgccctgc tcagagctcc caagccttcc    3660
cccaccacct cactcaagtg cccctgaaat ccctgccaga cggctcagcc tggtctgcgg    3720
taaggcaggg aggctggaac catttctggg cattgtggtc attcccactg tgttcctcca    3780
cctcctccct ccagcgttgc tcagacctct gtcttgggag aaaggttgag ataagaatgt    3840
cccatggagt gccgtgggca acagtggccc ttcatgggaa caatctgttg gagcagggag    3900
tcagttctct gctgggaatc tacccctttc tggaggagaa acccattcca ccttaataac    3960
tttattgtaa tgtgagaaac acaaaacaaa gttttacttttt ttgactctaa gctgacatga    4020
tattagaaaa tctctcgctc tctttttttt ttttttttt ttttttggct acttgagttg    4080
tggtcctaaa acataaaatc tgatggacaa acagagggtt gctgggggga caagcgtggg    4140
cacaatttcc ccaccaagac accctgatct tcaggcgggt ctcaggagct tctaaaaatc    4200
cgcatggctc tcctgagagt ggacagagga gaggagaggg tcagaaatga acgctcttct    4260
atttcttgtc attaccaagc caattacttt tgccaaattt ttctgtgatc tgccctgatt    4320
aagatgaatt gtgaaattta catcaagcaa ttatcaaagc gggctgggtc ccatcagaac    4380
gacccacatc tttctgtggg tgtgaatgtc attaggtctt gcgctgaccc ctgagccccc    4440
atcactgccg cctgatgggg caaagaaaca aaaaacattt cttactcttc tgtgttttaa    4500
caaaagttta taaacaaaa taaatggcgc atatgttttc taaaaaaaaa aaaaaaa       4558
```

<210> SEQ ID NO 5
<211> LENGTH: 4528
<212> TYPE: DNA
<213> ORGANISM: Homo sapiens

<400> SEQUENCE: 5

```
ggccatggtc agcgtgaacg cgcccctcgg ggctccagtg gagagttctt acgacacgtc      60
cccatcagaa ggcaccaacc tcaacgcgcc caacagcctg ggtgtcagcg ccctgtgtgc     120
catctgcggg gaccgggcca cgggcaaaca ctacggtgcc tcgagctgtg acggctgcaa     180
gggcttcttc cggaggagcg tgcggaagaa ccacatgtac tcctgcagat ttagccggca     240
gtgcgtggtg gacaaagaca agaggaacca gtgccgctac tgcaggctca agaaatgctt     300
ccgggctggc atgaagaagg aagccgtcca gaatgagcgg gaccggatca gcactcgaag     360
gtcaagctat gaggacagca gcctgccctc catcaatgcg ctcctgcagg cggaggtcct     420
gtcccgacag atcacctccc ccgtctccgg atcaacggc gacattcggg cgaagaagat     480
tgccagcatc gcagatgtgt gtgagtccat gaaggagcag ctgctggttc tcgttgagtg     540
ggccaagtac atcccagctt tctgcgagct cccctggac gaccaggtgg ccctgctcag     600
agcccatgct ggcgagcacc tgctgctcgg agccaccaag agatccatgg tgttcaagga     660
cgtgctgctc ctaggcaatg actacattgt ccctcggcac tgcccggagc tggcggagat     720
gagccgggtg tccatacgca tccttgacga gctggtgctg cccttccagg agctgcagat     780
cgatgacaat gagtatgcct acctcaaagc catcatcttc tttgacccag atgccaaggg     840
gctgagcgat ccaggaaga tcaagcggct gcgttcccag gtgcaggtga gcttggagga     900
ctacatcaac gaccgccagt atgactcgcg tggccgcttt ggagagctgc tgctgctgct     960
gcccaccttg cagagcatca cctgcagat gatcgagcag atccagttca tcaagctctt    1020
cggcatggcc aagattgaca acctgttgca ggagatgctg ctgggagggt cccccagcga    1080
```

```
tgcaccccat gcccaccacc ccctgcaccc tcacctgatg caggaacata tgggaaccaa    1140
cgtcatcgtt gccaacacaa tgcccactca cctcagcaac ggacagatgt ccacccctga    1200
gaccccacag ccctcaccgc caggtggctc agggtctgag ccctataagc tcctgccggg    1260
agccgtcgcc acaatcgtca agccctctc tgccatcccc cagccgacca tcaccaagca    1320
ggaagttatc tagcaagccg ctggggcttg ggggctccac tggctccccc cagccccta    1380 agagagcacc tggtgatcac gtggtcacgg caaaggaaga cgtgatgcca ggaccagtcc    1440
cagagcagga atgggaagga tgaagggccc gagaacatgg cctaagggcc catcccact    1500 gccacccttg acgccctgct ctggataaca agactttgac ttggggagac ctctactgcc    1560
ttggacaact tttctcatgt tgaagccact gccttcacct tcaccttcat ccatgtccaa    1620
cccccgactt catcccaaag gacagccgcc tggagatgac ttgaggcctt acttaaaccc    1680
agctcccttc ttccctagcc tggtgcttct cctctcctag cccctgtcat ggtgtccaga    1740
cagagccctg tgaggctggg tccaattgtg gcacttgggg caccttgctc ctccttctgc    1800
tgctgccccc acctctgctg cctccctctg ctgtcacctt gctcagccat ccgtcttct     1860 ccaacaccac ctctccagag gccaaggagg ccttggaaac gattccccca gtcattctgg    1920
gaacatgttg taagcactga ctgggaccag gcaccaggca gggtctagaa ggctgtggtg    1980
agggaagacg cctttctcct ccaacccaac ctcatcctcc ttcttcaggg acttgggtgg    2040
gtacttgggt gaggatccct gaaggccttc aacccgagaa aacaaaccca ggttggcgac    2100
tgcaacagga acttggagtg gagaggaaaa gcatcagaaa gaggcagacc atccaccagg    2160
cctttgagaa agggtagaat tctgctggt agagcaggtg agatgggaca ttccaaagaa    2220
cagcctgagc caaggcctag tggtagtaag aatctagcaa gaattgagga agaatggtgt    2280
gggagaggga tgatgaagag agagagggcc tgctggagag catagggtct ggaacaccag    2340
gctgaggtcc tgatcagctt caaggagtat gcagggagct gggcttccag aaaatgaaca    2400
cagcagttct gcagaggacg ggaggctgga agctgggagg tcaggtgggg tggatgatat    2460
aatgcgggtg agagtaatga ggcttggggc tggagaggac aagatgggta aaccctcaca    2520
tcagagtgac atccaggagg aataagctcc caggcctgt ctcaagctct tccttactcc     2580
caggcactgt cttaaggcat ctgacatgca tcatctcatt taatcctccc ttcctcccta    2640
ttaacctaga gattgttttt gtttttatt ctcctcctcc ctcccgccc tcaccccgccc     2700 cactccctcc taacctagag attgttacag aagctgaaat tgcgttctaa gaggtgaagt    2760
gatttttttt ctgaaaactca cacaactagg aagtggctga gtcaggactt gaacccaggt   2820
ctccctggat cagaacagga gctcttaact acagtggctg aatagcttct ccaaaggctc    2880
cctgtgttct caccgtgatc aagttgaggg gcttccggct cccttctaca gcctcagaaa    2940
ccagactcgt tcttctggga accctgccca ctcccaggac caagattggc ctgaggctgc    3000
actaaaattc acttagggtc gagcatcctg tttgctgata aatattaagg agaattcatg    3060
actcttgaca gctttctctc ttcactccc caagtcaagg ggaggggtgg cagggtctg      3120 tttcctggaa gtcaggctca tctggcctgt tggcatgggg gtgggacagt gtgcacagtg    3180
tgggggcagg ggagggctaa gcaggcctgg gtttgagggc tgctccggag accgtcactc    3240
caggtgcatt ctggaagcat tagaccccag gatggagcga ccagcatgtc atccatgtgg    3300
aatcttggtg gctttgagga cattctggaa aatgccactg accagtgtga acaaagggga    3360
tgtgttatgg ggctggaggt gtgattaggt aggagggaaa ctgttggacc gactcctgcc    3420
ccctgctcaa cactgacccc tctgagtggt tggaggcagt gccccagtgc ccagaaatcc    3480
```

```
caccattagt gattgttttt tatgagaaag aggcgtggag aagtattggg gcaatgtgtc    3540
agggaggaat caccacatcc ctacggcagt cccagccaag cccccaatcc cagcggagac    3600
tgtgccctgc tcagagctcc caagccttcc cccaccacct cactcaagtg cccctgaaat    3660
ccctgccaga cggctcagcc tggtctgcgg taaggcaggg aggctggaac catttctggg    3720
cattgtggtc attcccactg tgttcctcca cctcctccct ccagcgttgc tcagacctct    3780
gtcttgggag aaaggttgag ataagaatgt cccatggagt gccgtgggca acagtggccc    3840
ttcatgggaa caatctgttg gagcaggggg tcagttctct gctgggaatc tacccctttc    3900
tggaggagaa acccattcca ccttaataac tttattgtaa tgtgagaaac acaaaacaaa    3960
gtttactttt ttgactctaa gctgacatga tattagaaaa tctctcgctc tcttttttt     4020 ttttttttt  tttttggct acttgagttg tggtcctaaa acataaaatc tgatggacaa    4080
acagagggtt gctgggggga caagcgtggg cacaatttcc ccaccaagac accctgatct    4140
tcaggcgggt ctcaggagct tctaaaaatc cgcatggctc tcctgagagt ggacagagga    4200
gaggagaggg tcagaaatga acgctcttct atttcttgtc attaccaagc caattacttt    4260
tgccaaattt ttctgtgatc tgccctgatt aagatgaatt gtgaaattta catcaagcaa    4320
ttatcaaagc gggctgggtc ccatcagaac gacccacatc tttctgtggg tgtgaatgtc    4380
attaggtctt gcgctgaccc ctgagccccc atcactgccg cctgatgggg caaagaaaca    4440
aaaaacattt cttactcttc tgtgttttaa caaaagttta taaaacaaaa taaatggcgc    4500
atatgttttc taaaaaaaaa aaaaaaa                                        4528

<210> SEQ ID NO 6
<211> LENGTH: 1449
<212> TYPE: DNA
<213> ORGANISM: Homo sapiens

<400> SEQUENCE: 6
ggccatggtc agcgtgaacg cgcccctcgg ggctccagtg gagagttctt acgacacgtc      60
cccatcagaa ggcaccaacc tcaacgcgcc caacagcctg ggtgtcagcg ccctgtgtgc     120
catctgcggg gaccgggcca cggcaaaaca ctacggtgcc tcgagctgtg acggctgcaa     180
gggcttcttc cggaggagcg tgcggaagaa ccacatgtac tcctgcagat ttagccggca     240
gtgcgtggtg gacaaagaca agaggaacca gtgccgctac tgcaggctca gaaatgcttt     300
ccgggctggc atgaagaagg aagccgtcca gaatgagcgg gaccggatca gcactcgaag     360
gtcaagctat gaggacagca gcctgccctc catcaatgcg ctcctgcagg cggaggtcct     420
gtcccgacag atcacctccc ccgtctccgg gatcaacggc gacattcggg cgaagaagat     480
tgccagcatc gcagatgtgt gtgagtccat gaaggagcga ctgctggttc tcgttgagtg     540
ggccaagtac atcccagctt ctgcgagctc ccccctggac gaccaggtgg ccctgctcag     600
agcccatgct ggcgagcacc tgctgctcgg agccaccaag agatccatgg tgttcaagga     660
cgtgctgctc ctaggcaatg actacattgt ccctcggcac tgcccggagc tggcggagat     720
gagccgggtg tccatacgca tccttgacga gctggtgctg cccttccagg agctgcagat     780
cgatgacaat gagtatgcct acctcaaagc catcatcttc tttgacccag atgccaaggg     840
gctgagcgat ccagggaaga tcaagcggct gcgttcccag gtgcaggtga gcttggagga     900
ctacatcaac gaccgccagt atgactcgcg tggccgcttt ggagctgctg ctgctgctgct    960 gcccaccttg cagagcatca cctggcagat gatcgagcag atccagttca tcaagctctt    1020
```

```
cggcatggcc aagattgaca acctgttgca ggagatgctg ctgggaggtc cgtgccaagc    1080
ccaggagggg cggggttgga gtggggactc cccaggagac aggcctcaca cagtgagctc    1140 accccctcagc tccttggctt ccccactgtg ccgctttggg caagttgctt aacctgtctg    1200
tgcctcagtt tcctcaccag aaaaatggga acaaggcaat ggtctatttg ttcaggcacc    1260
gagaacctag cacgtgccag tcactgttct aagtgctggc aattcagcaa agaacaagat    1320
ctttgccctc ggggaggctg tgtgtgtgtg agtatgtatg gatgcgtgga tatctgtgta    1380
tatgcccgta tgtgcgtgca tgtgtatata aagcctcaca ttttatgatt ttgaaataaa    1440
caggtaata                                                            1449
```

<210> SEQ ID NO 7
<211> LENGTH: 464
<212> TYPE: PRT
<213> ORGANISM: Homo sapiens

<400> SEQUENCE: 7

```
Met Arg Leu Ser Lys Thr Leu Val Asp Met Asp Met Ala Asp Tyr Ser
1               5                   10                  15

Ala Ala Leu Asp Pro Ala Tyr Thr Thr Leu Glu Phe Glu Asn Val Gln
            20                  25                  30

Val Leu Thr Met Gly Asn Asp Thr Ser Pro Ser Glu Gly Thr Asn Leu
        35                  40                  45

Asn Ala Pro Asn Ser Leu Gly Val Ser Ala Leu Cys Ala Ile Cys Gly
    50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
                85                  90                  95

Arg Phe Ser Arg Gln Cys Val Val Asp Lys Asp Lys Arg Asn Gln Cys
            100                 105                 110

Arg Tyr Cys Arg Leu Lys Lys Cys Phe Arg Ala Gly Met Lys Lys Glu
        115                 120                 125

Ala Val Gln Asn Glu Arg Asp Arg Ile Ser Thr Arg Arg Ser Ser Tyr
    130                 135                 140

Glu Asp Ser Ser Leu Pro Ser Ile Asn Ala Leu Leu Gln Ala Glu Val
145                 150                 155                 160

Leu Ser Arg Gln Ile Thr Ser Pro Val Ser Gly Ile Asn Gly Asp Ile
                165                 170                 175

Arg Ala Lys Lys Ile Ala Ser Ile Ala Asp Val Cys Glu Ser Met Lys
            180                 185                 190

Glu Gln Leu Leu Val Leu Val Glu Trp Ala Lys Tyr Ile Pro Ala Phe
        195                 200                 205

Cys Glu Leu Pro Leu Asp Asp Gln Val Ala Leu Leu Arg Ala His Ala
    210                 215                 220

Gly Glu His Leu Leu Leu Gly Ala Thr Lys Arg Ser Met Val Phe Lys
225                 230                 235                 240

Asp Val Leu Leu Leu Gly Asn Asp Tyr Ile Val Pro Arg His Cys Pro
                245                 250                 255

Glu Leu Ala Glu Met Ser Arg Val Ser Ile Arg Ile Leu Asp Glu Leu
            260                 265                 270

Val Leu Pro Phe Gln Glu Leu Gln Ile Asp Asp Asn Glu Tyr Ala Tyr
        275                 280                 285

Leu Lys Ala Ile Ile Phe Phe Asp Pro Asp Ala Lys Gly Leu Ser Asp
```

```
            290                 295                 300
Pro Gly Lys Ile Lys Arg Leu Arg Ser Gln Val Gln Val Ser Leu Glu
305                 310                 315                 320

Asp Tyr Ile Asn Asp Arg Gln Tyr Asp Ser Arg Gly Arg Phe Gly Glu
                325                 330                 335

Leu Leu Leu Leu Leu Pro Thr Leu Gln Ser Ile Thr Trp Gln Met Ile
                340                 345                 350

Glu Gln Ile Gln Phe Ile Lys Leu Phe Gly Met Ala Lys Ile Asp Asn
            355                 360                 365

Leu Leu Gln Glu Met Leu Leu Gly Gly Ser Pro Ser Asp Ala Pro His
        370                 375                 380

Ala His His Pro Leu His Pro His Leu Met Gln Glu His Met Gly Thr
385                 390                 395                 400

Asn Val Ile Val Ala Asn Thr Met Pro Thr His Leu Ser Asn Gly Gln
                405                 410                 415

Met Ser Thr Pro Glu Thr Pro Gln Pro Ser Pro Pro Gly Gly Ser Gly
                420                 425                 430

Ser Glu Pro Tyr Lys Leu Leu Pro Gly Ala Val Ala Thr Ile Val Lys
            435                 440                 445

Pro Leu Ser Ala Ile Pro Gln Pro Thr Ile Thr Lys Gln Glu Val Ile
        450                 455                 460
```

<210> SEQ ID NO 8
<211> LENGTH: 474
<212> TYPE: PRT
<213> ORGANISM: Homo sapiens

<400> SEQUENCE: 8

```
Met Arg Leu Ser Lys Thr Leu Val Asp Met Asp Met Ala Asp Tyr Ser
1               5                   10                  15

Ala Ala Leu Asp Pro Ala Tyr Thr Thr Leu Glu Phe Glu Asn Val Gln
            20                  25                  30

Val Leu Thr Met Gly Asn Asp Thr Ser Pro Ser Glu Gly Thr Asn Leu
        35                  40                  45

Asn Ala Pro Asn Ser Leu Gly Val Ser Ala Leu Cys Ala Ile Cys Gly
    50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
                85                  90                  95

Arg Phe Ser Arg Gln Cys Val Val Asp Lys Asp Lys Arg Asn Gln Cys
            100                 105                 110

Arg Tyr Cys Arg Leu Lys Lys Cys Phe Arg Ala Gly Met Lys Lys Glu
        115                 120                 125

Ala Val Gln Asn Glu Arg Asp Arg Ile Ser Thr Arg Arg Ser Ser Tyr
    130                 135                 140

Glu Asp Ser Ser Leu Pro Ser Ile Asn Ala Leu Leu Gln Ala Glu Val
145                 150                 155                 160

Leu Ser Arg Gln Ile Thr Ser Pro Val Ser Gly Ile Asn Gly Asp Ile
                165                 170                 175

Arg Ala Lys Lys Ile Ala Ser Ile Ala Asp Val Cys Glu Ser Met Lys
            180                 185                 190

Glu Gln Leu Leu Val Leu Val Glu Trp Ala Lys Tyr Ile Pro Ala Phe
        195                 200                 205
```

Cys Glu Leu Pro Leu Asp Asp Gln Val Ala Leu Leu Arg Ala His Ala
            210                 215                 220

Gly Glu His Leu Leu Gly Ala Thr Lys Arg Ser Met Val Phe Lys
225                 230                 235                 240

Asp Val Leu Leu Gly Asn Asp Tyr Ile Val Pro Arg His Cys Pro
                245                 250                 255

Glu Leu Ala Glu Met Ser Arg Val Ser Ile Arg Ile Leu Asp Glu Leu
            260                 265                 270

Val Leu Pro Phe Gln Glu Leu Gln Ile Asp Asp Asn Glu Tyr Ala Tyr
                275                 280                 285

Leu Lys Ala Ile Ile Phe Phe Asp Pro Asp Ala Lys Gly Leu Ser Asp
            290                 295                 300

Pro Gly Lys Ile Lys Arg Leu Arg Ser Gln Val Gln Val Ser Leu Glu
305                 310                 315                 320

Asp Tyr Ile Asn Asp Arg Gln Tyr Asp Ser Arg Gly Arg Phe Gly Glu
                325                 330                 335

Leu Leu Leu Leu Leu Pro Thr Leu Gln Ser Ile Thr Trp Gln Met Ile
            340                 345                 350

Glu Gln Ile Gln Phe Ile Lys Leu Phe Gly Met Ala Lys Ile Asp Asn
            355                 360                 365

Leu Leu Gln Glu Met Leu Leu Gly Gly Ser Pro Ser Asp Ala Pro His
            370                 375                 380

Ala His His Pro Leu His Pro His Leu Met Gln Glu His Met Gly Thr
385                 390                 395                 400

Asn Val Ile Val Ala Asn Thr Met Pro Thr His Leu Ser Asn Gly Gln
                405                 410                 415

Met Cys Glu Trp Pro Arg Pro Arg Gly Gln Ala Ala Thr Pro Glu Thr
            420                 425                 430

Pro Gln Pro Ser Pro Pro Gly Gly Ser Gly Ser Glu Pro Tyr Lys Leu
                435                 440                 445

Leu Pro Gly Ala Val Ala Thr Ile Val Lys Pro Leu Ser Ala Ile Pro
            450                 455                 460

Gln Pro Thr Ile Thr Lys Gln Glu Val Ile
465                 470

<210> SEQ ID NO 9
<211> LENGTH: 417
<212> TYPE: PRT
<213> ORGANISM: Homo sapiens

<400> SEQUENCE: 9

Met Arg Leu Ser Lys Thr Leu Val Asp Met Asp Met Ala Asp Tyr Ser
1               5                   10                  15

Ala Ala Leu Asp Pro Ala Tyr Thr Thr Leu Glu Phe Glu Asn Val Gln
                20                  25                  30

Val Leu Thr Met Gly Asn Asp Thr Ser Pro Ser Glu Gly Thr Asn Leu
            35                  40                  45

Asn Ala Pro Asn Ser Leu Gly Val Ser Ala Leu Cys Ala Ile Cys Gly
        50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
                85                  90                  95

Arg Phe Ser Arg Gln Cys Val Val Asp Lys Asp Lys Arg Asn Gln Cys
            100                 105                 110

```
Arg Tyr Cys Arg Leu Lys Lys Cys Phe Arg Ala Gly Met Lys Lys Glu
            115                 120                 125
Ala Val Gln Asn Glu Arg Asp Arg Ile Ser Thr Arg Arg Ser Ser Tyr
        130                 135                 140
Glu Asp Ser Ser Leu Pro Ser Ile Asn Ala Leu Leu Gln Ala Glu Val
145                 150                 155                 160
Leu Ser Arg Gln Ile Thr Ser Pro Val Ser Gly Ile Asn Gly Asp Ile
            165                 170                 175
Arg Ala Lys Lys Ile Ala Ser Ile Ala Asp Val Cys Glu Ser Met Lys
        180                 185                 190
Glu Gln Leu Leu Val Leu Val Glu Trp Ala Lys Tyr Ile Pro Ala Phe
            195                 200                 205
Cys Glu Leu Pro Leu Asp Asp Gln Val Ala Leu Leu Arg Ala His Ala
        210                 215                 220
Gly Glu His Leu Leu Leu Gly Ala Thr Lys Arg Ser Met Val Phe Lys
225                 230                 235                 240
Asp Val Leu Leu Leu Gly Asn Asp Tyr Ile Val Pro Arg His Cys Pro
            245                 250                 255
Glu Leu Ala Glu Met Ser Arg Val Ser Ile Arg Ile Leu Asp Glu Leu
        260                 265                 270
Val Leu Pro Phe Gln Glu Leu Gln Ile Asp Asp Asn Glu Tyr Ala Tyr
            275                 280                 285
Leu Lys Ala Ile Ile Phe Phe Asp Pro Asp Ala Lys Gly Leu Ser Asp
        290                 295                 300
Pro Gly Lys Ile Lys Arg Leu Arg Ser Gln Val Gln Val Ser Leu Glu
305                 310                 315                 320
Asp Tyr Ile Asn Asp Arg Gln Tyr Asp Ser Arg Gly Arg Phe Gly Glu
            325                 330                 335
Leu Leu Leu Leu Leu Pro Thr Leu Gln Ser Ile Thr Trp Gln Met Ile
        340                 345                 350
Glu Gln Ile Gln Phe Ile Lys Leu Phe Gly Met Ala Lys Ile Asp Asn
        355                 360                 365
Leu Leu Gln Glu Met Leu Leu Gly Gly Pro Cys Gln Ala Gln Glu Gly
        370                 375                 380
Arg Gly Trp Ser Gly Asp Ser Pro Gly Asp Arg Pro His Thr Val Ser
385                 390                 395                 400
Ser Pro Leu Ser Ser Leu Ala Ser Pro Leu Cys Arg Phe Gly Gln Val
            405                 410                 415
Ala

<210> SEQ ID NO 10
<211> LENGTH: 452
<212> TYPE: PRT
<213> ORGANISM: Homo sapiens

<400> SEQUENCE: 10

Met Val Ser Val Asn Ala Pro Leu Gly Ala Pro Val Glu Ser Ser Tyr
1               5                   10                  15
Asp Thr Ser Pro Ser Glu Gly Thr Asn Leu Asn Ala Pro Asn Ser Leu
            20                  25                  30
Gly Val Ser Ala Leu Cys Ala Ile Cys Gly Asp Arg Ala Thr Gly Lys
        35                  40                  45
His Tyr Gly Ala Ser Ser Cys Asp Gly Cys Lys Gly Phe Phe Arg Arg
    50                  55                  60
```

```
Ser Val Arg Lys Asn His Met Tyr Ser Cys Arg Phe Ser Arg Gln Cys
 65                  70                  75                  80

Val Val Asp Lys Asp Lys Arg Asn Gln Cys Arg Tyr Cys Arg Leu Lys
                 85                  90                  95

Lys Cys Phe Arg Ala Gly Met Lys Lys Glu Ala Val Gln Asn Glu Arg
            100                 105                 110

Asp Arg Ile Ser Thr Arg Arg Ser Ser Tyr Glu Asp Ser Ser Leu Pro
        115                 120                 125

Ser Ile Asn Ala Leu Leu Gln Ala Glu Val Leu Ser Arg Gln Ile Thr
    130                 135                 140

Ser Pro Val Ser Gly Ile Asn Gly Asp Ile Arg Ala Lys Lys Ile Ala
145                 150                 155                 160

Ser Ile Ala Asp Val Cys Glu Ser Met Lys Glu Gln Leu Leu Val Leu
                165                 170                 175

Val Glu Trp Ala Lys Tyr Ile Pro Ala Phe Cys Glu Leu Pro Leu Asp
            180                 185                 190

Asp Gln Val Ala Leu Leu Arg Ala His Ala Gly Glu His Leu Leu Leu
        195                 200                 205

Gly Ala Thr Lys Arg Ser Met Val Phe Lys Asp Val Leu Leu Leu Gly
    210                 215                 220

Asn Asp Tyr Ile Val Pro Arg His Cys Pro Glu Leu Ala Glu Met Ser
225                 230                 235                 240

Arg Val Ser Ile Arg Ile Leu Asp Glu Leu Val Leu Pro Phe Gln Glu
                245                 250                 255

Leu Gln Ile Asp Asp Asn Glu Tyr Ala Tyr Leu Lys Ala Ile Ile Phe
            260                 265                 270

Phe Asp Pro Asp Ala Lys Gly Leu Ser Asp Pro Gly Lys Ile Lys Arg
        275                 280                 285

Leu Arg Ser Gln Val Gln Val Ser Leu Glu Asp Tyr Ile Asn Asp Arg
    290                 295                 300

Gln Tyr Asp Ser Arg Gly Arg Phe Gly Glu Leu Leu Leu Leu Leu Pro
305                 310                 315                 320

Thr Leu Gln Ser Ile Thr Trp Gln Met Ile Glu Gln Ile Gln Phe Ile
                325                 330                 335

Lys Leu Phe Gly Met Ala Lys Ile Asp Asn Leu Leu Gln Glu Met Leu
            340                 345                 350

Leu Gly Gly Ser Pro Ser Asp Ala Pro His Ala His Pro Leu His
        355                 360                 365

Pro His Leu Met Gln Glu His Met Gly Thr Asn Val Ile Val Ala Asn
    370                 375                 380

Thr Met Pro Thr His Leu Ser Asn Gly Gln Met Cys Glu Trp Pro Arg
385                 390                 395                 400

Pro Arg Gly Gln Ala Ala Thr Pro Glu Thr Pro Gln Pro Ser Pro Pro
                405                 410                 415

Gly Gly Ser Gly Ser Glu Pro Tyr Lys Leu Leu Pro Gly Ala Val Ala
            420                 425                 430

Thr Ile Val Lys Pro Leu Ser Ala Ile Pro Gln Pro Thr Ile Thr Lys
        435                 440                 445

Gln Glu Val Ile
450

<210> SEQ ID NO 11
<211> LENGTH: 442
```

<212> TYPE: PRT
<213> ORGANISM: Homo sapiens

<400> SEQUENCE: 11

Met Val Ser Val Asn Ala Pro Leu Gly Ala Pro Val Glu Ser Ser Tyr
1               5                   10                  15

Asp Thr Ser Pro Ser Glu Gly Thr Asn Leu Asn Ala Pro Asn Ser Leu
            20                  25                  30

Gly Val Ser Ala Leu Cys Ala Ile Cys Gly Asp Arg Ala Thr Gly Lys
        35                  40                  45

His Tyr Gly Ala Ser Ser Cys Asp Gly Cys Lys Gly Phe Phe Arg Arg
    50                  55                  60

Ser Val Arg Lys Asn His Met Tyr Ser Cys Arg Phe Ser Arg Gln Cys
65                  70                  75                  80

Val Val Asp Lys Asp Lys Arg Asn Gln Cys Arg Tyr Cys Arg Leu Lys
                85                  90                  95

Lys Cys Phe Arg Ala Gly Met Lys Lys Glu Ala Val Gln Asn Glu Arg
            100                 105                 110

Asp Arg Ile Ser Thr Arg Arg Ser Ser Tyr Glu Asp Ser Ser Leu Pro
        115                 120                 125

Ser Ile Asn Ala Leu Leu Gln Ala Glu Val Leu Ser Arg Gln Ile Thr
130                 135                 140

Ser Pro Val Ser Gly Ile Asn Gly Asp Ile Arg Ala Lys Lys Ile Ala
145                 150                 155                 160

Ser Ile Ala Asp Val Cys Glu Ser Met Lys Glu Gln Leu Leu Val Leu
                165                 170                 175

Val Glu Trp Ala Lys Tyr Ile Pro Ala Phe Cys Glu Leu Pro Leu Asp
            180                 185                 190

Asp Gln Val Ala Leu Leu Arg Ala His Ala Gly Glu His Leu Leu Leu
        195                 200                 205

Gly Ala Thr Lys Arg Ser Met Val Phe Lys Asp Val Leu Leu Leu Gly
    210                 215                 220

Asn Asp Tyr Ile Val Pro Arg His Cys Pro Glu Leu Ala Glu Met Ser
225                 230                 235                 240

Arg Val Ser Ile Arg Ile Leu Asp Glu Leu Val Leu Pro Phe Gln Glu
                245                 250                 255

Leu Gln Ile Asp Asp Asn Glu Tyr Ala Tyr Leu Lys Ala Ile Ile Phe
            260                 265                 270

Phe Asp Pro Asp Ala Lys Gly Leu Ser Asp Pro Gly Lys Ile Lys Arg
        275                 280                 285

Leu Arg Ser Gln Val Gln Val Ser Leu Glu Asp Tyr Ile Asn Asp Arg
290                 295                 300

Gln Tyr Asp Ser Arg Gly Arg Phe Gly Glu Leu Leu Leu Leu Leu Pro
305                 310                 315                 320

Thr Leu Gln Ser Ile Thr Trp Gln Met Ile Glu Gln Ile Gln Phe Ile
                325                 330                 335

Lys Leu Phe Gly Met Ala Lys Ile Asp Asn Leu Leu Gln Glu Met Leu
            340                 345                 350

Leu Gly Gly Ser Pro Ser Asp Ala Pro His Ala His His Pro Leu His
        355                 360                 365

Pro His Leu Met Gln Glu His Met Gly Thr Asn Val Ile Val Ala Asn
    370                 375                 380

Thr Met Pro Thr His Leu Ser Asn Gly Gln Met Ser Thr Pro Glu Thr
385                 390                 395                 400

```
Pro Gln Pro Ser Pro Gly Ser Gly Ser Glu Pro Tyr Lys Leu
            405             410             415

Leu Pro Gly Ala Val Ala Thr Ile Val Lys Pro Leu Ser Ala Ile Pro
            420             425             430

Gln Pro Thr Ile Thr Lys Gln Glu Val Ile
            435             440
```

<210> SEQ ID NO 12
<211> LENGTH: 395
<212> TYPE: PRT
<213> ORGANISM: Homo sapiens

<400> SEQUENCE: 12

```
Met Val Ser Val Asn Ala Pro Leu Gly Ala Val Glu Ser Ser Tyr
1               5                   10                  15

Asp Thr Ser Pro Ser Glu Gly Thr Asn Leu Asn Ala Pro Asn Ser Leu
            20                  25                  30

Gly Val Ser Ala Leu Cys Ala Ile Cys Gly Asp Arg Ala Thr Gly Lys
        35                  40                  45

His Tyr Gly Ala Ser Ser Cys Asp Gly Cys Lys Gly Phe Phe Arg Arg
    50                  55                  60

Ser Val Arg Lys Asn His Met Tyr Ser Cys Arg Phe Ser Arg Gln Cys
65                  70                  75                  80

Val Val Asp Lys Asp Lys Arg Asn Gln Cys Arg Tyr Cys Arg Leu Lys
                85                  90                  95

Lys Cys Phe Arg Ala Gly Met Lys Lys Glu Ala Val Gln Asn Glu Arg
            100                 105                 110

Asp Arg Ile Ser Thr Arg Arg Ser Ser Tyr Glu Asp Ser Ser Leu Pro
        115                 120                 125

Ser Ile Asn Ala Leu Leu Gln Ala Glu Val Leu Ser Arg Gln Ile Thr
130                 135                 140

Ser Pro Val Ser Gly Ile Asn Gly Asp Ile Arg Ala Lys Lys Ile Ala
145                 150                 155                 160

Ser Ile Ala Asp Val Cys Glu Ser Met Lys Glu Gln Leu Leu Val Leu
                165                 170                 175

Val Glu Trp Ala Lys Tyr Ile Pro Ala Phe Cys Glu Leu Pro Leu Asp
            180                 185                 190

Asp Gln Val Ala Leu Leu Arg Ala His Ala Gly Glu His Leu Leu Leu
        195                 200                 205

Gly Ala Thr Lys Arg Ser Met Val Phe Lys Asp Val Leu Leu Leu Gly
    210                 215                 220

Asn Asp Tyr Ile Val Pro Arg His Cys Pro Glu Leu Ala Glu Met Ser
225                 230                 235                 240

Arg Val Ser Ile Arg Ile Leu Asp Glu Leu Val Leu Pro Phe Gln Glu
                245                 250                 255

Leu Gln Ile Asp Asp Asn Glu Tyr Ala Tyr Leu Lys Ala Ile Ile Phe
            260                 265                 270

Phe Asp Pro Asp Ala Lys Gly Leu Ser Asp Pro Gly Lys Ile Lys Arg
        275                 280                 285

Leu Arg Ser Gln Val Gln Val Ser Leu Glu Asp Tyr Ile Asn Asp Arg
    290                 295                 300

Gln Tyr Asp Ser Arg Gly Arg Phe Gly Glu Leu Leu Leu Leu Leu Pro
305                 310                 315                 320

Thr Leu Gln Ser Ile Thr Trp Gln Met Ile Glu Gln Ile Gln Phe Ile
```

```
                    325                 330                 335
Lys Leu Phe Gly Met Ala Lys Ile Asp Asn Leu Leu Gln Glu Met Leu
                340                 345                 350

Leu Gly Gly Pro Cys Gln Ala Gln Glu Gly Arg Gly Trp Ser Gly Asp
            355                 360                 365

Ser Pro Gly Asp Arg Pro His Thr Val Ser Ser Pro Leu Ser Ser Leu
    370                 375                 380

Ala Ser Pro Leu Cys Arg Phe Gly Gln Val Ala
385                 390                 395

<210> SEQ ID NO 13
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 13
atggacatgg ctgactacag tgct                                        24

<210> SEQ ID NO 14
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 14
acagcttgag gctccgtagt gttt                                        24

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
tctagagggc ctggagttca                                             20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
tcactgtctg gcctgttgag                                             20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
ttcaatgtcc ctgccatgta                                             20

<210> SEQ ID NO 18
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 18
catctccaga gtccagcaca                                                  20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
ttgctgacag gatgcagaag                                                  20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
cagtgaggcc aggatagagc                                                  20

<210> SEQ ID NO 21
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 21
gcccagcata cgaagaaaac a                                                21

<210> SEQ ID NO 22
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 22
tctctttgtc tggaagcatt cct                                              23

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
tctgcacact cccagacaag                                                  20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
agtcacccat caccgtcttc                                                  20
```

```
<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ggcaaggatt tgatggagaa                                                20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
cccagttctc tggacaaagg                                                20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
acatggaaca agcctccaag                                                20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
tggccaccac agctatatca                                                20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
tgaaccgctt ctgggattac                                                20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
tgtgtgactt gggagctctg                                                20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 31
ggaggatctg agggaagacc                                               20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
ggcagcagat cctttcagag                                               20

<210> SEQ ID NO 33
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 33
tttggtggca cacagcttg                                                19

<210> SEQ ID NO 34
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 34
atggaataca cctgcgtaac gg                                            22

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
gaaggcctaa gcacaacagc                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
aagcacttga ccctggtacg                                               20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
gccaagaagt cggtggataa                                               20

<210> SEQ ID NO 38
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
aacaccttct gctgcgtctc                                                  20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
gctcagatct ttgcgaattc                                                  20

<210> SEQ ID NO 40
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 40
cgcttcgatt tctgtctcc                                                   19

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
tggtcctcaa ggtttccaag                                                  20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
ttaccagctt ccccatcatc                                                  20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
tgcagaaaat ggttgctttg                                                  20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
```
gctttcctga ttgccgtaag                                           20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
atggagatca cagcccagtc                                           20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
cgatctcctc ctgcagtttc                                           20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
tgagaatggt gaatgccagt                                           20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
gagtcatctc cgccttcatc                                           20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
taacccagga ggaagcacac                                           20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
cttcattgca ctccctctcc                                           20

<210> SEQ ID NO 51
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 51
ccatccgtca ttctctctcc                                               20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
tcgaacatgt tgccagagtc                                               20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
gacgtctcca ggtctcaacc                                               20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
cacccgtgtt agtgaacgtg                                               20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
ctcaccctca gctggatagg                                               20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
ccctttggag tagctgcttg                                               20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
aatgcaatcc gttttggaag                                               20
```

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
gccagagatt tgaggtctgc                                           20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
catcgtggac aacatgaagg                                           20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
cagggtctgt aggcaggttc                                           20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
ttgaagggtc tggaagagga                                           20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
tcatcgaaca agcagagcag                                           20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
gcatctgacc cgagtctctc                                           20

<210> SEQ ID NO 64
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 64
gaatggcctg agcttttcag                                               20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
aatggagatg gcaaagagga                                               20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
gagagccgaa cagttggaag                                               20

<210> SEQ ID NO 67
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 67
ggactctcca cctgcaagac                                               20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
gactggcgag ccttagtttg                                               20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
ggttccctgg cataatctga                                               20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
atggctgaac agggaaacac                                               20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
tggacgttgg aggaaagaag                                                    20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
tcccagggca caataaagtc                                                    20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
tgtgcaactt tgtggagagg                                                    20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
aattgcaacc caggtggtag                                                    20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
tcgtactgga aggctcttgg                                                    20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
gtaggagtac gggctgagca                                                    20

<210> SEQ ID NO 77
<211> LENGTH: 37
<212> TYPE: DNA
<213> ORGANISM: Artificial sequence
<220> FEATURE:
<223> OTHER INFORMATION: Synthetic oligonucleotide

```
<400> SEQUENCE: 77
ggtttttgag ggtgagggtg agggtgaggg tgagggt                                    37

<210> SEQ ID NO 78
<211> LENGTH: 39
<212> TYPE: DNA
<213> ORGANISM: Artificial sequence
<220> FEATURE:
<223> OTHER INFORMATION: Synthetic oligonucleotide

<400> SEQUENCE: 78
tcccgactat ccctatccct atccctatcc ctatcccta                                  39

<210> SEQ ID NO 79
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 79
cagcaagtgg gaaggtgtaa tcc                                                   23

<210> SEQ ID NO 80
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 80
cccattctat catcaacggg tacaa                                                 25
```

METHODS FOR THE TREATMENT AND PREVENTION OF LIVER DISEASE

CROSS-REFERENCE TO RELATED APPLICATIONS

This application claims priority to U.S. Application Ser. No. 61/763,744 filed Feb. 12, 2013, the contents of which are incorporated by reference in its entirety.

GRANT INFORMATION

This invention was made with government support under DK048794 awarded by the National Institutes of Health. The government has certain rights in the invention.

SEQUENCE LISTING

The specification further incorporates by reference the Sequence Listing submitted herewith via EFS on May 19, 2014. Pursuant to 37 C.F.R. § 1.52(e)(5), the Sequence Listing text file, identified as 0723960546Seqlist.txt, is 65,477 bytes and was created on May 16, 2014. The Sequence Listing, electronically filed herewith, does not extend beyond the scope of the specification and thus does not contain new matter.

BACKGROUND

Cirrhosis of the liver, a disease that is difficult to manage, is responsible for 1.2% of all U.S. deaths (1). Cirrhosis is most commonly caused by alcoholism, hepatitis B and hepatitis C, and fatty liver disease, but has many other possible causes such as non-alcoholic steatohepatitis, primary biliary cirrhosis, primary sclerosing cholangitis, autoimmune hepatitis, hereditary hemochromatosis, Wilson's disease, or alpha 1-antitrypsin deficiency.

Late stages of cirrhosis are characterized by portal hypertension and hepatic encephalopathy, terminal extrahepatic processes that result from fibrosis and vascular remodeling of the cirrhotic liver (2,3). These pathologies are superimposed on liver failure, which results from the inability of hepatocytes to adequately synthesize coagulation factors, conjugate and secrete bilirubin, and regulate metabolism (4-7). Generally, liver damage from cirrhosis cannot be reversed. Therefore, aggressive management can extend life, but the only definitive therapy for end-stage cirrhosis is orthotopic liver transplantation (8).

The cause of organ failure in cirrhosis is poorly understood, but impaired hepatocytes have both intrinsic damage and reside in an abnormal microenvironment (2-8). Studies have shown that somatic cells can be reprogrammed into pluripotent stem cells and fibroblasts or hepatocytes can be reprogrammed into other mature cell lineages following forced expression of selected transcription factors (9,10), although these methods have not been proven in vivo for the treatment of cirrhosis. Accordingly, there is a need for new methods to treat and/or manage cirrhosis and chronic liver disease.

SUMMARY

The presently disclosed invention is directed to the discovery that hepatocyte nuclear factor 4 alpha (HNF4α; also known as NR2A1), a transcription factor, reverses hepatocyte dysfunction in an animal model of cirrhosis, resulting in improvement in hepatic function, treatment of cirrhosis, and prolonged survival.

Accordingly, in one aspect, the present invention provides a method of treating or reducing or preventing hepatic failure or cirrhosis in a subject, e.g., a human subject, comprising administering a therapeutically effective amount of a pharmaceutical composition comprising an HNF4α agonist to the subject. In one embodiment, the agonist is a small molecule. In another embodiment, the agonist is an HNF4α nucleic acid molecule. For example, the HNF4α nucleic acid molecule can be a therapeutic vector comprising a nucleic acid molecule encoding HNF4α. In one embodiment, a hepatocyte from the subject can be transduced with the therapeutic vector in vitro and reintroduced into the subject, or transduced in vivo. In another embodiment, the agonist is an HNF4α protein or functional fragment thereof or a peptidomimetic thereof.

In another embodiment, the present invention provides a method of treating or preventing hepatic failure or cirrhosis in a subject comprising administering a therapeutically effective amount of a pharmaceutical composition comprising an agonist to a hepatic network factor regulated by HNF4α, such as, for example, HNF1α, FOXA2, or CEBPα, alone or in combination with an HNF4α agonist.

In some embodiments, the agonist is administered alone or in combination with one or more other agent or procedure used for the treatment or prevention of hepatic failure or cirrhosis or symptoms thereof, e.g., interferon therapy, diuretic drugs, transjugular intrahepatic portosystemic shunt (TIPS), paracentesis, antibiotics, drugs for the prevention of variceal bleeding, lactulose, changes to diet, and/or abstinence from alcohol. In one embodiment, the HNF4α agonist is administered in a subject as a bridge to liver transplantation.

BRIEF DESCRIPTION OF THE FIGURES

FIGS. 1A-E. Characterization of the hepatocyte transcription factor network in decompensated cirrhosis. (A) Expression changes in the hepatocyte transcription factor network in decompensated cirrhosis (microarray data). (B) Immunohistochemistry; magnification, ×100 and (cytospins) ×200 (C) qPCR and (D) western blot for HNF4α expression in liver tissue and isolated hepatocytes from compensated and decompensated cirrhotic livers. Normal age-matched livers or hepatocytes were used as controls. β-actin was used as the PCR control. (E) Expression of liver-specific genes and genes affected downstream of HNF4α.

FIGS. 2A-B. Effect of HNF4α re-expression in isolated hepatocytes from decompensated cirrhotic livers. (A) qRT-PCR analysis of hepatocyte transcription factor network and hepatocyte-specific genes. (B) Albumin synthesis and cytochrome P450 (CYP3A4) activity. Studies were carried out on culture day 2 and compare hepatocytes from normal liver and decompensated cirrhotic livers, the latter also treated with AAV-HNF4α-GFP or AAV-GFP.

FIGS. 7A1-7A9 and 7B1-7B2. (A) Exemplary human HNF4α nucleic acid sequences, as set forth in SEQ ID NOs:1-6, include HNF4α transcript variants 1-6, respectively, set forth as Genbank accession numbers GI:385298690, GI:385298689, GI:385298691, GI:385298688, GI:385298686, and GI:385298687, respectively. (B) Exemplary human HNF4α amino acid sequences, as set forth in SEQ ID NOs:7-12, include HNF4α transcript variants a-f, respectively, set forth as Genbank accession numbers GI:31077207, GI:31077205, GI:31077209, GI:71725339, GI:71725341, and GI:71725336, respectively.

DETAILED DESCRIPTION

Figure 1:
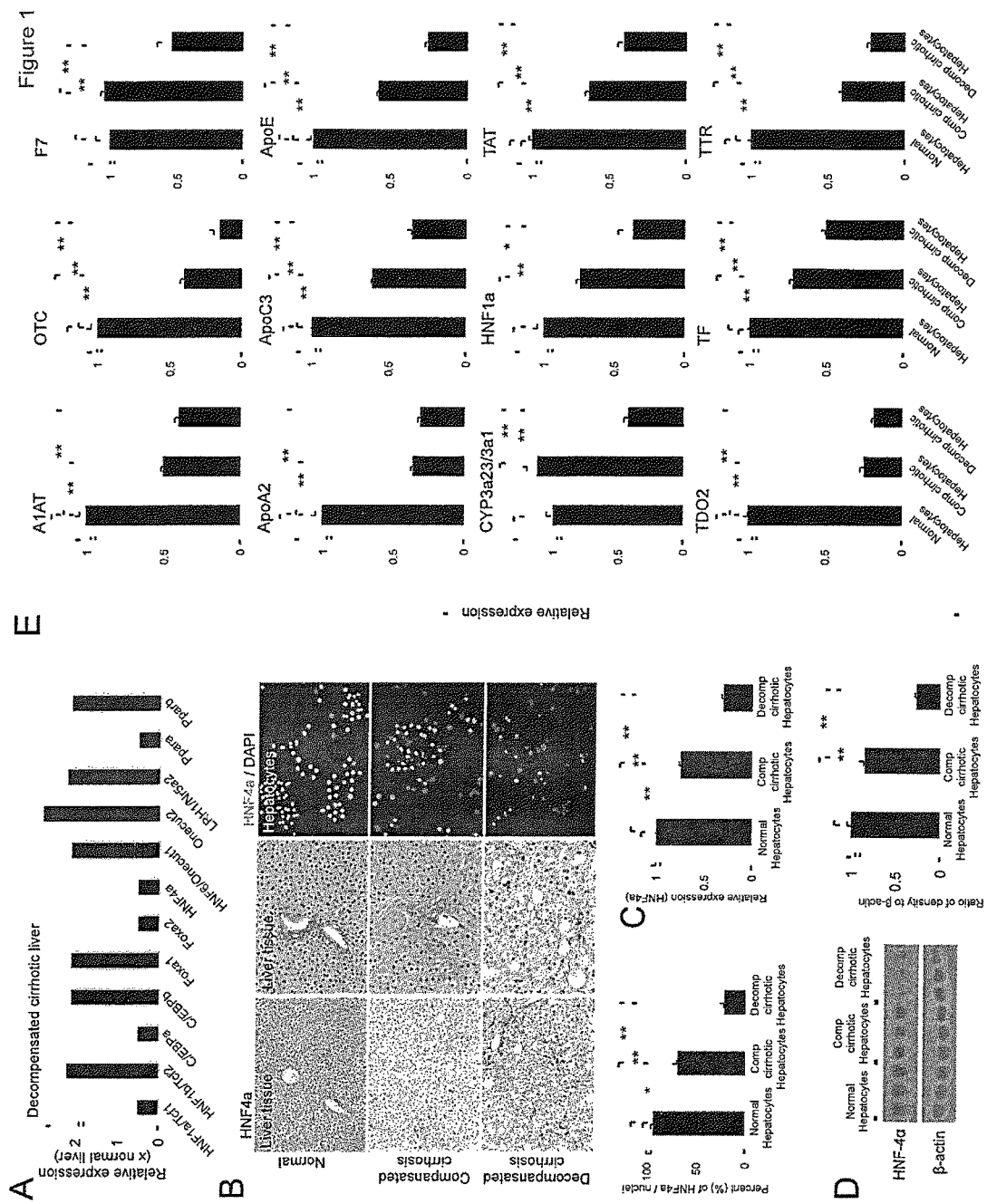

The present disclosure describes the discovery that the forced expression of hepatocyte nuclear factor 4 alpha (HNF4α; also known as NR2A1), a transcription factor, reverses hepatocyte dysfunction in cirrhosis in vivo. In particular, the present inventors have found that transduction of hepatocytes in cirrhotic animals with irreversible decompensated function produced a profound and immediate improvement in hepatic function and prolonged survival.

Furthermore, the present inventors confirm the role of HNF4α as an important regulator of the hepatocyte transcription factor network and a master gene for liver function that is down-regulated in advanced cirrhosis. Down-regulation of HNF4α has a profound effect on the end-stage cirrhotic hepatocyte in vitro, as replenishment of this single factor revitalizes hepatocyte function.

As described herein, using an animal model of cirrhosis and progressive liver failure (11), the inventors have shown that end-stage cirrhotic hepatocytes, previously considered to be senescent and irreversibly dysfunctional, can quickly revert to normal function following transduction with the transcription factor HNF4α, even though surrounded by an abnormal extracellular matrix. HNF4α reexpression immediately corrected the phenotype of cultured cirrhotic hepatocytes and reversed terminal end-stage cirrhosis and liver failure in vivo in this animal model. Normalization of function took place in two weeks while portal hypertension, evidenced by the presence of ascites, regressed when histological reversal of cirrhosis was more complete. It was found that HNF4α acted by phenotypically correcting diseased hepatoctyes, not by stimulating their replacement.

Accordingly, the invention provides methods for treating liver failure and cirrhosis (and/or improving liver function in a subject having a cirrhotic liver), comprising administering a therapeutically effective amount of an HNF4α agonist, e.g., a HNF4α nucleic acid, protein or functional fragment thereof, peptidomimetic, small molecule, or other drug candidate, to a subject, e.g., a mammal. In one embodiment, the HNF4α agonist is a therapeutic vector comprising a nucleic acid molecule encoding HNF4α protein or a functional fragment thereof. In another embodiment, the HNF4α agonist is a small molecule agonist.

In another embodiment, the present invention provides a method of treating or preventing hepatic failure or cirrhosis in a subject comprising administering a therapeutically effective amount of a pharmaceutical composition comprising an agonist to a hepatic network factor regulated by HNF4α, such as, for example, HNF1α, FOXA2, or CEBPα (Locker J., Transcriptional Control of Hepatocyte Differentiation. In: Monda S P, editor, Molecular Pathology of Liver Disease. London, Academic Press; 2001; Kyrmizi, et al. 2006, Genes Dev. 20(16):2293-305; Odom et al. 2006 Mol. Sys. Biol. 2:2006), alone or in combination with an HNF4α agonist.

An "individual" or "subject" herein is a vertebrate, such as a human. Mammals include, but are not limited to, humans, primates, farm animals, sport animals, rodents and pets.

An "effective amount" of a substance as that term is used herein is that amount sufficient to effect beneficial or desired results, including clinical results, and, as such, an "effective amount" depends upon the context in which it is being applied. In the context of administering a composition that improves liver function, improves liver histology (e.g., fibrosis), or treats liver failure or cirrhosis, an effective amount of an HNF4α agonist is an amount sufficient to achieve such a modulation as compared to the liver function, histology, or level of cirrhosis when there is no an HNF4α agonist administered. An effective amount can be administered in one or more administrations.

As used herein, and as well-understood in the art, "treatment" is an approach for obtaining beneficial or desired results, including clinical results. For purposes of this subject matter, beneficial or desired clinical results include, but are not limited to, alleviation or amelioration of one or more symptoms, diminishment of extent of disease, stabilized (i.e., not worsening) state of disease, prevention of disease, delay or slowing of disease progression, and/or amelioration or palliation of the disease state. "Treatment" can also mean prolonging survival as compared to expected survival if not receiving treatment.

Agonists

The term "HNF4α therapeutic" refers to various forms of HNF4α nucleic acids, polypeptides, peptidomimetics, or small molecules, which can increase expression of liver-specific genes, increase CYP activity, increase liver function, improves liver histology (e.g., fibrosis), treat or prevent cirrhosis, or prolong survival in a subject suffering from liver failure. An HNF4α therapeutic that mimics, potentiates, or increases the activity of a wild-type HNF4α polypeptide is a "HNF4α agonist." An HNF4α therapeutic includes a gene therapy vector comprising an HNF4α nucleic acid sequence.

The term "agonist," as used herein, is meant to refer to an agent that mimics or upregulates (e.g., increases, potentiates or supplements) HNF4α expression or bioactivity, or expression or bioactivity of a hepatic network factor regulated by HNF4α, such as, for example, HNF1α, FOXA2, or CEBPα.

An HNF4α agonist can be a small molecule, a wild-type HNF4α nucleic acid, protein, derivative, or functional fragment thereof having at least one bioactivity of the wild-type HNF4α and the ability to increase expression of liver-specific genes, increase CYP activity, increase liver function, improve liver histology (e.g., fibrosis), treat or prevent cirrhosis, or prolong survival in a subject suffering from liver failure. In one embodiment, an HNF4α agonist is an agent that upregulates expression (which includes forced reexpression) of an HNF4α gene. An agonist can also be a compound which increases the interaction of a HNF4α polypeptide with another molecule. Accordingly, a HNF4α agonist includes a nucleic acid (e.g., using adenoviral expression), micro RNA, e.g., miR-122, which has been shown to be regulated by HNF4α, (Li, et al, 2011 *J. Hepatol.* 55(3):602-11), a peptidomimetic, protein, or functional fragment thereof, peptide, or small molecule (or other drug candidate) that increases the expression or activity of HNF4α.

Accordingly, an agonist against a hepatic network factor regulated by HNF4α, such as, for example, HNF1α, FOXA2, or CEBPα includes a nucleic acid (e.g., using adenoviral expression), micro RNA, a peptidomimetic, protein, or functional fragment thereof, peptide, or small molecule (or other drug candidate) that increases the expression or activity of a hepatic network factor regulated by HNF4α.

Small Molecule Agonists

Small molecule agonists can be used in the methods of the invention to increase expression or activity of HNF4α or a hepatic network factor regulated by HNF4α, such as, for example, HNF1α, FOXA2, or CEBPα. In one embodiment, exemplary small molecules that can be used in the methods of the invention are described in Le Guével R et al. Bioorg. Med Chem., 2009 Oct. 1; 17(19):7021-30. The small molecules identified therein are synthetic compounds bearing a methoxy group branched on a nitronaphthofuran backbone. The nitro group and a complete naphthofuran backbone were required for full activity of the small molecules tested.

Furthermore, adding a hydroxy group at position 7 of the minimal backbone led to an active compound. These compounds were found to be highly toxic in a human HepG2C3A hepatoma cell assay, except when methylated on the furan ring. One such compound was able to modulate HNF4α-driven transcription in transfected HepG2C3A cell. Therefore, HNF4α activity can be modulated (e.g., increased) by small molecules.

In certain non-limiting embodiments, the small molecule comprises the structure of Formula I:

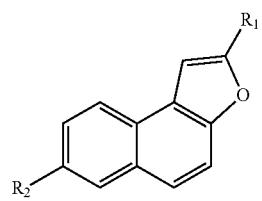

wherein $R_1$ is selected from the group consisting of $NO_2$, COOEt, COOH, $CONH_2$, and H; and wherein $R_2$ is selected from the group consisting of $OCH_3$, H, OH, $OCH_2COOEt$, $OCH_2COOH$, and OMe; wherein Me is methyl and Et is ethyl.

In certain non-limiting embodiments, the small molecule comprises the structure of Formula I wherein $R_1$ is $NO_2$ and $R_2$ is OH.

In certain non-limiting embodiments, the small molecule comprises the structure of Formula I wherein $R_1$ is $CONH_2$ and $R_2$ is H.

In certain non-limiting embodiments, the small molecule comprises the structure of Formula II:

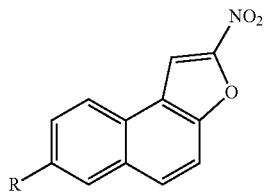

wherein R is selected from the group consisting of:

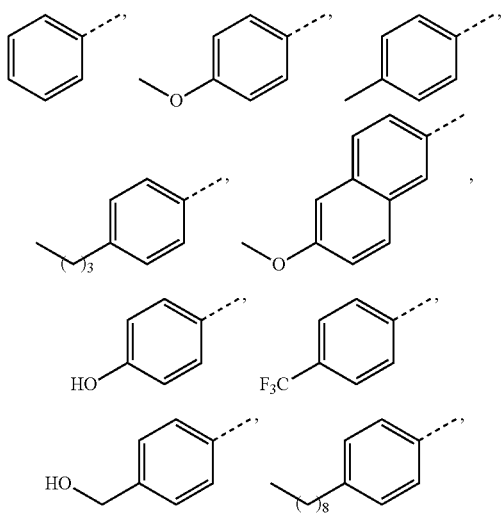

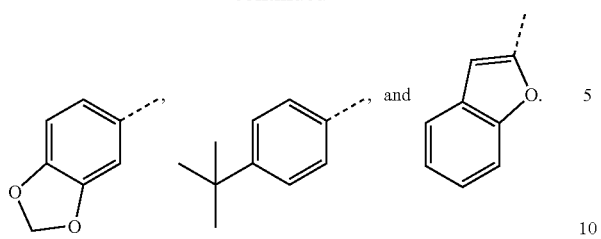

In certain non-limiting embodiments, the small molecule comprises the structure of Formula III:

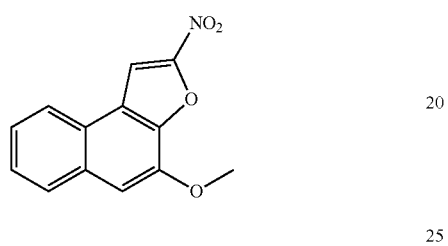

In certain non-limiting embodiments, the small molecule comprises the structure of Formula IV:

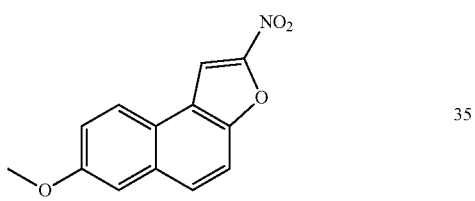

In certain non-limiting embodiments, the small molecule comprises the structure of Formula V:

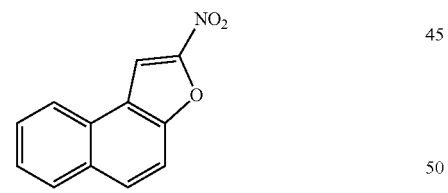

In certain non-limiting embodiments, the small molecule comprises the structure of Formula VI:

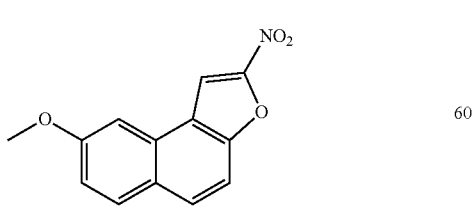

In certain non-limiting embodiments, the small molecule comprises the structure of Formula VII:

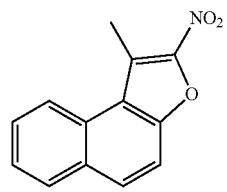 [SMILES: Cc1c([N+](=O)[O-])oc2ccc3ccccc3c12]

In certain non-limiting embodiments, the small molecule comprises the structure of Formula VIII:

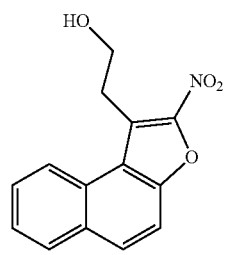 [SMILES: O=[N+]([O-])c1oc2ccc3ccccc3c2c1CCO]

In certain non-limiting embodiments, the small molecule comprises the structure of Formula IX:

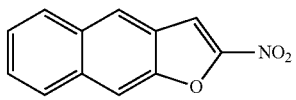 [SMILES: O=[N+]([O-])c1cc2cc3ccccc3cc2o1]

In certain non-limiting embodiments, the small molecule comprises the structure of Formula X:

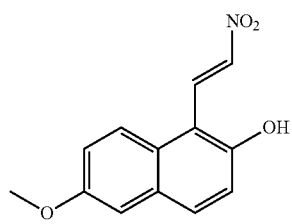 [SMILES: COc1ccc2c(/C=C/[N+](=O)[O-])c(O)ccc2c1]

In certain non-limiting embodiments, the small molecule comprises the structure of Formula XI:

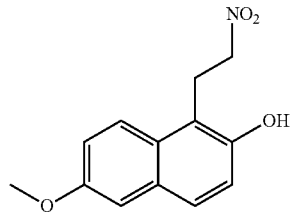 [SMILES: COc1ccc2c(CC[N+](=O)[O-])c(O)ccc2c1]

In certain non-limiting embodiments, the small molecule comprises the structure of Formula XII:

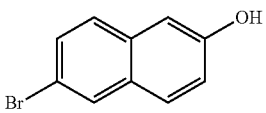

In certain non-limiting embodiments, the small molecule comprises the structure of Formula XIII:

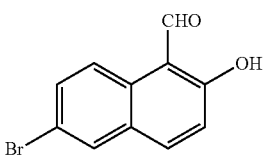

In certain non-limiting embodiments, the small molecule comprises the structure of Formula XIV:

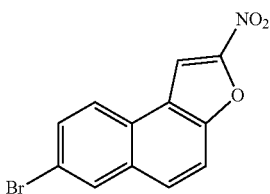 [SMILES: O=[N+]([O-])c1cc2c(ccc3cc(Br)ccc32)o1]

HNF4α Nucleic Acid Agonists

The term "HNF4α nucleic acid" or "HNF4α" refers to a nucleic acid encoding an HNF4α protein, such as, but not limited to, nucleic acids having SEQ ID NOs:1-6 (Genbank accession numbers GI:385298690, GI:385298689, GI:385298691, GI:385298688, GI:385298686, and GI:385298687, respectively; FIG. 7A), fragments thereof, complement thereof, and derivatives thereof.

The invention further provides for the use of variant HNF4α polynucleotides, and fragments thereof, that differ from the nucleotide sequence shown in SEQ ID NOs: 1-6 due to degeneracy of the genetic code and thus encode the same protein as that encoded by the nucleotide sequences shown in SEQ ID NOs: 1-6.

The invention also provides for the use of HNF4α nucleic acid molecules encoding the variant polypeptides described above. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed herein, the variants can contain nucleotide substitutions, deletions, inversions and insertions.

Typically, variants have a substantial identity with a nucleic acid molecules of SEQ ID NOS:1-6 and the complements thereof. Variation can occur in either or both the coding and non-coding regions. The variations can produce both conservative and non-conservative amino acid substitutions.

Orthologs, homologs, and allelic variants can be identified using methods well known in the art. These variants comprise a nucleotide sequence encoding a polypeptide that is typically at least about 60-65%, 65-70%, 70-75%, more typically at least about 80-85%, and most typically at least about 90-95% or more homologous to the nucleotide sequence shown in SEQ ID NOS:1-6 or a fragment of this sequence. Such nucleic acid molecules can readily be identified as being able to hybridize under stringent conditions, to the nucleotide sequence shown in SEQ ID NOS:1-6 or a fragment of the sequence.

In one embodiment, nucleic acids comprising sequences encoding HNF4α protein are administered to treat or prevent liver failure or cirrhosis, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below. For a review of gene therapy in the liver, see Domvri, et al., Current Gene Therapy 12(6): 463-483(21) (2012) and Atta, World J Gastroenterol. 2010 Aug. 28; 16(32): 4019-4030. For general reviews of the methods of gene therapy, see Kron and Kreppel, Curr Gene Ther 12(5):362-73 (2012); Yi et al. Curr Gene Ther 11(3): 218-28 (2011); Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an HNF4α polypeptide or functional fragment thereof, said nucleic acid sequences being part of expression vectors that express the HNF4α polypeptide or functional fragments thereof in a suitable host. In particular, such nucleic acid sequences have promoters operably linked to the HNF4α coding region, said promoter being inducible or constitutive, and, optionally, tissue-specific. Because of their universal activity, viral promoters were components of many first-generation vectors. However, many of the viral promoters, such as the cytomegalovirus (CMV) promoter, are attenuated or completely shut-off in organs such as the liver. In comparison to viral or housekeeping promoters, tissue- or liver-specific promoters direct higher levels of expression in vivo. (Atta, World J Gastroenterol. 2010 Aug. 28; 16(32): 4019-4030).

Delivery of nucleic acid into a subject or hepatocyte may be either direct, in which case the subject or hepatocyte is directly exposed to the nucleic acid or nucleic acid-carrying vectors, or indirect, in which case, hepatocytes are first transformed with the nucleic acids in vitro, then transplanted into the patient. These two approaches are known, respectively, as in vivo or ex vivo gene therapy.

The nucleic acid may be directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, *J Biol. Chem.* (1987); 262:4429-4432). The nucleic acid-ligand complexes can also be formed in which the ligand comprises a fusogenic viral peptide to disrupt endosomes, allowing the nucleic acid to avoid lysosomal degradation. In addition, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA (1989); 86:8932-8935; Zijlstra et al., Nature (1989); 342:435-438).

The liver is an attractive target for gene therapy because hepatocytes are readily accessible via the blood stream. The endothelium of hepatic sinusoids displays fenestrations that are 100 nm wide and that allow macromolecules such as viral particles to cross the endothelium and reach hepatocytes. Moreover, the hepatic blood flow represents one-fifth of the cardiac output. Thus, any particle injected into the blood circulation can quickly reach the liver. For this reason, the vascular route is commonly used. (Atta, World J Gastroenterol. 2010 Aug. 28; 16(32): 4019-4030).

A method for inravascular regional hydrodynamic delivery of vectors has been developed. The method entails the use of an occlusion balloon catheter into the inferior vena cava and retro dynamically injecting the plasmid in saline solution towards the liver and through the hepatic vein. This retrodynamic hepatic vein gene delivery method has been performed in pigs, and led to liver transgene expression. (Crespo A, Gene Ther. 2005; 12:927-935; Eastman S J, Hum Gene Ther. 2002; 13:2065-2077; Brunetti-Pierri N, Mol Ther. 2007; 15:732-740; Dariel A, J Pediatr Surg. 2009; 44:517-522).

Retrograde administration of adenoviruses into the common bile duct has been shown to induce efficient transgene expression in the liver without causing severe adverse effects, thus supporting the feasibility of adenovirus-mediated gene transfer into the liver in clinical settings by means of endoscopic retrograde cholangiography. (Kuriyama S, Int J Mol Med. 2005; 16:503-508; Kuriyama S, Oncol Rep. 2005; 13:825-830; Peeters M J, Hum Gene Ther. 1996; 7:1693-1699). Repeat administration of adenoviruses into the common bile duct is successful in re-expressing the transgene in the liver. (Tominaga K, Gut. 2004; 53:1167-1173; Tsujinoue H, Int J Oncol. 2001; 18:575-580).

Another method for delivery of gene products into liver cells is also described in U.S. Patent Application Publication No. 20100010068. This method involves limiting blood flow to the liver during infusion of the vector into the liver.

In a specific embodiment, a viral vector that contains nucleic acid encoding an HNF4α polypeptide or a functional fragment thereof may be used. For example, a retroviral vector can be used (see Miller et al., Meth. Enzymol. (1993); 217:581-599). These retroviral vectors contain the components necessary for the correct packaging of the viral genome and integration into the host cell DNA. More detail about retroviral vectors can be found in Boesen et al., Biotherapy (1994); 6:291-302. Other references illustrating the use of retroviral vectors in gene therapy are: Anson, Genet Vaccines Ther 13; 2(1):9 (2004); Clowes et al., *J. Clin. Invest.* (1994); 93:644-651; Kiem et al., Blood (1994); 83:1467-1473; Salmons and Gunzberg, Human Gene Therapy (1993); 4:129-141; and Grossman and Wilson, Curr. Opin. in Genetics and Devel. (1993); 3:110-114.

Adenoviruses are especially attractive vehicles for delivering genes. Adenoviruses naturally infect respiratory epithelia where they cause a mild disease. Other targets for adenovirus-based delivery systems include the liver. Adenoviruses have the advantage of being capable of infecting non-dividing cells. Kron and Kreppel, Curr Gene Ther 12(5):362-73 (2012) and Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In one embodiment, adenovirus vectors are used.

Adeno-associated virus (AAV) may also be used (Zhong et al. J Genet Syndr Gene Ther January 10; S1. pii:008; High, K A, Blood, 120(23):4482-7 (2012); Walsh et al., Proc. Soc. Exp. Biol. Med. 204:289-300 (1993); U.S. Pat. No. 5,436,146). In a preferred embodiment, AAV vectors are used. Vectors that can be used in gene therapy are discussed below in detail below.

Another approach to gene therapy involves transferring a gene to a hepatocyte in tissue culture by such methods as electroporation, lipofection, calcium phosphate mediated transfection, or viral infection. Usually, the method of transfer includes the transfer of a selectable marker to the hepatocytes. The cells are then placed under selection to isolate those hepatocytes that have taken up and are expressing the transferred gene. Those hepatocytes are then delivered to a patient.

In one embodiment, a genetic construct expressing HNF4α can be introduced into the subject's hepatocytes which can then be propagated ex vivo in, for example, a tolerized non-human animal with a chimeric liver as described in, for example, U.S. Pat. No. 6,525,242. Alternatively, the hepatocytes may be used to colonize the liver of a tolerized animal prior to or contemporaneous with the introduction of the desired transgene via a gene therapy vector. The cells can then be harvested from the chimeric animal and reintroduced into the subject. Hepatocytes used for colonization may be enriched for cells containing the desired construct, for example, by selection by culture conditions, antibody/FACS methods, etc. which eliminate cells lacking the construct.

The nucleic acid can be introduced into a hepatocyte prior to administration in viva of the resulting recombinant hepatocyte. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92 m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant hepatocytes can be delivered to a patient by various methods known in the art. The amount of cells envisioned for use depends on the desired effect, patient state, etc., and can be determined by one skilled in the art.

Recombinant cells can also be used in gene therapy, where nucleic acid sequences encoding an HNF4α protein or functional fragment thereof, are introduced into the cells such that they are expressible by the cells or their progeny, and the recombinant cells are then administered in viva for therapeutic effect. For example, stem or progenitor cells can be used. Any stem and/or progenitor cells which can be isolated and maintained in vitro can potentially be used (see e.g. PCT Publication WO 94/08598; Porada and Porada, J. Genet Syndr Gene Ther., May 25; S1. p 11:011 (2012); Stemple and Anderson, Cell 71:973-985 (1992); Rheinwald, Meth. Cell Bio. 21A:229 (1980); and Pittelkow and Scott, Mayo Clinic Proc. 61:771 (1986)).

HNF4α Polypeptide Agonists

The terms "HNF4α polypeptide," "HNF4α protein' and "HNF4α" are intended to encompass polypeptides comprising the amino acid sequence of SEQ ID NOs:7-12 (Genbank accession numbers GI:31077207, GI:31077205, GI:31077209, GI:71725339, GI:71725341, and GI:71725336, respectively; FIG. 7B), fragments thereof (e.g., functional fragments thereof), and variants thereof, and include agonist polypeptides.

In one embodiment, the present invention provides for the use of an isolated or purified HNF4α polypeptide and variants and fragments thereof. The invention also encompasses the use of sequence variants. Variants include a substantially homologous protein encoded by the same genetic locus in an organism, i.e., an allelic variant. Variants also encompass proteins derived from other genetic loci in an organism, but having substantial homology to the HNF4α protein of SEQ ID NOs: 7-12. Variants also include proteins substantially homologous to the HNF4α protein but derived from another organism, i.e., an ortholog. Variants also include proteins that are substantially homologous to the HNF4α protein that are produced by chemical synthesis. Variants also include proteins that are substantially homologous to the HNF4α protein that are produced by recombinant methods.

As used herein, two polypeptides (or regions thereof) are substantially homologous when the amino acid sequences are at least about 60-65%, 65-70%, 70-75%, typically at least about 80-85%, and most typically at least about 90-95%, or 95-99% or more homologous. A substantially homologous amino acid sequence, according to the present invention, will be encoded by a nucleic acid sequence hybridizing to the nucleic acid sequence, or portion thereof, of the sequence shown in SEQ ID NOS:-7-12 under stringent conditions.

The HNF4α proteins used in the methods of the invention also include HNF4α polypeptides having additions, deletions or substitutions of amino acid residues (variants) which do not substantially alter the biological activity of the protein. Those individual sites or regions of HNF4α which may be altered without affecting biological activity may be determined by examination of the structure of the HNF4α binding domains, for example. Alternatively, one may empirically determine those regions which would tolerate amino acid substitutions by alanine scanning mutagenesis (Cunningham et al. Science 244, 1081-1085 (1989)). In this method, selected amino acid residues are individually substituted with a neutral amino acid (e.g., alanine) in order to determine the effects on biological activity.

It is generally recognized that conservative amino acid changes are least likely to perturb the structure and/or function of a polypeptide. Accordingly, the invention encompasses one or more conservative amino acid changes within a HNF4α protein. Conservative amino acid changes generally involve substitution of one amino acid with another that is similar in structure and/or function (e.g., amino acids with side chains similar in size, charge and shape). Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residue within a HNF4α protein can be replaced with other amino acid residues from the same side chain family and the altered protein can be tested for retained function using the functional assays described herein. Modifications can be introduced into an antibody of this disclosure by standard techniques known in the art, such as site-directed mutagenesis and PCR-mediated mutagenesis. If such substitutions result in a retention in biological activity, then more substantial changes may be introduced and/or other additions/deletions may be made and the resulting products screened. In one embodiment, deletions or additions can be from 5-10 residues, alternatively from 2-5 amino acid residues, or from 1-2 residues.

Vectors

The terms "vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include plasmids, phages, viruses, etc.; they are discussed in greater detail below. A "therapeutic vector" as used herein refers to a vector which is acceptable for administration to an animal, and particularly to a human.

Vectors typically comprise the DNA of a transmissible agent, into which foreign DNA is inserted. A common way to insert one segment of DNA into another segment of DNA involves the use of enzymes called restriction enzymes that cleave DNA at specific sites (specific groups of nucleotides) called restriction sites. Generally, foreign DNA is inserted at one or more restriction sites of the vector DNA, and then is carried by the vector into a host cell along with the transmissible vector DNA. A segment or sequence of DNA having inserted or added DNA, such as an expression vector, can also be called a "DNA construct." A common type of vector is a "plasmid", which generally is a self-contained molecule of double-stranded DNA, usually of bacterial origin, that can readily accept additional (foreign) DNA and which can readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. Promoter DNA is a DNA sequence which initiates, regulates, or otherwise mediates or controls the expression of the coding DNA. Promoter DNA and coding DNA may be from the same gene or from different genes, and may be from the same or different organisms. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET plasmids (Invitrogen, San Diego, Calif.), pCDNA3 plasmids (Invitrogen), pREP plasmids (Invitrogen), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

Suitable vectors include viruses, such as adenoviruses, adeno-associated virus (AAV), vaccinia, herpesviruses, baculoviruses and retroviruses, parvovirus, lentivirus, bacteriophages, cosmids, plasmids, fungal vectors, naked DNA, DNA lipid complexes, and other recombination vehicles typically used in the art which have been described for expression in a variety of eukaryotic and prokaryotic hosts, and may be used for gene therapy as well as for simple protein expression.

Lentiviral vectors have been reported to deliver genes to primary liver cells efficiently and permanently, integrating into the genome of non-dividing cells such as primary liver cells (Lewis and Emerman "Passage through mitosis is required for oncoretroviruses but not the immunodeficiency virus" J. Virol. 1994, 68:510-6). Lentiviral vectors are described in, for example, Choi et al (2001, Stem Cells 2001; 19(3):236-46) or in U.S. Pat. No. 6,218,186.

Viral vectors, especially adenoviral vectors can be complexed with a cationic amphiphile, such as a cationic lipid, polyL-lysine (PLL), and diethylaminoethyldextran (DE-LAE-dextran), which provide increased efficiency of viral infection of target cells (See, e.g., PCT/US97/21496 filed Nov. 20, 1997, incorporated herein by reference). AAV vectors, such as those disclosed in Zhong et al., *J. Genet Syndr Gene Therapy* 2012 Jan. 10; S1. pii: 008, U.S. Pat. Nos. 5,139,941, 5,252,479 and 5,753,500 and PCT publication WO 97/09441, the disclosures of which are incorporated herein, are also useful since these vectors integrate into host chromosomes, with a minimal need for repeat administration of vector. For a review of viral vectors in gene therapy, see McConnell et al., 2004, Hum Gene Ther. 15(11):1022-33; Mccarty et al., 2004, Annu Rev Genet. 38:819-45; Mah et al., 2002, Clin. Pharmacokinet. 41(12): 901-11; Scott et al., 2002, Neuromuscul. Disord. 12(Suppl 1):S23-9.

Pharmaceutical Compositions

The present invention further provides pharmaceutical compositions which comprise an HNF4α agonist, e.g., all or portions of HNF4α polynucleotide sequences, HNF4α polypeptides or functional fragments thereof, small molecule, or other HNF4α agonists, alone or in combination with at least one other agent, such as a stabilizing compound, and may be administered in any sterile, biocompatible pharmaceutical carrier, including, but not limited to, saline, buffered saline, dextrose, and water. The composition may be in a liquid or lyophilized form and comprises a diluent (Tris, citrate, acetate or phosphate buffers) having various pH values and ionic strengths, solubilizer such as Tween or Polysorbate, carriers such as human serum albumin or gelatin, preservatives such as thimerosal, parabens, benzylalconium chloride or benzyl alcohol, antioxidants such as ascrobic acid or sodium metabisulfite, and other components such as lysine or glycine. Selection of a particular composition will depend upon a number of factors, including the condition being treated, the route of administration and the pharmacokinetic parameters desired. A more extensive survey of components suitable for pharmaceutical compositions is found in Remington's Pharmaceutical Sciences, 18th ed. A. R. Gennaro, ed. Mack, Easton, Pa. (1980).

The methods of the present invention find use in treating hepatic failure or cirrhosis. Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy. The route of administration eventually chosen will depend upon a number of factors and may be ascertained by one skilled in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, a therapeutically effective amount of an HNF4α agonist is that amount that increases expression of liver-specific genes, increases CYP activity, increases liver function, improves liver histology (e.g., fibrosis), treats or prevents cirrhosis, or prolongs survival in a subject suffering from liver failure. The amount will vary from one individual to another and will depend upon a number of factors, including the overall physical condition of the patient, severity and the underlying cause of liver failure and/or cirrhosis.

A target liver function can be determined by a liver function test, which typically measures, for example, albumin, total bilirubin, direct bilirubin, and/or INR Prothombin Time. The clinical signs of protein dysfunction, manifested by hepatic encephalopathy (which can be measured by an elevated arterial ammonia level), and muscle wasting are manifestations of hepatocyte failure, which can be made worse by portal hypertension. Therefore, improvement in liver function can also be assessed by the presence or absence of fibrosis in the liver, ascites, muscle wasting, ammonia levels, neurologic function (hepatic encephalopathy), etc. in the subject. Liver biopsy, such as a needle biopsy, can be used to assess the degree of fibrosis and cirrhosis of the liver. It is understood that such targets will vary from one individual to another such that physician discretion may be appropriate in determining an actual target liver function for any given patient. Nonetheless, determining a target liver function is well within the level of skill in the art.

The formulations of the invention can be administered for prophylactic and/or therapeutic treatments. For example, in alternative embodiments, pharmaceutical compositions of the invention are administered in an amount sufficient to treat, prevent and/or ameliorate liver failure and/or cirrhosis. As is well known in the medical arts, dosages for any one patient depends upon many factors, including stage of the disease or condition, the severity of the disease or condition, the patient's size, body surface area, age, the particular compound to be administered, sex, time and route of administration, general health, and interaction with other drugs being concurrently administered.

Accordingly, in some embodiments of the present invention, HNF4α nucleotide and HNF4α amino acid sequences or other HNF4α agonists can be administered to a patient alone, or in combination with one or more other nucleotide sequences, drugs, lifestyle changes, etc. used in the treatment or prevention of liver failure and/or cirrhosis or symptoms thereof (for example, interferon therapy, diuretic drugs, transjugular intrahepatic portosystemic shunt (TIPS), paracentesis, antibiotics, drugs for the prevention of variceal bleeding, lactulose, changes to diet, and/or abstinence from alcohol) or in pharmaceutical compositions where it is mixed with excipient(s) or other pharmaceutically acceptable carriers. In one embodiment, the HNF4α agonist is administered in a subject as a bridge to liver transplantation.

In one embodiment of the present invention, the pharmaceutically acceptable carrier is pharmaceutically inert. In another embodiment of the present invention, HNF4α polynucleotide sequences or HNF4α amino acid sequences or other HNF4α agonists may be administered alone to individuals subject to or suffering from liver failure and/or cirrhosis. The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Single or multiple administrations of formulations can be given depending on the dosage and frequency as required and tolerated by the patient. The formulations should provide a sufficient quantity of active agent to effectively treat, prevent or ameliorate or liver failure and/or cirrhosis or symptoms thereof as described herein. For example, an exemplary pharmaceutical formulation for oral administration can be in a daily amount of between about 0.1 to 0.5 to about 20, 50, 100 or 1000 or more µg per kilogram of body weight per day of protein. In an alternative embodiment, dosages are from about 1 mg to about 4 mg per kg of body weight per patient per day of protein are used. For example, in one embodiment a therapeutically effective amount of a polypeptide of this invention is a dosage of between about 0.025 to 0.5 milligram per 1 kilogram of body weight of the patient; or, a therapeutically effective amount is a dosage of between about 0.025 to 0.2 milligram, or 0.05 to 0.1 milligram, or 0.075 to 0.5 milligram, or 0.2 to 0.4 milligram, of the compound per 1 kilogram of body weight of the patient. In another embodiment, a single dose is sufficient to achieve the desired results.

In one embodiment, the HNF4α agonists of the invention are administered once, twice, or three times per week for all indications except the surgery indication, by intravenous (IV) or subcutaneous (SC) injection to reach a suggested target liver function range. Once the target liver function has been achieved, a maintenance dosing schedule is established which will vary depending upon the patient.

Toxicity and therapeutic efficacy of such compounds can be determined by standard pharmaceutical procedures in cell cultures or experimental animals (LD50, the dose lethal to 50% of the population; and ED50, the dose therapeutically effective in 50% of the population). The dose ratio between toxic and therapeutic effects is the therapeutic index, and it can be expressed as the ratio LD50/ED50. Compounds that exhibit large therapeutic indices are preferred. The data obtained from these cell culture assays and additional animal studies can be used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The following Example is offered to more fully illustrate the invention, but is not to be construed as limiting the scope thereof.

Example 1: Upregulation of HNF4α to Treat Hepatic Failure

This Example illustrates that end-stage cirrhotic hepatocytes, previously considered to be senescent and irreversibly dysfunctional, can revert to normal function following transduction with nucleic acid encoding the transcription factor HNF4α, even though surrounded by an abnormal extracellular matrix. As described herein, HNF4α reexpression immediately corrected the phenotype of cultured cirrhotic hepatocytes and reversed terminal end-stage cirrhosis and liver failure in vivo.

More than a decade ago, the inventors developed a unique model in rats, using chronic administration of $CCl_4$, to produce a syndrome of cirrhosis and progressive liver failure that greatly resembles human disease (11). While the latter has different etiologies that include HBV, HCV, alcohol, or NASH/metabolic syndrome, the $CCl_4$-injured rat reproduces the most important feature of advanced cirrhosis, the irreversibly decompensated hepatocyte.

Previously, the inventors analyzed the transcriptome of hepatocytes recovered from advanced cirrhotic livers (http://www.ncbi.nlm.nih.gov/geo/query/acc.cgi?acc=GSE22977; Liu L, Yannam G R, Nishikawa T, Yamamoto T et al. Hepatology 2012 May; 55(5):1529-39, the contents of which are expressly incorporated herein by reference) and also transplanted them. Microarrays showed marked decreases in the expression of HNF4α, Foxa2, C/EBPα, and HNF1α, molecules that are part of the network of hepatocyte-enriched transcription factors, sequentially established during development, that regulate the mature hepatocyte phenotype, controlling expression of proteins of coagulation, biliary metabolism, and lipid metabolism (12, 13). Transplantation of hepatocytes from end-stage cirrhotic rats into non-cirrhotic host livers eventually restored their regenerative capacity (14), but the delay in restoration suggested that the process was not the simple expansion of engrafted cells that occurs with normal regeneration.

Since deficient transcription factors could explain hepatocyte impairment, the inventors investigated the therapeutic effects of forced re-expression. HNF4α was chosen for this therapy because it is the central regulator of the hepatocyte transcription factor network, has no other hepatocyte homolog, and showed the greatest reduction in the decompensated hepatocyte (FIG. 1A).

As described herein, cirrhosis was induced in Lewis rats by treatment with phenobarbital and carbon tetrachloride ($CCl_4$). Animals treated for 14 weeks had normal liver function (compensated cirrhosis), whereas 26-28 weeks of CCl$_4$ produced decompensated liver function with elevated bilirubin, decreased albumin, prolonged prothrombin time, and hepatic encephalopathy scores of 8±0.7 vs. a normal score of 15 (11). All animals were assessed for liver function 4 weeks after receiving their last dose of CCl$_4$ to guarantee that alterations in liver function were not the consequence of the acute effects of CCl$_4$ administration.

To confirm the inventors' previous microarray studies (Liu L, Yannam G R, Nishikawa T, Yamamoto T et al. Hepatology 2012 May; 55(5):1529-39), a detailed analysis of the expression of HNF4α and its target genes in isolated hepatocytes and liver tissue was performed. qRT-PCR analysis confirmed severe downregulation of HNF4α expression, and quantification of HNF4α in hepatocytes by Western blot and by immunofluorescent staining of cytospin samples gave similar results (FIG. 1B-D). Immunohistochemical localization of HNF4α showed expression in nuclei of hepatocytes but not in bile duct or other non-parenchymal cells. Nuclear HNF4α was present in the majority of hepatocytes from animals with compensated cirrhosis but was severely diminished in hepatocytes in the nodular livers of decompensated cirrhosis, where it selectively localized to the periportal region. Down-regulation of HNF4α expression has also been reported in human cirrhosis (15, 16). Thus, a significant decrease of HNF4α in hepatocytes correlates with decompensation in cirrhosis. As HNF4α affects the expression of many liver-specific target genes involved in glucose, lipid, amino acid, xenobiotic, and drug metabolism (17), the expression of α1-antitrypsin; apolipoproteins A2, C3, and E; cytochrome P450 3a23, coagulation factor VII, hepatocyte nuclear factor 1α, ornithine transcarbamylase, tyrosine aminotransferase, tryptophan 2,3-dioxygenase, transferrin, and transthyretin was evaluated (FIG. 1E). All of these genes were severely down-regulated in advanced cirrhosis in parallel to HNF4α.

Figure 2:
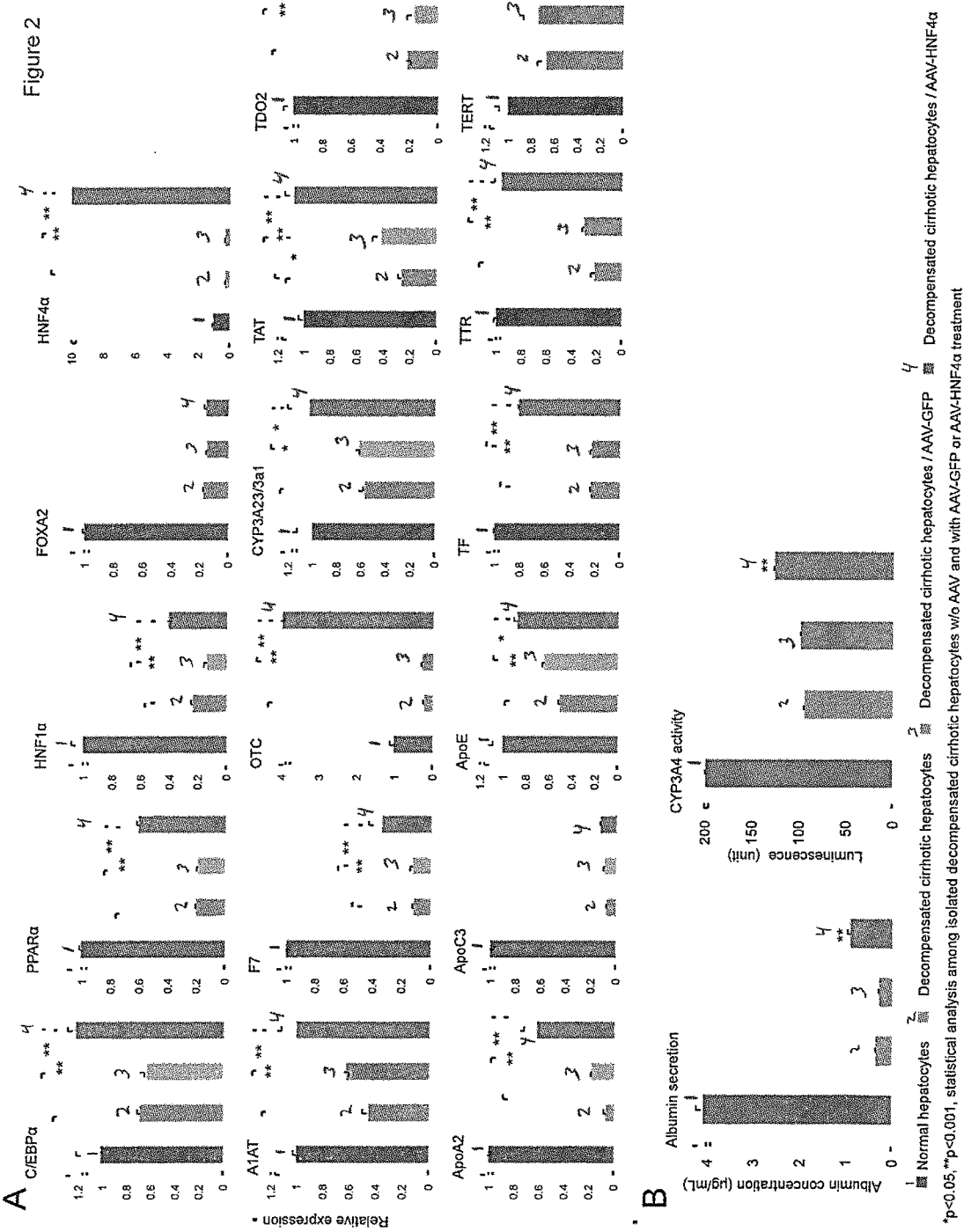

To assess whether forced reexpression of HNF4α could affect the function of cirrhotic hepatocytes, in vitro culture system was first used. Hepatocytes, isolated from animals with cirrhosis and decompensated liver function, were transduced with adeno-associated virus (AAV) vectors to express HNF4α and GFP or GFP alone. At 48 hours, qRT-PCR analysis showed HNF4α reexpression restored to nearly normal levels the hepatic transcription factors C/EBPα, HNF1α, and PPARα, and the phenotypic targets genes important for liver-specific activity (FIG. 2A). HNF4α expression also improved secretion of albumin into the culture supernatant—severely impaired in hepatocytes isolated from decompensated cirrhosis (14)—and activity of Cytochrome P450 3A4, a major enzyme of xenobiotic metabolism (FIG. 2B).

Figure 3:
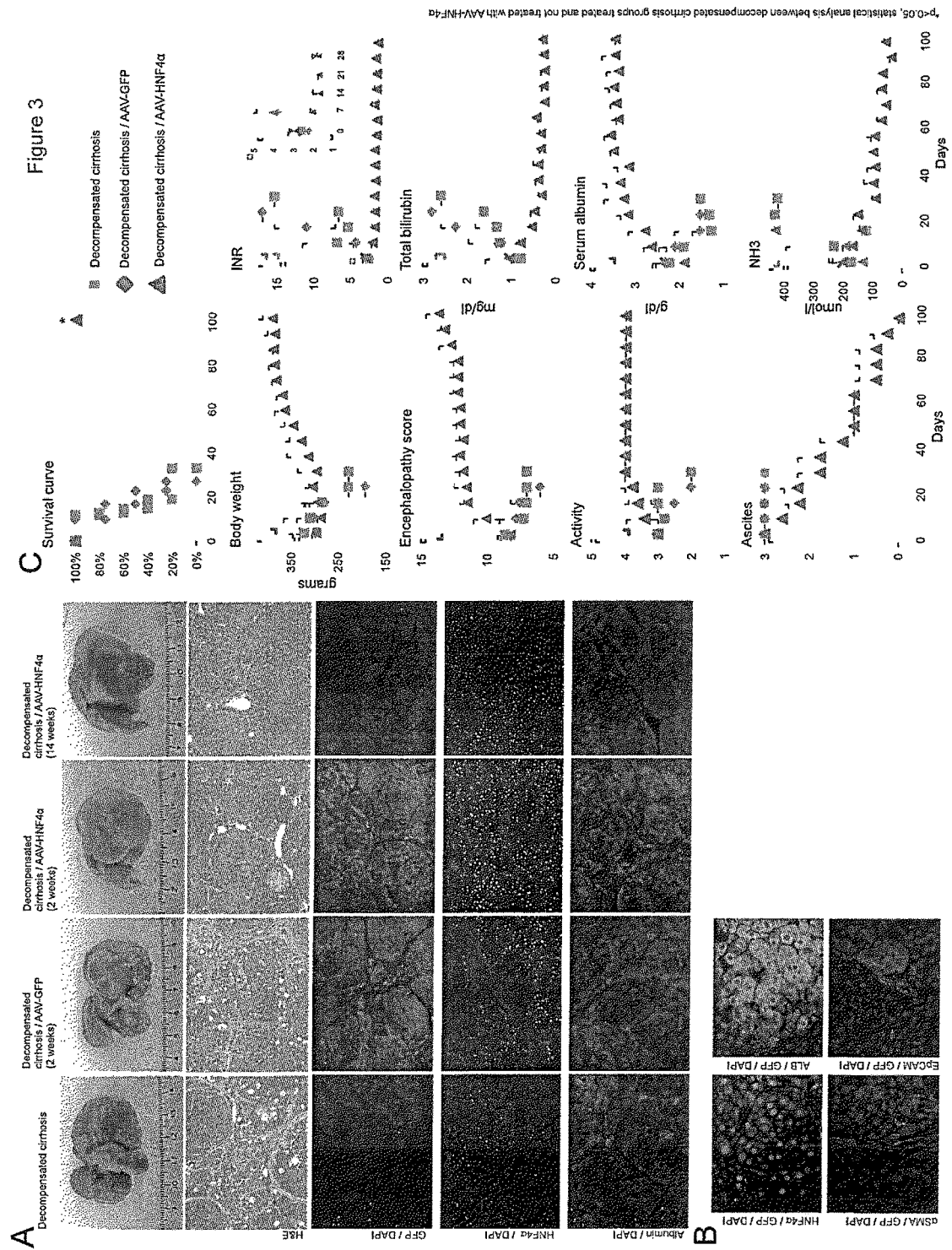
FIGS. 3A-C. Effect of HNF4α re-expression in rats with decompensated cirrhosis and liver failure. (A) Gross and microscopic (hematoxylin & eosin and fluorescence staining) assessment of decompensated cirrhotic livers two and fourteen weeks after intervention. Cirrhotic rats with continued severe liver failure, four weeks after their last dose of CCL4, were given a recombinant AAV expressing either HNF4α and GFP or GFP only; microscopic magnification ×100. (B) Fluorescence staining for GFP and co-staining for hepatocyte (albumin) or non-parenchymal liver cell (α-SMA and EpCAM) markers; magnification ×200. (C) Survival and clinical parameters of liver failure in control, AAV-GFP and AAV-HNF4α-GFP-treated animals with decompensated cirrhosis.

In previous studies using this model of decompensated liver failure from cirrhosis, it was shown by the inventors that after withdrawal of CCl$_4$ and a four-week observation period, 100% of untreated animals die of progressive hepatic failure in 2 to 3 weeks. Intrasplenic hepatocyte transplantation dramatically improved function and survival, but was only effective for a period of weeks to months (11,18) despite transplantation with syngeneic hepatocytes. The therapeutic benefit was moderate, since the end-stage cirrhotic rats still died of progressive hepatic failure and persistent severe cirrhosis. With this background, animals with liver failure and cirrhosis were transduced to re-express HNF4α in their hepatocytes by intravenous infusion of 3×10$^{11}$ AAV-HNF4α-GFP genomes. Animals sacrificed 2 weeks after infusion demonstrated high transduction efficiency uniformly distributed in most hepatocytes. Moreover, the impaired albumin expression of decompensated cirrhosis was dramatically improved and its expression increased until the time of sacrifice at 100 days following the observation period (FIG. 3A). Administration of the AAV-GFP control vector did not affect liver function. Co-staining for GFP, albumin, α-smooth muscle, and EpCam indicated transduction of approximately 60-80% of hepatocytes, but not non-parenchymal cells (FIG. 3B). Pathophysiologic testing showed striking and persistent improvement in liver function, ascites, activity, and neurologic function, and survival was prolonged to the end-point of the study at 100 days post observation after CCl$_4$ withdrawal (FIG. 3C).

Figure 4:
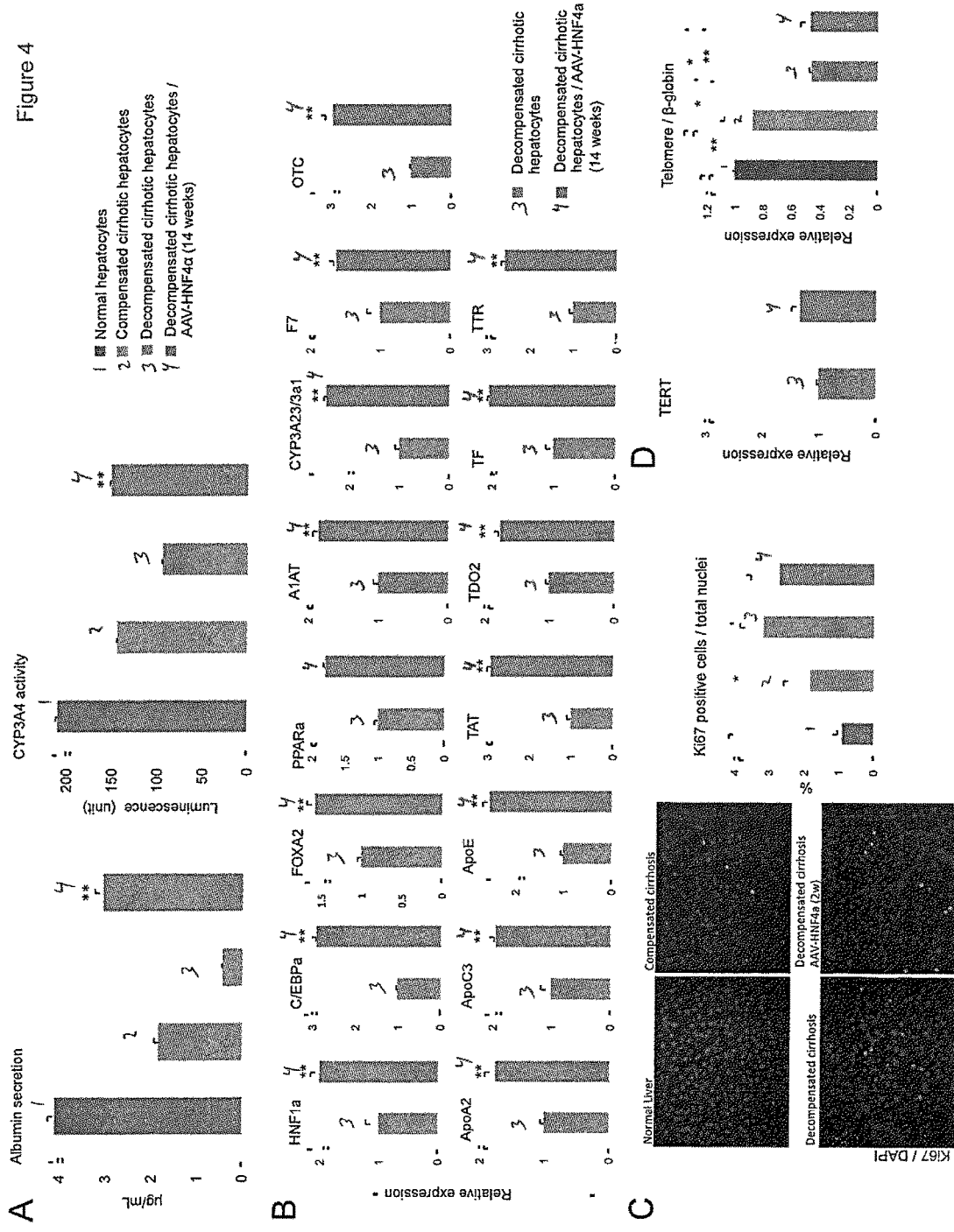
FIGS. 4A-D. Characterization of hepatocytes recovered from treated decompensated cirrhotic rats after HNF4α re-expression. (A) Albumin synthesis and Cytochrome P450 (CYP3A4) activity in decompensated cirrhotic hepatocytes recovered 14 weeks after AAV-HNF4α/GFP treatment. Hepatocytes recovered from normal livers and compensated cirrhotic livers were used as controls. (B) qRT-PCR analysis of hepatocyte transcription factor network and hepatocyte-specific gene expression in hepatocytes recovered from decompensated cirrhotic livers and decompensated cirrhotic livers 14 weeks after AAV-HNF4α/GFP treatment. (C) Fluorescence staining for Ki67, a proliferation marker, and it's quantification in AAV-HNF4α-GFP-treated decompensated cirrhotic hepatocytes; magnification ×200 (D) qRT-PCR analysis for TERT expression and telomere length by genomic DNA analysis.
Figure 5:
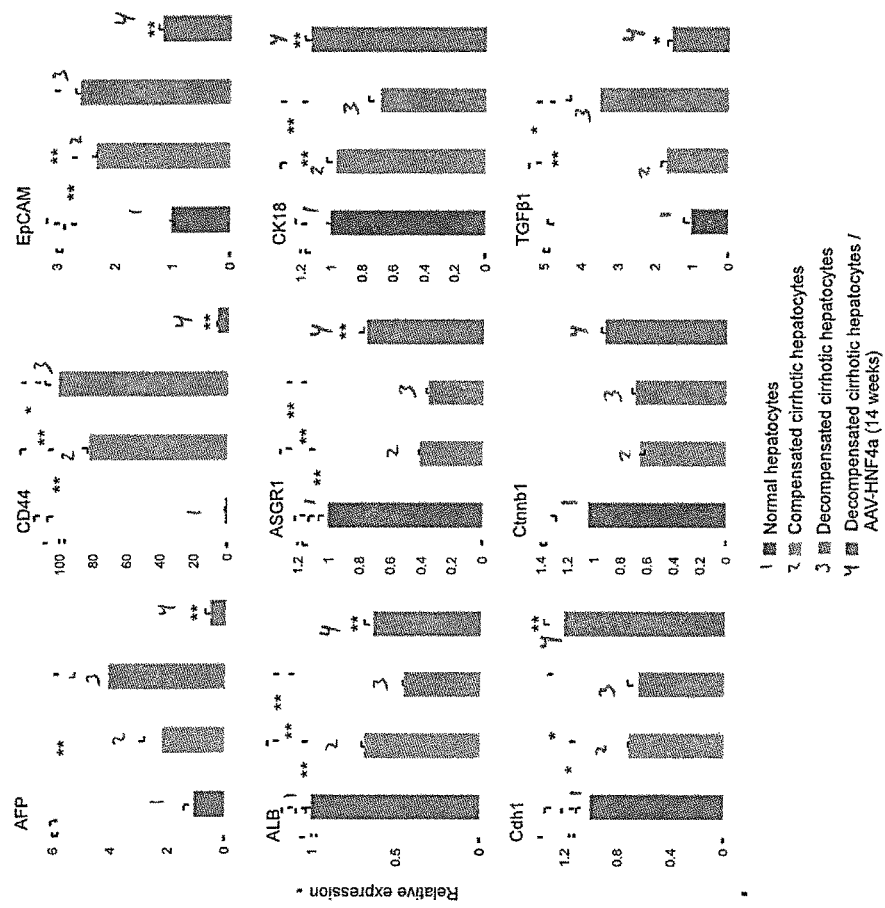
FIG. 5. Effect of HNF4α re-expression on expression of hepatic progenitor and liver-specific genes in hepatocytes from decompensated cirrhotic livers. qPCR analyses of hepatic progenitor markers (AFP, CD44 and EpCAM), mature hepatic specific genes (Albumin, ASGPR1, CK18), epithelial cell related genes (Cdh1 and Ctnnb1) and the protein TGFβ1. Each value represents the mean±SD. Statistical analysis was performed among three groups (normal, compensated and decompensated cirrhotic hepatocytes) and between un-treated decompensated cirrhotic hepatocytes and decompensated cirrhotic hepatocytes 14 weeks after in vivo HNF4α re-expression (*p<0.05,**P<0.001).

Functional analysis of cells isolated from treated animals showed significant improvement of albumin secretion and CYP3A4 activity (FIG. 4A). In addition, there was improvement in expression levels of HNF4α target genes (FIG. 4B) and decreased expression of the hepatic progenitor cell markers AFP, CD44, and EpCAM (FIG. 5). The healing effects of HNF4α reexpression did not depend on proliferation, since there was no increase apparent in Ki67 staining (FIG. 4C). HNF4α did not significantly augment TERT expression and telomere length in the cirrhotic hepatocytes remained critically short (FIG. 40). Thus, HNF4α acted by phenotypically correcting diseased hepatoctyes, not by stimulating their replacement.

Figure 6:
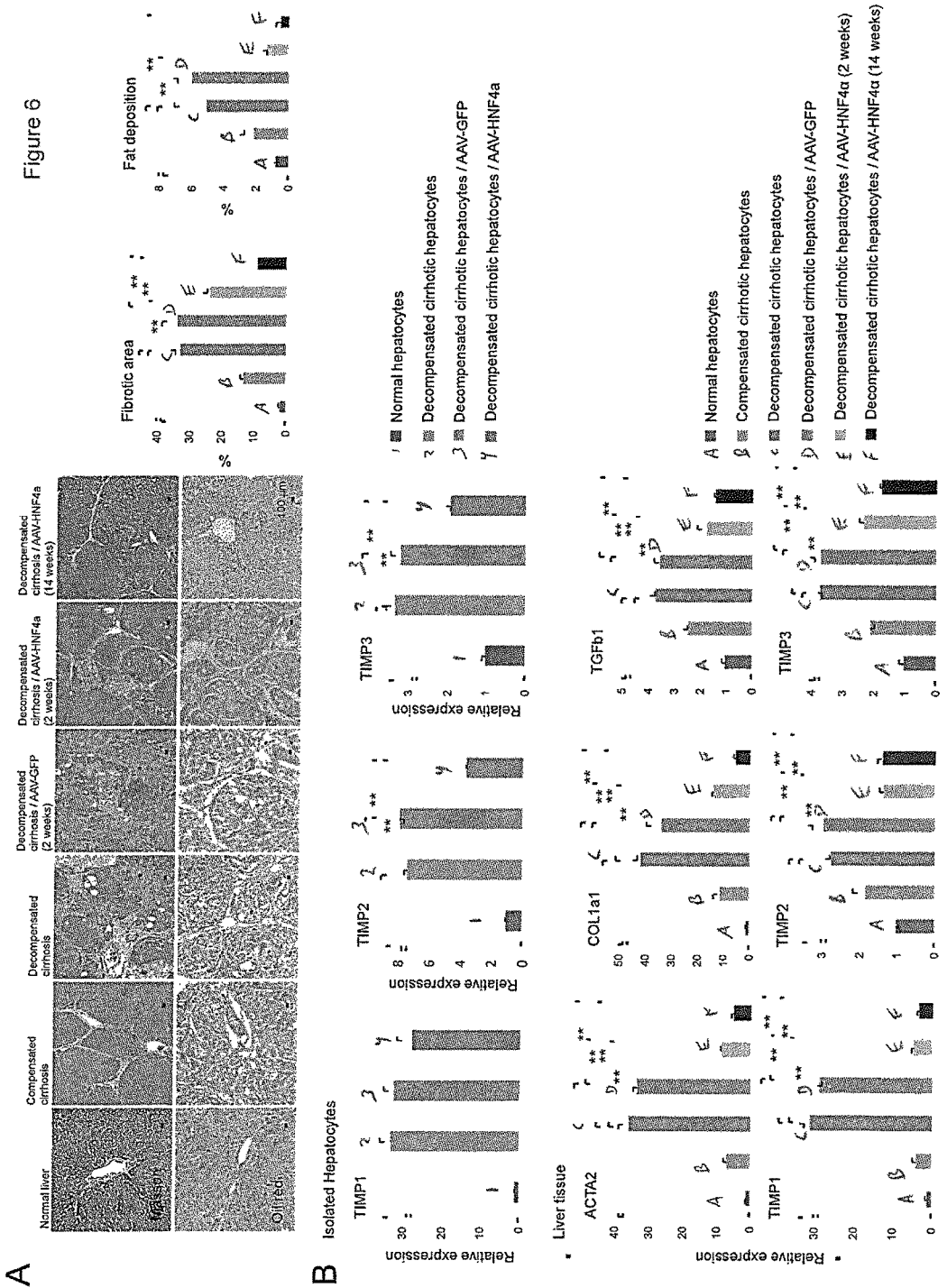
FIGS. 6A-B. Effect of HNF4α re-expression on histology and fibrosis-related genes in rats with decompensated cirrhosis and liver failure. (A) Masson and oil red stained photomicrographs with quantification of fibrosis and fat deposition in decompensated cirrhotic rat livers two and fourteen weeks after AAV-HNF4α/GFP therapy. Normal control, compensated cirrhotic and un-treated or AAV-GFP treated decompensated cirrhotic livers were used as controls. Fibrosis and fat deposition decreased significantly two and fourteen weeks after HNF4α re-expression. Magnification ×100 (B) qPCR analysis of fibrosis-related genes (TIMP1, TIMP2, TIMP3, ACTA2, COL1a1, and TGFβ1) from isolated hepatocytes and tissue recovered from decompensated cirrhotic livers. HNF4α re-expression induced down regulation of TIMP2 and TIMP3. Each value represents the mean±SD. Statistical analysis was performed among four groups (control decompensated cirrhotic hepatocytes, and decompensated cirrhotic hepatocytes 2 after AAV-GFP treatment, or 2 and 14 weeks after AAV-HNF4α/GFP treatment (*p<0.05,**P<0.001).

The corrected hepatocytes had a striking extrinsic effect on the extracellular matrix, because the fibrotic remodeling of the liver, the hallmark of cirrhosis, was also corrected. Histologic studies showed improvement in fat deposition and fibrosis as early as 2 weeks following treatment with AAV-HNF4α-GFP and significant further improvement at 100 days (FIG. 3, FIG. 6A), results that are in sharp contrast to the inventors' previous experience with hepatoctye transplantation (11, 18). Expression of TIMP1-3, natural inhibitors of metalloproteinases that degrade the extracellular matrix, and TGFβ, a hepatocyte-secreted cytokine that stimulates fibrogenesis was also investigated. TIMP2 and TIMP3 expression was immediately down-regulated in vitro following HNF4α re-expression, while TGFβ and TIMPs 1, 2, and 3 were down-regulated within 2 weeks of HNF4α transduction in cirrhotic rats (FIG. 6B).

These studies show that down-regulation of HNF4α has a profound effect on the end-stage cirrhotic hepatocyte in vitro, since replenishment of this single factor immediately revitalizes function. Moreover, transduction of hepatocytes in cirrhotic animals with apparently irreversible decompensated function produced a profound and immediate improvement in hepatic function. Normalization of function took place in two weeks while portal hypertension, evidenced by the presence of ascites, regressed when histological reversal of cirrhosis was more complete. This outcome is consistent with the central role of HNF4α within the hepatocyte transcription factor network (12, 20, 21). Impaired expression of HNF4α could reflect direct regulation or inhibition of another network factor that activates HNF4α transcription (22-24) and could result from either cell-extrinsic or cell-intrinsic mechanisms. Toxins, chemical injury, and cytokines generated from inflammation or injured cells can all induce inhibition of critical transcription factors (25). Such extrinsic mechanisms should be corrected immediately by removing the injury in vivo, or by culturing the hepatocytes in vitro. However, neither withdrawing CCl$_4$ nor primary cell culture effectively reversed the hepatocyte dysfunction. Since down regulation of network factors HNF1α, FOXA2, CEBPα, and PPARα was also clear in these studies, it is likely that HNF4α, or another network gene, is the critical target of an inhibitory pathway. These data indicate the target is HNF4α, since its reexpression restores the other three factors. Research on hepatocyte injury has highlighted three candidate pathways that could mediate this inhibition—TNFα-NFκB, IL6-Stat3, and TGFβ-SMAD—and the inventors' preliminary research showed NFκB and TGFβ signatures by microarray and direct transcript analysis (26). Thus, it is likely that cytokine/injury effects alter expression of the hepatocyte transcription factor network by extrinsic mechanisms, with the result that network factors establish a new steady-state equilibrium in the dysfunctional hepatocyte that can no longer compensate to restore normal gene expression. This has important therapeutic implications, because it may require only transient therapy with HNF4α to restore the transcription factor network once the injury has been moderated.

Further studies (see Example 3 below) will determine the efficacy of this intervention when there may be ongoing hepatocellular insults, as is the case with clinical cirrhosis, typically associated with hepatitis or alcohol abuse.

These studies indicate that in addition to regeneration mediated by expansion of mature hepatocytes or differentiation and expansion of induced progenitors, normalized function can be accomplished by transcriptional reprogramming with reversal of de-differentiation but not senescence. The results also indicate that HNF4α therapy could be effective in treating advanced liver cirrhosis with impaired hepatic function as a bridge to organ transplantation or possibly even as destination therapy.

Material and Methods

Animals: Lewis rats were obtained from Charles River Laboratory (Cambridge, Mass.). and were maintained in isolation cages in the Department of Laboratory and Animal Resources at the University of Pittsburgh. Animals were housed in temperature- and light-dark cycle-controlled rooms. All procedures performed on animals were approved by the University of Pittsburgh Animal Care and Use Committees, and thus within the guidelines for humane care of laboratory animals.

Induction of liver cirrhosis: Liver cirrhosis was induced as described beginning in four-week-old inbred male Lewis rats, weighing 100 to 130 g, using Phenobarbital (Sigma Chem. Co. St. Louis, Mo.) and carbon tetrachloride ($CCl_4$, Sigma) (27). Rats were given Phenobarbital (0.5 g/L) added to the drinking water. Starting two weeks later, $CCl_4$ (diluted 1:9 in the olive oil) was administered by gavage on a full stomach twice a week, Following an initial dose of 0.2 ml/kg each subsequent dose was adjusted weekly on the basis of changes in body weight. If the body weight increased or remained unchanged $CCl_4$ was continued at 0.2 ml/kg twice weekly. When body weight decreased by 1-5 g the dose of $CCl_4$ was reduced to 0.15 ml/kg, and if body weight decreased by 6-10 g the $CCl_4$ was reduced to 0.1 ml/kg. In rats that lost more than 10 g of body weight, $CCl_4$ was withheld until reassessment one week later. All animals were monitored by body weight, activity, amount of ascites, and by hepatic encephalopathy (HE) score, which constituted a coma scale based on spontaneous levels of flexion, grasping, righting, placement, corneal, and head-shaking reflexes. Normal activity score was 5; maximum ascites score was 3; and a HE score of 15 indicated normal behavior (28). Whole blood was obtained at different time points and analyzed for bilirubin and albumin using a microfluidic metabolic assay system (Picollo-Abaxis, Union City, Calif.). Ammonia (NH3) and INR in serum were measured in the clinical laboratory at the Children's Hospital of Pittsburgh.

When rats received a minimum of 2.6 ml $CCl_4$ and developed persistent ascites, an activity score of <4 and an HE score of <10, laboratory tests were performed weekly to estimate liver function. Phenobarbital and $CCl_4$ were discontinued when (1) plasma total bilirubin levels exceeded 0.5 mg/dl (normal <0.2 mg/dl); (2) the INR exceeded 1.7; (3) plasma ammonia concentrations were above 90 mmol/l (normal <70 mmol/1); (4) ascites was found to be persistent by clinical examination, and (5) the hepatic encephalopathy (HE) score was persistently <10. If four weeks after complete cessation of phenobarbital and carbon tetrachloride treatment, the laboratory measures, encephalopathy score and ascites did not improve, rats were considered to have chronic liver failure from decompensated cirrhosis. All animals receiving $CCl_4$ were observed for four weeks after receiving their last dose of $CCl_4$ to eliminate the acute effects of toxin exposure before hepatocytes were recovered for analysis and transplantation.

Animals required 2.8±0.2 mL $CCl_4$ over 26 to 28 weeks to generate cirrhosis that produced irreversible liver failure, and these animals died approximately 2-4 weeks after the four-week observation period with progressive worsening of liver function if they received no treatment. Animals with cirrhosis without liver failure received 13 to 14 weeks of $CCl_4$, and a total dose of 1.3±0.1 mL of $CCl_4$. Laboratory tests and ascites resolved quickly in all of these animals after the four week observation period after discontinuing carbon tetrachloride.

Isolation of hepatocytes: Hepatocytes were isolated from donor rats by in situ collagenase perfusion as originally described by Berry and Friend and later modified by Seglen (29, 30). Briefly, a 20 G cannula (Becton, Dickinson Infusion Therapy Systems Inc., Sandy, Utah) was inserted into the portal vein. Perfusion using 0.5 mM EGTA in Leffert's buffer was started via the portal vein for 10 minutes, and the inferior vena cava (IVC) was cut for drainage. The liver was then perfused with collagenase (Liberase, Roche, Germany) at 21 units/200 mL in Leffert's solution for 10 minutes. The perfusion time varied from 10 to 20 minutes based on the consistency of liver tissue in response to collagenase digestion. After perfusion, the liver was excised and chopped into small millimeter sized pieces using a scalpel in a 10 cm sterile tissue culture dish. Cells were then collected in Leffert's solution containing 2.5 mM $CaCl_2$ and filtered through a 200 micron nylon mesh to remove aggregated cells and residual tissue, centrifuged at 50 g for 3 minutes, and washed three times with chilled Dulbecco's Modified Eagle's Medium (DMEM). Viability was assessed by Trypan blue exclusion and by plating efficiency at 24 hours. Cell viability, as determined by trypan blue exclusion and plating efficiency, was required to be 80% or greater to be acceptable for in vitro analysis. For cytospin samples, $5 \times 10^4$ hepatocytes were centrifuged at 50 g for 5 minutes for attachment to slides. After air-drying, the cells were fixed with 4% paraformaldehyde for 15 minutes and preserved at −80° C.

Hepatocyte culture: Five hundred thousand hepatocytes isolated from control and cirrhotic livers were seeded into individual wells of collagen-coated 6-well plates (Becton Dickinson Labware, NJ) and cultured at 37° in 5% $CO_2$ in F-12 medium (DMEM supplemented with 5% FBS, 2 mM Glutamine, 100 U/mL Penicillin, 100 ug/mL Streptomycin, 100 nM dexamethasone, 0.872 uM insulin and 5 ng/mL epithelial growth factor). Tissue culture medium was changed after overnight culture following the isolation and freshly exchanged everyday. The supernatant was collected 24 hours later to determine albumin secretion.

Total RNA extraction and quantitative real-time PCR (QPCR): RNA was extracted from isolated rat hepatocytes or liver tissue using the RNeasy Mini Kit (QIAGEN, Valencia Calif.) according to the manufacturer's instructions. RNA quantity and integrity were evaluated using a NANO DROP 1000 spectrometer (Thermo Fisher Scientific Inc). cDNA was reverse transcribed from 1 ug total RNA using SuperScript III reverse transcriptase (Invitrogen). Each gene expression was measured using Power SYBR Green PCR Master Mix (Applied Biosystems, Foster, Calif., USA), using a ABI 7500 real time PCR System. The sequences of the primers used for this Example are listed in Table 1.

TABLE 1

Primer sequences

| Primer Name | Primer sequence | Length of PCR product |
|---|---|---|
| HNF4a-F | 5'-ATGGACATGGCTGACTACAGTGCT-3' (SEQ ID NO: 13) | 204 bp |
| HNF4a-R | 5'-ACAGCTTGAGGCTCCGTAGTGTTT-3' (SEQ ID NO: 14) | |
| A1AT-F | 5'-TCTAGAGGGCCTGGAGTTCA-3' (SEQ ID NO: 15) | 99 bp |
| A1AT-R | 5'-TCACTGTCTGGCCTCTTGAG-3' (SEQ ID NO: 16) | |
| ACTA2-F | 5'-TTCAATGTCCCTGCCATGTA-3' (SEQ ID NO: 17) | 94 bp |
| ACTA2-R | 5'-CATCTCCAGAGTCCACCACA-3' (SEQ ID NO: 18) | |
| ACTB-F | 5'-TTGCTGACAGGATGCAGAAG-3' (SEQ ID NO: 19) | 122 bp |
| ACTB-R | 5'-CAGTGAGGCCAGGATAGAGC-3' (SEQ ID NO: 20) | |
| AFP-F | 5'-GCCCAGCATACGAAGAAAACA-3' (SEQ ID NO: 21) | 176 bp |
| AFP-R | 5'-TCTCTTTGTCTGGAAGCATTCCT-3' (SEQ ID NO: 22) | |
| ALB-F | 5'-TCTGCACACTCCCAGACAAG-3' (SEQ ID NO: 23) | 114 bp |
| ALB-R | 5'-AGTCACCCATCACCGTCTTC-3' (SEQ ID NO: 24) | |
| ApoA2-F | 5'-GGCAAGGATTTGATGGAGAA-3' (SEQ ID NO: 25) | 108 bp |
| ApoA2-R | 5'-CCCAGTTCTCTGGACAAAGG-3' (SEQ ID NO: 26) | |
| ApoC3-F | 5'-ACATGGAACAAGCCTCCAAG-3' (SEQ ID NO: 27) | 75 bp |
| ApoC3-R | 5'-TGGCCACCACAGCTATATCA-3' (SEQ ID NO: 28) | |
| ApoE-F | 5'-TGAACCGCTTCTGGGATTAC-3' (SEQ ID NO: 29) | 85 bp |
| ApoE-R | 5'-TGTGTGACTTGGGAGCTCTG-3' (SEQ ID NO: 30) | |
| ASGR1-F | 5'-GGAGGATCTGAGGGAAGACC-3' (SEQ ID NO: 31) | 125 bp |
| ASGR1-R | 5'-GGCAGCAGATCCTTTCAGAG-3' (SEQ ID NO: 32) | |
| CD44-F | 5'-TTTGGTGGCACACAGCTTG-3' (SEQ ID NO: 33) | 104 bp |
| CD44-R | 5-ATGGAATACACCTGCGTAACGG-3' (SEQ ID NO: 34) | |
| Cdh1-F | 5'-GAAGGCCTAAGCACAACAGC-3' (SEQ ID NO: 35) | 99 bp |
| Cdh1-R | 5'-AAGCACTTGACCCTGGTACG-3' (SEQ ID NO: 36) | |
| C/EBPa-F | 5'-GCCAAGAAGTCGGTGGATAA-3' (SEQ ID NO: 37) | 125 bp |
| C/EBPa-R | 5'-AACACCTTCTGCTGCGTCTC-3' (SEQ ID NO: 38) | |
| CK18-F | 5'-GCTCAGATCTTTGCGAATTC-3' (SEQ ID NO: 39) | 204 bp |
| CK18-R | 5'-CGCTTCGATTTCTGTCTCC-3' (SEQ ID NO: 40) | |
| COL1a1-F | 5'-TGGTCCTCAAGGTTTCCAAG-3' (SEQ ID NO: 41) | 123 bp |
| COL1a1-R | 5'-TTACCAGCTTCCCCATCATC-3' (SEQ ID NO: 42) | |
| Ctnnb1-F | 5'-TGCAGAAAATGGTTGCTTTG-3' (SEQ ID NO: 43) | 98 bp |
| Ctnnb1-R | 5'-GCTTTCCTGATTGCCGTAAG-3' (SEQ ID NO: 44) | |
| CYP3a23/3a1-F | 5'-ATGGAGATCACAGCCCAGTC-3' (SEQ ID NO: 45) | 130 bp |
| CYP3a23/3a1-R | 5'-CGATCTCCTCCTGCAGTTTC-3' (SEQ ID NO: 46) | |

TABLE 1-continued

Primer sequences

| Primer Name | Primer sequence | | Length of PCR product |
|---|---|---|---|
| EpCAM-F | 5'-TGAGAATGGTGAATGCCAGT-3' | (SEQ ID NO: 47) | 101 bp |
| EpCAM-R | 5'-GAGTCATCTCCGCCTTCATC-3' | (SEQ ID NO: 48) | |
| F7-F | 5'-TAACCCAGGAGGAAGCACAC-3' | (SEQ ID NO: 49) | 102 bp |
| F7-R | 5'-CTTCATTGCACTCCCTCTCC-3' | (SEQ ID NO: 50) | |
| Foxa2-F | 5'-CCATCCGTCATTCTCTCTCC-3' | (SEQ ID NO: 51) | 112 bp |
| Foxa2-R | 5'-TCGAACATGTTGCCAGAGTC-3' | (SEQ ID NO: 52) | |
| HNF1a-F | 5'-GACGTCTCCAGGTCTCAACC-3' | (SEQ ID NO: 53) | 119 bp |
| HNF1a-R | 5'-CACCCGTGTTAGTGAACGTG-3' | (SEQ ID NO: 54) | |
| OTC-F | 5'-CTCACCCTCAGCTGGATAGG-3' | (SEQ ID NO: 55) | 101 bp |
| OTC-R | 5'-CCCTTTGGAGTAGCTGCTTG-3' | (SEQ ID NO: 56) | |
| Ppara-F | 5'-AATGCAATCCGTTTTGGAAG-3' | (SEQ ID NO: 57) | 116 bp |
| Ppara-R | 5'-GCCAGAGATTTGAGGTCTGC-3' | (SEQ ID NO: 58) | |
| TAT-F | 5'-CATCGTGGACAACATGAAGG-3' | (SEQ ID NO: 59) | 101 bp |
| TAT-R | 5'-CAGGGTCTGTAGGCAGGTTC-3' | (SEQ ID NO: 60) | |
| TDO2-F | 5'-TTGAAGGGTCTGGAAGAGGA-3' | (SEQ ID NO: 61) | 119 bp |
| TDO2-R | 5'-TCATCGAACAAGCAGAGCAG-3' | (SEQ ID NO: 62) | |
| TERT-F | 5'-GCATCTGACCCGAGTCTCTC-3' | (SEQ ID NO: 63) | 105 bp |
| TERT-R | 5'-GAATGGCCTGAGCTTTTCAG-3' | (SEQ ID NO: 64) | |
| TF-F | 5'-AATGGAGATGGCAAAGAGGA-3' | (SEQ ID NO: 65) | 100 bp |
| TF-R | 5'-GAGAGCCGAACAGTTGGAAG-3' | (SEQ ID NO: 66) | |
| TGFb1-F | 5'-GGACTCTCCACCTGCAAGAC-3' | (SEQ ID NO: 67) | 100 bp |
| TGFb1-R | 5'-GACTGGCGAGCCTTAGTTTG-3' | (SEQ ID NO: 68) | |
| TIMP1-F | 5'-GGTTCCCTGGCATAATCTGA-3' | (SEQ ID NO: 69) | 99 bp |
| TIMP1-R | 5'-ATGGCTGAACAGGGAAACAC-3' | (SEQ ID NO: 70) | |
| TIMP2-F | 5'-TGGACGTTGGAGGAAAGAAG-3' | (SEQ ID NO: 71) | 97 bp |
| TIMP2-R | 5'-TCCCAGGGCACAATAAAGTC-3' | (SEQ ID NO: 72) | |
| TIMP3-F | 5'-TGTGCAACTTTGTGGAGAGG-3' | (SEQ ID NO: 73) | 84 bp |
| TIMP3-R | 5'-AATTGCAACCCAGGTGGTAG-3' | (SEQ ID NO: 74) | |
| TTR-F | 5'-TCGTACTGGAAGGCTCTTGG-3' | (SEQ ID NO: 75) | 120 bp |
| TTR-R | 5'-GTAGGAGTACGGGCTGAGCA-3' | (SEQ ID NO: 76) | |

* These primers were used for quantitative RT-PCR

The PCR reaction was programmed as follows: initial denaturing at 95° C. for 10 min followed by 95° C. for 15 sec, 60° C. for 1 min, cycled 40 times. The median cycle threshold value and the relative cycle threshold method were used for analysis. All cycle threshold values were normalized to the expression of the housekeeping gene ACTB. All reactions were performed with four biological replicates and three technical replicates with reference dye normalization. All values were normalized to control normal hepatocytes.

A p value of less than 0.05 was used for the significance cutoff point for all genes tested. ANOVA (Tukey-Kramer multiple comparison test) was used for statistical comparison within experimental groups. Each value represents the mean±SD.

DNA extraction and telomere length measurement by QPCR: Genomic DNA was extracted from isolated rat hepatocytes using the DNeasy Blood & Tissue Kit (QIAGEN, Valencia Calif.) according to the manufacturer's instructions. The samples were used for examination of telomere length in QPCR using the modified Cawthon's method (31). Briefly, telomere and single copy gene (β-globin) PCRs were performed in separate 96-well plates using the same DNA sample. The telomere/single copy gene (T/S) ratio was calculated as the index of telomere length in each sample. Triplicate PCR reactions for each sample were performed with Power SYBR Green PCR Master Mix, DNA and primer pairs using the ABI 7500 real time PCR System. Primers for telomeres and β-globin were added to a final concentrations of 250 nM. The primer sequences were tel-1, 5'-GGTTTTTGAGGGTGAGGGTGAGGGTGAGGGT-GAGGGT-3' (SEQ ID NO:77); tel-2, 5'-TCCCGACTATC-CCTATCCCTATCCCTATCCCTATCCCTA-3 (SEQ ID NO:78)'; β-globin-F, 5'-CAGCAAGTGGGAAGGTG-TAATCC-3' (SEQ ID NO:79); β-globin-R, 5'-CCCATTC-TATCATCAACGGGTACAA-3' (SEQ ID NO:80). PCR was performed at 95° C. for 10 min, followed by 40 cycles at 95° C. for 15 sec, and 54° C. for 2 min for the telomere reaction or 40 cycles at 95° C. for 15 sec, 60° C. for 60 sec for the β-globin reaction. Standard curves for both telomere length and the single copy gene were generated from five concentrations (42, 25.2, 15.1, 9.1, 5.4 ng/aliquot) of a reference DNA sample serially diluted 1.68 fold with PCR grade water.

Western blot analysis: Isolated hepatocyte fractions were lysed in RIPA buffer (Sigma Aldrich) with 1% proteinase inhibitor cocktail (Calbiochem) on ice. The supernatant was collected as cellular protein after centrifugation at 8000 g for 15 min. and the supernatant was preserved at −80° C. Forty micrograms of the cellular protein was electrophoresed in a 4-12% bis-tris gel and then transferred to a nitrocellulose membrane (Invitrogen). The immunological detection of HNF4α and beta-actin was performed as previously described. Antibodies for HNF4α and beta-actin were purchased from Abcam Inc. (Cambridge, Mass.) and Cell Signaling Technology, Inc. (Beverly, Mass.) respectively. After incubation with a horseradish peroxidase-conjugated secondary antibody for 1 h, immune detection of each band was performed with SuperSignal West Pico Chemiluminescent Substrate (PIERCE, Rockford, Ill.). The density of each band was measured using Image J software.

Histology: Five-micrometer-thick sections were prepared from paraffin embedded liver tissue fixed in 4% paraformaldehyde (PFA) and two slides each were used for hematoxylin and eosin (H & E) and Masson trichrome staining according to the manufacturer's protocols from Sigma. Oil red O staining was performed to detect cellular deposition of triglycerides using 5 micron sections from OTC compound embedded frozen liver tissues fixed in 2% PFA. Briefly, after fixation in 10% formaldehyde for 15 minutes at room temperature, sections were washed twice with deionized water for 1 minute, and then rinsed in 60% isopropanol for 1 minute. Subsequently, the sections were immersed in the oil red O working solution for 30 min at 37° C. After washing three times with deionized water, sections were counterstained using Gill's haematoxylin for 60 seconds to visualize nuclei. Sections were then rinsed with water for 10 min and mounted using crystal mount (Biomeda corp., Foster city, CA). Images were taken at low magnification (100×) using an Olympus Provis light microscope. To quantify detection of fibrotic areas in the Masson trichrome stained sections or fat deposition on oil red O stained sections, the signal intensity was measured over five different fields using Image J software and the average value was used as the semi-quantitative measurement of fibrosis or fat deposition within the liver.

Immunohistochemistry: Sections, five-microns in thickness, were heated in a microwave oven in citrate sodium buffer, pH6.0 (DAKO, CA) for 5-10 minutes at 95° C., and cooled at room temperature for 20 minutes. After blocking with PBS and 2% FCS for 15 minutes, samples were incubated with one or a combination of diluted primary antibodies (1:100) for 1 hour at room temperature. After washing three times in PBS, samples were incubated with diluted secondary antibodies conjugated with fluorochromogen (1:250) for 60 minutes at room temperature for immunofluorescence staining. Samples were then finally mounted in VECTASHIELD (Vector Laboratories, Inc., Burlingame, Calif.) containing DAPI solution. Immunohistochemistry was also performed using the same method described above, except for the blocking of endogenous peroxydase by incubation in methanol and 0.3% hydroxyperoxydase for 20 minutes. The VECTASTAIN ABC kit for mouse IgG (Vector Laboratories, Inc) was used to detect the immunocomplex signal and the samples were counterstained using Gill's haematoxylin for 60 seconds. The stained samples were examined using Olympus Provis light microscope. Mouse anti-HNF4α monoclonal antibody, rabbit anti-GFP polyclonal antibody, rabbit anti-Epcam polyclonal antibody, rabbit Ki67 polyclonal antibody, mouse anti-alpha smooth muscle actin monoclonal antibody were purchased from Abcam Inc., mouse anti-GFP monoclonal antibody from Cell Signaling Technology, Inc. and sheep anti-rat albumin polyclonal antibody from Bethyl Laboratories, Inc. (Montgomery, Tex.) as primary antibodies in this study. Alexa Fluor 488-conjugated goat anti-rabbit IgG and anti-mouse IgG antibodies and Alexa Fluor 594-conjugated goat anti-rabbit IgG, anti-mouse IgG and donkey anti-sheep IgG antibody were purchased from Invitrogen as secondary antibodies. For calculation of percent positive cells at least four low power digital images (100×) per sample were analyzed using an Olympus Provis light microscope using ImageJ software.

AAV cloning and virus preparation: Two AAV vectors were used for these studies; one capable of expressing GFP from an IRES promoter, pAAV-GFP, and the other capable of expressing HNF4α under control of a CMV promoter and GFP under control of the IRES promoter, pAAV-HNF4α/GFP. Cells were transduced in vitro at an MOI of 2000, and the transduction efficiency in vitro was >90%.

A 1.5 kb EcoR1 fragment of rat-HNF4α 2 was cloned into the bicistronic plasmid pAAV-IRES-GFP (Cell Biolabs, Inc; San Diego, Calif.), which expresses HNF4α under control of the CMV promoter and GFP under control of the IRES promoter. AAV vector preparation was performed using the helper-virus-free $CaPO_4$ triple transfection method. Briefly, HEK293 cells were grown in DMEM with 10% FCS to 75% confluence in 12 150 $cm^2$ flasks. For each flask, 15 ug of each plasmid [pAAV-CMV-HNF4α/IRES-GFP, pladeno5 (32), pAAV-DJ (33)] was added to 3 ml of 300 mM $CaCl_2$. This mixture was then added to 3 ml of 2×-HEPES-buffered saline (50 mM HEPES [N-2-hydroxyethylpiperazine-N'-2-ethanesulfonic acid], 280 mM NaCl, 1.5 mM $NaH_2PO_4$, pH 7.1), vortexed and let stand for 5 minutes, then added to the flask and incubated at 37° C. for 4-6 hrs. Media was changed to DMEM with 2% FCS and cultured for 48-72 hrs. For harvest, EDTA was added to the flask to a final concentration of 10 mM and incubated for 3-5 min. Cells were dislodged by gentle shaking and cells and media were harvested and centrifuged at 100×g. The cell pellet was suspended in DMEM and subjected to 3 freeze-thaw cycles in dry-ice/ethanol and 37° C. baths. Cell debris was removed by centrifugation at 10,000×g for 10 min. Supernatant was collected and virus was purified and concentrated using the ViraBind™ AAV purification kit (Cell Biolabs, Inc; San Diego, Calif.) per manufacturer's instructions. Viral titer in genome copies (gc)/ml was determined by dot blot of serial dilutions of virus using linearized pAAV-CMV-HNF4α/IRES-GFP as a standard and a HNF4α cDNA fragment as probe.

Transduction to express HNF4α: For in vitro studies, freshly isolated hepatocytes were plated at a density of 0.5 million cells per well in collagen-coated 6-well plates. After incubation in DMEM/F12 for 2 hours at 37° C. and 5% CO2, the culture medium was changed to one containing each AAV vector at an MOI of 2000. Cells were incubated for 24 hours at 37° C. and 5% CO2, and then washed twice with PBS. Two ml of fresh culture medium was added into each well, starting 24 hours after AAV transduction (Day 0), and repeated daily up to day 7. Supernatant samples were collected and preserved at −80° C. After viral transduction, cell samples were also collected from each well on day 2 for extraction of genomic DNA, total RNA and whole cellular protein for analysis.

For AAV transduction in vivo, $3.0 \times 10^{11}$ viral genomes of AAV-DJ-HNF4α-IRES-GFP (n=5) and AAVDJ-IRES-GFP (n=4) were injected into the tail vein. Five animals with decompensated cirrhosis were also monitored that received no AAV infection as a control group. All animals were monitored and scored for clinical changes and by laboratory tests every week until expiration or until the end of the observation period at 14 weeks after viral infection. Untreated animals and animals treated with the control AAV-GFP vector developed progressively worsening liver function and died with a mean survival of 19 days. Treated rats showed improvement in clinical parameters, INR, total bilirubin, serum albumin level, and ammonia. All were nearly at normal levels within 2 weeks of treatment, and sustained those levels for at least 100 days. One animal treated with AAVDJ-HNF4α-IRES-GFP was sacrificed 2 weeks after viral injection to estimate early transduction efficiency. Survival assessment was statistically performed by log-rank test among three groups (*p<0.05). Value represent mean±SD. Specimens were collected following euthanasia and samples were preserved unfixed at −80° C., embedded in paraffin after 4% PFA fixation, and embedded in OTC compound after 2% PFA fixation. Vector transduction efficiency was estimated by immune detection for GFP.

Albumin measurement: Albumin levels from hepatocyte culture supernatants were measured by ELISA according to manufacture's instructions (Bethyl Laboratories, TX). Five hundred thousand freshly isolated viable hepatocytes were seeded into each well of a collagen-coated 6 well plate containing 2 ml DMEM/F12 and incubated overnight at 37° C. in 5% CO2. The culture medium was replaced with 2 ml of new every day. Collected samples were stored at −80° C. prior to analyses. For the ELISA, high binding 96 well plates (Corning, N.Y.) were coated with 100 uL of an anti-rat albumin affinity purified antibody (1:100) (Bethyl laboratories) in 0.05M carbonate-bicarbonate, pH 9.6 for 1 hr at 25° C. Plates were washed three times with 50 mM Tris, 0.14M NaCl, and 0.05% (v/v) Tween 20 pH 8.0. Nonspecific binding was blocked by adding 1% BSA for 1 h at 25° C. After washing three times, 200 uL of each sample (in duplicate) and standards were added and incubated for 1 h at 25° C. Samples were diluted as needed up to 1:150000 in 50 mM Tris, 0.14M NaCl, 1% BSA, and 0.05% (v/v) Tween 20 pH 8.0). Wells were then washed five times, and 100 uL of an anti-albumin HRP conjugate, diluted 1:10000 in the above buffer was added. Plates were incubated for 1 h at 25° C. After washing, 100 uL of substrate ABTS (KPL, MD) was added in each well. After 30 min, the reaction was stopped by adding 1% SDS to each well. Absorbance was measured at 405 nm using a Benchmark microplate reader (Biorad, CA). The absence of cross reactivity with fetal bovine serum (present in F-12 medium) was verified using samples of culture medium used as blanks. Lewis rat serum was used as a positive control.

CYP3A4 activity assay: Isolated cells were cultured in DMEM/F12 at density of 0.5 million cells per well in collagen-coated 6-well plates, as described above. CYP3A4 activity was measured on day 2 of culturing, when expression following HNF4α vector transduction had peaked, using the P450-Glo™ CYP3A4 assay kit (Promega Corporation, Madison, Wis.), according to manufacture's instructions. Briefly, the culture medium was exchanged with one ml of fresh media (without Phenol red) containing 3 uM Luciferin-IPA. After incubation for 30 minutes at 37° C., 200 ul of culture supernatant was collected from each well and transferred into luminometer tubes. Then 200 ul of Luciferin detection regent was added into each tube. The mixture was incubated for 20 minutes at room temperature, protected from light, and the luminescence was immediately detected using a TD-20/20 luminometer (Turner BioSystems, Inc., Sunnyvale, Calif.).

Statistical analysis: Differences among group results were deemed significant when the P-value was less than 0.05. Statistical analyses were performed using the Tukey-Kramer multiple comparisons procedure and Student's t-test using SPSS v16.0 software (SPSS Inc., Chicago, Ill., USA). Survival in vivo was evaluated by log-rank test. Each value represents the mean±SD. Statistical analysis was performed among three groups (normal, compensated and decompensated cirrhotic hepatocytes) and between un-treated decompensated cirrhotic hepatocytes and decompensated cirrhotic hepatocytes 14 weeks after in vivo HNF4α re-expression (*p<0.05,**P<0.001).

Example 2: Effect of Transient Expression of Exogenous HNF4α in Cirrhotic Rats

Short-term HNF4α re-expression may reactivate the hepatocyte transcription factor network. Alternatively, the therapeutic effects could require continuous expression of exogenous HNF4α. Determination of which scenario is accurate will profoundly affect clinical therapeutic strategies. Therefore, a recombinant AAV vector is constructed that expresses HNF4α from an inducible promoter controlled by Tet-ON/OFF system.

The bicistronic vector ("Tet-ON:AAV-CMV-rtTA/TRE-HNF4a", modeled after Zheng et al. (2012 *BMC Cancer,* 12:153) will express the rtTA (Tet repressor) under the control of a CMV promoter and the human HNF4α cDNA under the control of the TRE (tet regulated promoter). The CMV-rtTA is 2200 bp and the TRE-HNF4α is 2100 bp, a total within the 5 kb capacity of AAV. Tet ON:AAV-CMV rtTA/TRE-GFP is generated as a control virus. Transduction efficiency and efficacy of the conditional constructs is confirmed by immunochemistry and in vitro studies.

An alternative approach will be to simultaneously administer separate viruses containing the rtTA and TREHNF4 or TRE-GFP. IV injection on 2-consecutive days can also be done to achieve maximal target cell transduction with no increased immune response. Tetracycline inducible systems have been widely used to administer regulated gene expression, but expression can be leaky. Therefore, a newer third generation Tetracycline-inducible system, the Tet-ON-3 G (Clontech), will be utilized, which has been engineered to have reduced basal expression and enhanced sensitivity to doxycycline.

HNF4α expression is induced by administration of doxycycline (1 mg/ml in drinking water) and animals will be assessed weekly for improved hepatic function (INR, total bilirubin, serum NH3, albumin, and encephalopathy score). Exogenous HNF4α expression is halted by withdrawal of doxycycline at one, 2, 4, 6, and 8 weeks after correction of hepatic function and assessed for sustained normalization of hepatic function and survival. If liver function does not deteriorate 2 weeks after withdrawal of exogenous HNF4α expression (i.e., animals are improving), liver specimens are collected and HNF4α expression is determined by immunohistochemistry, Western blot, northern blot, and qPCR. Hepatocytes are also isolated from treated cirrhotic livers and examined following cytospin for gene expression by IHC (HNF4α, albumin, etc.). In addition, RNA is collected from hepatocytes for qPCR analysis to assess HNF4α expression and associated changes in liver specific gene expression. Exogenous and endogenous HNF4α expression is distinguished by qRT-PCR, since the mRNAs differ in their 3'-untranslated regions.

Example 3: Effect of Ongoing $CCl_4$ Treatment on Liver Function and Gene Expression in Cirrhotic Rats with Liver Failure Treated with AAV-HNF4/GFP Human cirrhosis patients have continuing injury, whether from alcohol, HCV, or other chronic insults. Therefore, how HNF4α therapy modulates continuing injury with $CCl_4$ is studied. Rats with end-stage cirrhosis whose liver function has been corrected following administration with AAV-HNF4α receive ongoing treatment with $CCl_4$, starting 2 weeks after AAV treatment. Animals are assessed weekly by blood tests for maintenance of improved hepatic function following AAV-HNF4α treatment. $CCl_4$ treatment is discontinued if the hepatic encephalopathy score falls below 9 (Kobayashi, et al. 2000, *Hepatology* 31(4):851; Bures, et al. Innate and motivated behavior. Techniques and Basic Experiments for the Study of Brain and Behavior. New York: Elsevier; 1976, p. 37-45)). If hepatic function deteriorates but does not correct within 2 weeks of stopping treatment with $CCl_4$, animals are sacrificed and liver specimens and isolated hepatocytes are examined for HNF4α and liver-specific gene expression.

Example 4: To Determine the Mechanism of HNF4α Downregulation in Human End-Stage Cirrhosis and to Examine Whether Exogenous HNF4α can Correct for Loss of Function To extend the rat observations to human liver disease, control and cirrhotic livers are examined for function and changes in gene expression and chromatin. There are a wide variety of fibrotic liver diseases, with some differences from the rat $CCl_4$ model. Nevertheless, the focus on liver failure via transcriptionally regulated hepatocyte decompensation is distinctive, and there is a striking similarity between the rat and human diseases. It has been found that HNF4α expression is a dramatically diminished in cirrhotic livers with decompensated hepatic function (Berasain, C. et al. 2003 *Hepatology* 38(1):148-57). Thus, the extent to which networks altered in rodent studies are similarly altered in human hepatocytes will be determined. Since diminished HNF4α expression has been identified, further examination focuses on the extent to which providing exogenous HNF4α to human hepatocytes will correct hepatic function toward normal.

Characterization of Transplanted Hepatocytes Derived from Cirrhotic Livers.

In the animal studies described herein, the yield of hepatocytes recovered by collagenase digestion of cirrhotic livers was significantly lower than from age-matched controls, but hepatocyte viability and plating efficiency were not statistically different among groups. However, hepatocytes from the livers of rats with decompensated cirrhosis functioned less well in vitro than those from all other donor groups. Preliminary studies of human disease were performed, using explanted diseased livers recovered during liver transplantation at Children's Hospital of Pittsburgh. Cirrhotic livers were classified according to severity based on Child-Pugh Classification of severity of liver disease (determined based on the criteria set forth in Table 2, below). Cells were isolated from cirrhotic livers, from the livers of patients with liver-based metabolic disorders, and from pediatric age-matched controls. There was no difference in viability or plating efficiency within groups. However, albumin secretion and urea synthesis was significantly diminished in hepatocytes from Child-B livers. A decrease in inducible CYP 1A1/1A2 activity in hepatocytes from human Child-B but not Child-A cirrhotic hepatocytes was observed. As cirrhosis became more advanced, human hepatocytes showed an increase in mRNA expression for progenitor cell genes, most markedly for CD44 and EpCAM.

TABLE 2

Criteria for Child-Pugh Classification
Scores for each of five clinical and biochemical
measurements are combined for a Grade,
Grade A = 5-6 Grade B = 7-9 Grade C = 10-15

| Clinical and Biochemical Measurements | Points Scored for Increasing Abnormality | | |
|---|---|---|---|
| | 1 | 2 | 3 |
| Hepatic encephalopathy (grade)* | None | 1 and 2 | 3 and 4 |
| Ascites | Absent | Mild | Moderate |
| Total bilirubin (mg/dl) | <2.0 | 2.0-3.0 | >3.0 |
| Serum albumin (g/dl) | >3.5 | 2.8-3.5 | <2.8 |
| Prothrombin time (sec. prolonged) or Prothrombin time INR** | <4 or <1.7 | 4-6 or 1.7-2.3 | >6 or >2.3 |

*According to grading of Trey, Burns, and Saunders (1996).
**Lucey MR, et al. Minimal Criteria for Placement of Adults on the Liver Transplant Waiting List *Liver Transplantation and Surgery*, Vol. 3, No 6 (November), 1997: pp 628-637.

HNF4α Expression is Downregulated in Human Livers with Advanced Cirrhosis.

As in rat cirrhosis, HNF4α downregulation occurs in human livers with advanced cirrhosis (Berasain, C. et al. 2003 *Hepatology* 38(0:148-57). This finding was confirmed by qPCR of cirrhotic and control hepatocytes recovered at Children's Hospital of Pittsburgh. By qRT-PCR, levels of HNF4α were significantly lower than that found in control normal livers.

Research Design:
Characterization of Human Livers and Hepatocytes Derived from these Livers.

Normal livers from nonheart-beating donors, and livers representing different stages of fibrosis and cirrhosis are recovered for analysis. Serum bilirubin, albumin, INR level, extent of ascites, and encephalopathy are recorded for each liver where hepatocytes are recovered. Tissue biopsies assess the extent of regenerative hyperplasia and cirrhosis. Extent of collagen deposition is determined by Masson-Trichrome and Sirius red-stained sections using ImageJ software. The yield of hepatocytes from cirrhotic and control livers recovered by collagenase digestion, including their viability and plating efficiency, us recorded. Four groups are established based on severity of donor liver disease. Group 1: normal control livers; Group 2: livers with significant liver injury but associated with no, or minimal, change in hepatic function (Child-Pugh A); Group 3: livers with modest loss of function (Child-Pugh B); Group 4: livers with severe loss of hepatic function (Child-Pugh C).

Baseline Functional Analysis and Gene Expression Profile of Hepatocytes Recovered from Human Livers.

As with hepatocytes derived from our rat model, measure human hepatocyte function is measured [albumin secretion, urea synthesis, qPCR for expression of liver-specific genes including HNF4α, and baseline and induced cytochrome P450 activity; evidence of replicative senescence [qRT-PCR for NF-kB, telomerase expression, functional telomerase activity, and telomere length (Southern blot analysis)].

Differences among groups are analyzed statistically using ANOVA. It has been calculated that at least 10 samples representing each experimental group is required for comparison.

Human-Rat Comparison of the Dynamic Genetic Changes Associated with Progressive Cirrhosis and Liver Failure.

RNA-Seq analysis is carried out and expression levels of selected liver specific genes are also examined by quantitative PCR. As in the rodent studies, transcriptome analysis provides a fundamental resource for elucidating the mechanisms by which cells derived from normal, compensated, and decompensated cirrhotic livers develop hepatic dysfunction. The cluster analysis of the rat studies revealed signatures of NFκB stimulation and HNF4α inhibition (see above) (Liu, L. et al. 2012 *Hepatology* 55(5):1529-39). It is hypothesized that similar patterns of expression will discriminate normal vs. compensated vs. decompensated cirrhosis in human livers. Hepatocytes, recovered as outlined above, and donor liver segments are processed for mRNA and subsequent analysis by RNA-Seq. transcriptomic dynamics of normal liver cells is defined, followed by a similar analysis of cells derived from compensated cirrhotic livers, culminating in an analysis of the transcriptomic dynamics of hepatocytes from decompensated cirrhotic livers.

Transduction of Hepatocytes from Cirrhotic Human Livers Associated with Decompensated Function to Express HNF-4a.

Adult human hepatocytes derived from end-stage cirrhotic livers are transduced to express HNF4α by AAV. MOI is optimized to attain >80% transduction of human hepatocytes without injury. An AAV vector has been generated containing the gene encoding human HNF4α. However, a new vector expressing both HNF4α and GFP is constructed to allow easy assessment of transduction efficiency. Controls receive a GFP-expressing vector. $5 \times 10^5$ human hepatocytes are cultured in each well of a 6-well plate. Following transduction, liver-specific gene expression is assessed in hepatocytes from normal and decompensated Child's A, B, and C livers. Following transduction, supernatants are collected daily from hepatocytes for measurement of albumin and urea secretion. Furthermore, mRNA is recovered from hepatocytes and qRT-PCR is performed to assess AAT, ApoA, ApoC, Cyp3A4, FVII, HNF1α, TAT, Tdo2, TF, TTR, and endogenous and exogenous HNF4α expression. All values are normalized to control normal hepatocytes.

Transplantation of HNF4α Treated Human Hepatocytes from Cirrhotic Livers into Immune Deficient Mice FAH k/o Mice.

Control human hepatocytes and AAV-HNF4α transduced hepatocytes are transplanted into immune-deficient FAH K/O (FRG or FRG-NOD) mice that provide a selective repopulation advantage to donor cells. FRG/N mice (6-12 week old), maintained on 2-(2-nitro-4-trifluoro-methyl-benzoyl)-1,3 cyclohexanedione (NTBC)-containing drinking water at 16 mg/L, receive $5 \times 10^9$ pfu Ad-uPA i.p. before transplantation (Lieber, A. et al. 1995 *Hum Gene Ther.* 6(8):1029-37; Azuma, H. et al. 2007 *Nature Biotechnology* 25(8):903-10). $10^6$ viable human hepatocytes are then transplanted into the spleen for engraftment in the liver. NTBC is gradually decreased (1.6 mg/l, day 0-2; 0.8 mg/l, day 3-4; 0.4 mg/l, day 5-6) and completely withdrawn one week after transplantation. Two weeks after stopping NTBC, animals are placed back on the drug for 5 d and then taken off again. NTBC may need to be repeatedly restarted for 5 days each time the body weight decreases by 20 percent in order to allow expansion of transplanted hepatocytes. Human serum albumin level is used to non-invasively assess the extent to which engrafted donor hepatocytes function and expand in the non-cirrhotic FRG/N liver environment over time. 4-8 weeks after transplantation, when human serum albumin approaching 0.5 mg/ml indicates engraftment by human hepatocytes approximating 5-10% repopulation, hepatocytes are isolated by in situ collagenase perfusion (Berry, M N. et al. 1969 *PMCID*:PMCID2107801; Seglen P A, 1976 *Method Cell Biol.* 13:29-83). Isolated cells are placed in fresh media containing homogentisic acid (HGA), the intermediate metabolite in the pathway between 4-hydroxyphenylpyruvate dioxygenase and FAH, for 24 hrs. Donor cells that express FAH survive this treatment, whereas FAH-deficient cells do not survive (Kubo S. et al. 1998 *PNAS USA* 95(16):9552-7).

As predicted, is was found that FAH-deficient hepatocytes die in a dose-dependent fashion. As with hepatocytes derived from control and cirrhotic rats, human hepatocyte function: albumin secretion, urea synthesis, and qPCR is measured for expression of liver-specific genes including HNF4α, baseline and induced cytochrome P450 activity (CYP3A4, 2C9, 1A1, 1A2), and evidence of replicative senescence (telomerase expression, functional telomerase activity, and telomere length) (Kitada T, et al. 1995 *Biochem Biophys Res Commun* 211(1):33-9; Rudolph L K et al. Telomeres and telomerases in experimental liver cirrhosis. Chisari F V, et al. editors. In: The Liver: Biology and Pathobiology. 4th ed. Philadelphia: Lippincott Williams & Wilkins; 2001. p. 1000-10; Wiemann S U, et al. 2002, *FASEB J.* 16(9):935-42).

Differences between experimental and controls are analyzed statistically using ANOVA. At least 10 samples representing each group are required for comparison.

REFERENCES

1. F. Durand, D. Valla, *J Hepatol* 42 Suppl, S100 (2005).
2. P. Gines, A. Cardenas, V. Arroyo, J. Rodes, *N Engl J Med* 350, 1646 (Apr. 15, 2004).
3. D. Schuppan, N. H. Afdhal, *Lancet* 371, 838 (Mar. 8, 2008).
4. A. Martinez-Hernandez, J. Martinez, *Hepatology* 14, 864 (November, 1991).
5. S. L. Friedman, *J Hepatol* 38 Suppl 1, S38 (2003).

6. D. Pessayre, D. Lebrec, V. Descatoire, M. Peignoux, J. P. Benhamou, *Gastroenterology* 74, 566 (March, 1978).
7. M. Vaubourdolle et al., *Scand J Gastroenterol* 24, 467 (May, 1989).
8. P. M. Lopez, P. Martin, *Mt Sinai J Med* 73, 1056 (December, 2006).
9. S. Marro et al., *Cell Stem Cell* 9, 374 (Oct. 4, 2011).
10. K. Takahashi et al., *Cell* 131, 861 (Nov. 30, 2007).
11. N. Kobayashi et al., *Hepatology* 31, 851 (April, 2000).
12. J. Locker, in *Molecular Pathology of Liver Diseases*, S. P. Monga, Ed. (Springer, New York, 2011), pp. 193-2011.
13. F. M. Sladek, S. Seidel, in *Nuclear Receptors and Genetic Disease*, T. P. B. E. McCabe, Ed. (Academic Press, London, 2001).
14. L. Liu et al., *Hepatology* 55, 1529 (May, 2012).
15. C. Berasain et al., *Hepatology* 38, 148 (July, 2003).
16. P. B. Limaye et al., *Lab Invest* 88, 865 (August, 2008).
17. E. Bolotin et al., *Hepatology* 51, 642 (February, 2010).
18. H. Nagata et al., *Gastroenterology* 124, 422 (February, 2003).
19. H. Y. Yue et al., *Gut* 59, 236 (February, 2010).
20. I. Kyrmizi et al., *Genes Dev* 20, 2293 (Aug. 15, 2006).
21. D. T. Odom et al., *Mol Syst Biol* 2, 2006 0017 (2006).
22. G. P. Hayhurst, Y. H. Lee, G. Lambert, J. M. Ward, F. J. Gonzalez, *Mol Cell Biol* 21, 1393 (February, 2001).
23. F. Parviz et al., *Nat Genet* 34, 292 (July, 2003).
24. F. M. Sladek, W. M. Zhong, E. Lai, J. E. Darnell, Jr., *Genes Dev* 4, 2353 (December, 1990).
25. F. J. Gonzalez, *Drug Metab Pharmacokinet* 23, 2 (2008).
26. G. K. Michalopoulos, *Am J Pathol* 176, 2 (January, 2010).
27. N. Kobayashi et al., *Hepatology* 31, 851 (April, 2000).
28. J. B. O. Bures, J. P. Huston, in *Techniques and Basic Experiments for the Study of Brain and Behavior*. (Elsevier, New York, 1976), pp. 37-45.
29. M. N. Berry, D. S. Friend, *J Cell Biol* 43, 506 (December, 1969).
30. P. O. Seglen, *Methods Cell Biol* 13, 29 (1976).
31. R. M. Cawthon, *Nucleic Acids Res* 30, e47 (May 15, 2002).
32. T. Matsushita et al, *Gene Ther* 5, 938 (July, 1998).
33. D. Grimm et al., *J Virol* 82, 5887 (June, 2008).

Various publications, patents, patent applications, and GenBank Accession Nos. are cited herein, the contents of which are hereby incorporated by reference in their entireties.

The invention claimed is:

1. A method of treating hepatic failure in a human subject, comprising administering intravenously, to a human subject having liver failure, a therapeutically effective amount of a pharmaceutical composition comprising a therapeutic adeno-associated virus vector comprising a nucleic acid encoding a human HNF4α, protein operably linked to a promoter, wherein administration of said nucleic acid results in expression of the human HNF4α protein and improved liver function.

2. The method of claim 1, wherein the improved liver function is indicated by an increase in serum albumin.

3. The method of claim 1, wherein the improved liver function is indicated by decreased serum ammonia level.

4. The method of claim 1, wherein the improved liver function is indicated by a decrease in total bilirubin.

5. The method of claim 1, wherein the improved liver function is indicated by an improved encephalopathy score.

6. The method of claim 1, wherein the administration of said nucleic acid treats Child-Pugh Class B or C.

* * * * *